(12) United States Patent
Knick et al.

(10) Patent No.: US 7,648,703 B2
(45) Date of Patent: Jan. 19, 2010

(54) COMBINATION OF ANTI-EP-CAM ANTIBODY WITH A CHEMOTHERAPEUTIC AGENT

(75) Inventors: Vincent C. Knick, Durham, NC (US); Julie Beth Stimmel, Durham, NC (US); Linda M. Thurmond, Durham, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 124 days.

(21) Appl. No.: 11/034,655

(22) Filed: Jan. 13, 2005

(65) Prior Publication Data

US 2005/0163785 A1 Jul. 28, 2005

Related U.S. Application Data

(63) Continuation of application No. 10/031,355, filed as application No. PCT/EP99/05271 on Jul. 23, 1999, now abandoned.

(51) Int. Cl.
*A61K 39/395* (2006.01)
*C07K 7/00* (2006.01)

(52) U.S. Cl. ............... 424/141.1; 424/155.1; 424/156.1

(58) Field of Classification Search .................. None
See application file for complete search history.

(56) References Cited

FOREIGN PATENT DOCUMENTS

| EP | 0252741 A | 1/1988 |
|---|---|---|
| WO | WO 87/00462 | 1/1987 |
| WO | WO 92/07075 | 4/1992 |
| WO | 99/31140 | 6/1999 |

OTHER PUBLICATIONS

Bebbington et al., "High-level expression of a recombinant antibody from myeloma cells using a glutamine synthetase gene as an amplifiable selectable marker," *Bio/Technology* 10:169-175 (Feb. 1992).
Bhuyan et al., "Lethality, DNA alkylation, and cell cycle effects of adozelesin (U-73975) on rodent and human cells," *Cancer Research* 52(2):5687-5692 (Oct. 1992).
Bleiberg, "Continuing the fight against advanced colorectal cancer: new and future treatment options," *Anti-Cancer Drugs* 9:1 18-28 (Jan. 1998).
Bokemeyer et al., "Current aspects of adjuvant and palliative chemotherapy in colorectal carcinoma!. Aktuelle Aspekte zur adjuvanten und palliativen Chemotherapie beim kolorektalen Karzinom," *Schweizerische Rundschau Fur Medizin Praxis* 86:39 1510-1516 (Sep. 1997).
Casillas et al., "Adjuvant therapy for colorectal cancer: present and future perspectives," *Diseases of the Colon and Rectum* 40:8 977-992 (Aug. 1997).
Chen et al., "Differences in inhibition of chromosome separation and $G_2$ arrest by DNA topoisomerase II inhibitors merbarone and VM-26," *Cancer Research* 55(7):1509-1516 (Apr. 1995).

Colcher et al., "A spectrum of monoclonal antibodies reactive human mammary tumor cells," *Proc. Natl. Acad. Sci. USA* 78(5):3199-3203 (May 1981).
Czuczman et al., "IgM monoclonal antibody JD118 recognizes an inducible antigen target for human-complement-mediated cytotoxicity against neoplastic B cells," *Cancer Immunology, Immunotherapy* 36(6):387-396 (1993).
Elias et al., "Monoclonal antibody KS1/4-methotrexate immunoconjugate studies in non-small cell lung carcinoma," *American Journal of Respiratory and Critical Care Medicine* 15:4 1114-1122 (Oct. 1994).
Ellis et al., "Engineered anti-CD38 monoclonal antibodies for immunotherapy of multiple myeloma," *The Journal of Immunology* 155:925-937 (1995).
Engelholm et al., "Effect of Melphalan on growth curves and cell cycle distribution of four human small cell carcinomas of the lung grown in nude mice," *Experimental Cell Biology* 54(3):138-148 (1986).
Erba et al., "Comparison of cell-cycle phase perturbations induced by the DNA-minor-groove alkylator tallimustine and by melphalan in the SW626 cell line," *International Journal of Cancer* 62(2):170-175 (Jul. 1995).
Fargion et al., "Heterogeneity of cell surface antigen expression of human small cell lung cancer detected by monoclonal antibodies," *Cancer Research* 46:2633-2638 (May 1986).
Fogler et al., "Enhanced cytotoxicity against colon carcinoma by combinations of noncompeting monoclonal antibodies to the 17-1A antigen," *Cancer Research* 48:6303-6308 (1988).
Greiner et al., "Enhanced expression of surface tumor-associated antigens on human breast and colon tumor cells after recombinant human leukocyte α-interferon treatment," *Cancer Research* 44:3208-3214 (Aug. 1984).
Greiner et al., "Intraperitoneal administration of interferon-gamma to carcinoma patients enhances expression of tumor-associated glycoprotein-72 and carcinoembryonic antigen on malignant ascites cells," *J. Clin Oncol* 10(5):735-746 (May 1992).
Haisma et al., "A monoclonal antibody-beta-glucuronidase conjugate as activator of the prodrug epirubicin-glucuronide for specific treatment of cancer," *British Journal of Cancer* 66:3 474-478 (Sep. 1992).
Herlyn et al., "Colorectal carcinoma-specific antigen: detection by means of monoclonal antibodies," *Proc. Natl. Acad. Sci. USA* 76(3):1438-1452 (Mar. 1979).
Herlyn et al., "CO 17-1A and related monoclonal antibodies: their production and characterization," *Hybridoma* 5(Suppl. 1):S3-S10 (1986).
Inaba et al., "Flow cytometric analysis of cell-killing actions of 5-fluorouracil in human colorectal cancer cells," *Oncology Research* 6(7):303-309 (1994).
Jones et al., "Replacing the complementarity-determining regions in a human antibody with those from a mouse," *Nature* 321:522 (May 1986).
Kallio et al., "Effects of the DNA topoisomerase II inhibitor merbarone in male mouse meiotic divisions in vivo: Cell cycle arrest and induction of aneuploidy," *Environmental & Molecular Mutagenesis* 29(1):16-27 (1997).

(Continued)

*Primary Examiner*—Sheela J Huff
(74) *Attorney, Agent, or Firm*—Michael M. Conger

(57) ABSTRACT

A combination of an anti-Ep-CAM antibody with a chemotherapeutic agent that is capable of arresting Ep-CAM antigen expressing cells in S or $G_2/M$.

4 Claims, 24 Drawing Sheets

OTHER PUBLICATIONS

Figure 1:
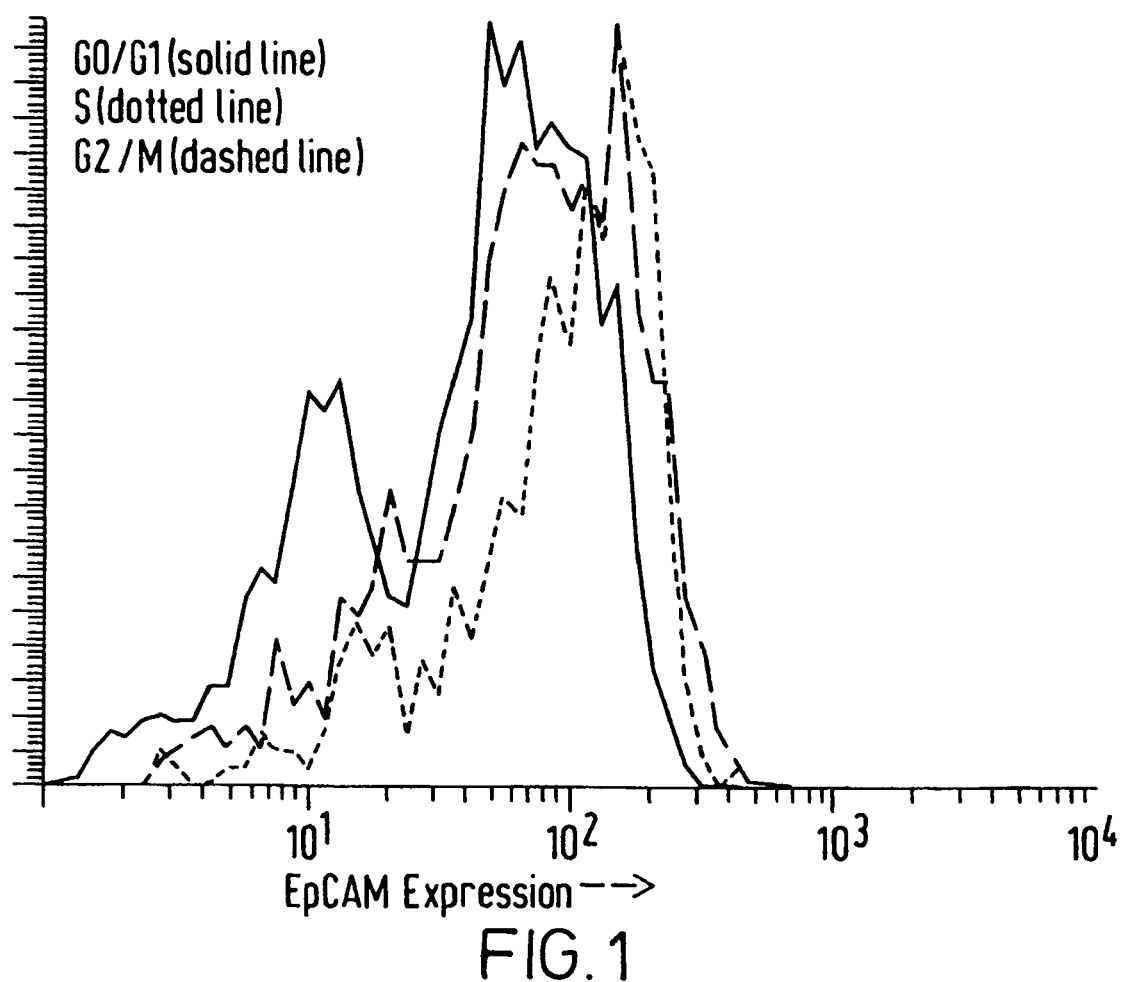

Kievit et al., "Determination of tumor-related factors of influence on the uptake of the monoclonal antibody 323/A3 in experimental human ovarian cancer," *International Journal of Cancer* 71:2 237-245 (Apr. 1997).

Klucar et al., "G2 cell cycle arrest and apoptosis are induced in Burkitt's lymphoma cells by the anticancer agent oracin," *FEBS Letters* 400(1):127-130 (Jan. 1997).

Laio et al., "Binding and functional properties of a mouse-human chimeric monoclonal antibody of the human IgG1 subclass with specificity for human carcinomas," *Human Antibody Hybridomas* 1(2):66-76 (1990).

Litvinow et al., "Ep-CAM: a human epithelial antigen is a homophilic cell-cell adhesion molecule," *J. Cell Biology* 125:437-446 (1994).

Okabe et al., "Monoclonal antibodies to surface antigens of small cell carcinoma of the lung," *Cancer Research* 44:5273-5278 (Nov. 1984).

Paul et al., "Treatment of advanced measurable or evaluable pancreatic carcinoma with 17-1A murine monoclonal antibody alone or in combination with 5-fluorouracil, adriamycin and mitomycin (FAM)," *Hybridoma* 5 Suppl:1 S171-S174 (Jul. 1986).

Reichmann et al., "Reshaping human antibodies for therapy," *Nature* 332:323-327 (Mar. 1988).

Riethmuller et al., "Monoclonal antibodies in the detection and therapy of micrometastatic epithelial cancers," *Curr. Opin. Immun.* 4:647-655 (1992).

Riethmuller et al., "Monoclonal antibodies in cancer therapy," *Curr. Opin. Immun.* 5:732-739 (1993).

Rojas et al., "Genotoxic effects of bistratene A on human lymphocytes," *Mutation Research* 367(3):169-175 (Mar. 1996).

Schwartzberg, "Chemotherapy plus PANOREX (17-1A monoclonal antibody) as adjuvant therapy for colon cancer: Ongoing studies," *Cancer Investigation* 17Suppl:1 32-34 (1999).

Song, "Expression of sarcoma-associated antigens p102 and p200 in human sarcoma cell lines," *Anticancer Research* 16(3A):1171-1175 (1996).

Stephens et al., "The construction of a highly efficient and versatile set of mammalian expression vectors," *Nucleic Acid Res.* 17(17):7110 (1989).

Tyle, "Iontophoretic devices for drug delivery," *Pharmaceutical Research* 3(6):318-326 (1986).

Verhoeyen et al., "Reshaping human antibodies: grafting an antilysozyme activity," *Science* 239:1534-1536 (Mar. 1988).

Watters et al., "Accumulation of HL-60 leukemia cells in G2/M and inhibition of cytokinesis caused by two marine compounds, bistratene A and cycloxazoline," *Cancer Chemotherapy & Pharmacology* 33(5):399-409 (1994).

Wei et al., "Expression of the surface antigen in human gastric cancer cells and the relation to cell cycles," *J of Oncology* 9(3):179-182 (1987) (Abstract).

Wulf et al., "A cell-surface apitope associated with liver-preferential metastasis detected by the new monoclonal antibody 3H4 in the murine tumor model ER 15-P," *J Cancer Research and Clinical Oncology* 122(8):476-482 (1996).

Ciardiello et al., Antitumor Activity of Sequential Treatment with Topotecan and Anti-epidermal Growth Factor Receptor Monoclonal Antibody C225[1], Clinical Cancer Research 5:909-916 (Apr. 1999).

Goldenberg, Trastuzumab, a Recombinant DNA-Derived Humanized Monclonal Antibody, a Novel Agent for the Treatment of Metastatic Breast Cancer, Clinical Therapeutics 21(2):309-318 (1999).

Ishikawa et al., Antitumor Activities of a Novel Fluoropyrimidine, $N^4$-Pentyloxycarbonyl-5'-deoxy-5-fluorocytidine (Capecitabine), Biol. Pharm. Bull. 21(7):713-717 (1998).

Maloney et al., Monoclonal Antibody Therapy, Chapter 21, The Molecular Basis of Cancer, pp. 460-510 (1995).

Mendelsohn, Epidermal Growth Factor Receptor Inhibition by a Monoclonal Antibody as Anticancer Therapy, Clinical Cancer Research 3:2703-2707 (Dec. 1997).

Miwa et al., Design of a Novel Oral Fluoropyrimidine Carbamate, Capecitabine, which Generates 5-Fluorouracil Selectively in Tumours by Enzymes Concentrated in Human Liver and Cancer Tissue, Eur. J. of Cancer 34(8):1274-1281 (1998).

Murakami et al., Cell Cycle Regulation, Oncogenes, and Antineoplastic Drugs, Chapter 1, The Moelcular Basis of Cancer, pp. 3-17 (1995).

Pegram et al., Phase II Study of Receptor-Enhanced Chemosensitivity Using Recombinant Humanized Anti-p185 $^{HER2/neu}$ Monoclonal Antibody Plus Cisplatin in Patients with HER2/neu-Overexpressing Metastatic Breast Cancer Refractory to Chemotherapy Treatment, J. Clin. Oncol 16:2659-2671 (1998).

Pegram et al., Inhibitory effects of combinations of HER-2/*neu* antibody and chemotherapeutic agents used for treatment of human breast cancers, Oncogene 18:2241-2251 (1999).

Pietras et al., Antibody to HER-2/*neu* receptor blocks DNA repair after cisplatin in human breast and ovarian cancer cells, Oncogene 9:1829-1838 (1994).

Punt, New Drugs in the Treatment of Colorectal Carcinoma, Cancer 83(4):679-689 (Aug. 15, 1998).

Cancer Principles & Practice Oncology, ed. DeVita, Jr. et al., Chapter 19 (Ratain) (1997).

Riethmüller, et al., Monoclonal Antibody Therapy for Resected Dukes C Colorectal Cancer: Seven-Year Outcome of a Multicenter Randomized Trial, J. Clin. Oncology 16:1788-1794 (1998).

Abstract #1385, Riethmüller, et al., Monoclonal Antibody (MAB) Adjuvant Therapy of Dukes C Colorectal Carcinoma 7-Year Update of a Prospective Randomized Trial, Proceedings of ASCO 15 (Mar. 1996).

Ross et al., The HER-2/*neu* Oncogene in Breast Cancer: Prognostic Factor, Predictive Factor, and Target for Therapy, Stem Cells 16:413-428 (1998).

Schneider-Gädicke and Riethmüller, Prevention of Manifest Metastasis with Monoclonal Antibodies: A Novel Approach to Immunotherapy of Solid Tumours, Eur. J. of Cancer 31A(7/8):1326-1330 (1995).

Scotto and Bertino, Chemotherapy Susceptibility and Resistance, The Molecular Basis of Cancer, eds. Mendelsohn, Howley, Israel, Liotto, 1995.

Tankanow, Docetaxel: A taxoid for the treatment of metastatic breast cancer, Am. J. Health-Syst Pharm. 55:1777-1791 (1998).

Molecular Biology of The Cell, $2^{nd}$ ed., eds Alberts et al., pp. 235-236 and 728 (1989).

Humanised 323/A3 (IgG$_1$) Kappa Light Chain Amino Acid Sequence SEQ ID NO:11

The amino acid sequence of the humanized light chain of 323/A3 IgG$_1$, including leader peptide, is shown below.

| | | | | |
|---|---|---|---|---|
| 1 | MGWSCIILFL | VATATGVHSD | IVMTQSPLSL | PVTPGEPASI |
| 41 | SCRSSKNLLH | SNGITYLYWY | LQKPGQSPQL | LIYQMSNLAS |
| 81 | GVPDRFSSSG | SGTDFTLKIS | RVEAEDVGVY | YCAQNLEIPR |
| 121 | TFGQGTKVEI | KRTVAAPSVF | IFPPSDEQLK | SGTASVVCLL |
| 161 | NNFYPREAKV | QWKVDNALQS | GNSQESVTEQ | DSKDSTYSLS |
| 201 | STLTLSKADY | EKHKVYACEV | THQGLSSPVT | KSFNRGEC |

FIG. 6

Humanised 323/A3 (IgG$_1$) Heavy Chain Amino Acid Sequence

The final amino acid sequence of the humanized heavy chain 323/A3 IgG$_1$, including leader peptide, is shown below. SEQ ID NO:12

| | | | | |
|---|---|---|---|---|
| 1 | MGWSCIILFL | VATATGVHSQ | VQLVQSGPEV | KKPGASVKVS |
| 41 | CKASGYTFTN | YGMNWVRQAP | GQGLEWMGWI | NTYTGEPTYG |
| 81 | EDFKGRFAFS | LDTSASTAYM | ELSSLRSEDT | AVYFCARFGN |
| 121 | YVDYWGQGSL | VTVSSASTKG | PSVFPLASS | KSTSGGTAAL |
| 161 | GCLVKDYFPE | PVTVSWNSGA | LTSGVHTFPA | VLQSSGLYSL |
| 201 | SSVVTVPSSS | LGTQTYICNV | NHKPSNTKVD | KKVEPKSCDK |
| 241 | THTCPPCPAP | ELLGGPSVFL | FPPKPKDTLM | ISRTPEVTCV |
| 281 | VVDVSHEDPE | VKFNWYVDGV | EVHNAKTKPR | EEQYNSTYRV |
| 321 | VSVLTVLHQD | WLNGKEYKCK | VSNKALPAPI | EKTISKAKGQ |
| 361 | PREPQVYTLP | PSRDELTKNQ | VSLTCLVKGF | YPSDIAVEWE |
| 401 | SNGQPENNYK | TTPPVLDSDG | SFFLYSKLTV | DKSRWQQGNV |
| 441 | FSCSVMHEAL | HNHYTQKSLS | LSPGK | |

FIG. 7

Humanised 323/A3 (IgG$_{4cys}$) Kappa Light Chain Amin Acid Sequence SEQ ID NO:13

The final amino acid sequence of the humanized light chain of 323/A3 IgG$_4$, including leader peptide, is shown below.

| | | | | |
|---|---|---|---|---|
| 1 | MGWSCIILFL | VATATGVHSD | IVMTQSPLSL | PVTPGEPASI |
| 41 | SCRSSKNLLH | SNGITYLYWY | LQKPGQSPQL | LIYQMSNLAS |
| 81 | GVPDRFSSSG | SGTDFTLKIS | RVEAEDVGVY | YCAQNLEIPR |
| 121 | TFGQGTKVEI | KRTVAAPSVF | IFPPSDEQLK | SGTASVVCLL |
| 161 | NNFYPREAKV | QWKVDNALQS | GNSQESVTEQ | DSKDSTYSLS |
| 201 | STLTLSKADY | EKHKVYACEV | THQGLSSPVT | KSFNRGEC |

FIG. 11

Humanised 323/A3 (IgG$_{4cys}$) Heavy Chain Amino Acid Sequence SEQ ID NO:14

The final amino acid sequence of the humanized heavy chain 323/A3 IgG$_4$, including leader peptide, is shown below.

| | | | | |
|---|---|---|---|---|
| 1 | MGWSCIILFL | VATATGVHSQ | VQLVQSGPEV | KKPGASVKVS |
| 41 | CKASGYTFTN | YGMNWVRQAP | GQGLEWMGWI | NTYTGEPTYG |
| 81 | EDFKGRFAFS | LDTSASTAYM | ELSSLRSEDT | AVYFCARFGN |
| 121 | YVDYWGQGSL | VTVSSASTKG | PSVFPLAPCS | RSTSESTAAL |
| 161 | GCLVKDYFPE | PVTVSWNSGA | LTSGVHTFPA | VLQSSGLYSL |
| 201 | SSVVTVPSSS | LGTKTYTCNV | DHKPSNTKVD | KRVESKYGPP |
| 241 | CPPCPAPEFA | GAPSVFLFPP | KPKDTLMISR | TPEVTCVVVD |
| 281 | VSQEDPEVQF | NWYVDGVEVH | NAKTKPREEQ | FNSTYRVVSV |
| 321 | LTVLHQDWLN | GKAYKCKVSN | KGLPSSIEKT | ISKAKGQPRE |
| 361 | PQVYTLPPSQ | EEMTKNQVSL | TCLVKGFYPS | DIAVEWESNG |
| 401 | QPENNYKTTP | PVLDSDGSFF | LYSRLTVDKS | RWQEGNVFSC |
| 441 | SVMHEALHNH | YTQKSLCLSL | GK | |

FIG. 12

Humanised 323/A3 (IgG$_{2cys}$) Kappa Light Chain Amino Acid Sequence SEQ ID NO:15

The final amino acid sequence of the humanized light chain of 323/A3 IgG$_{2cys}$, including leader peptide, is shown below.

| | | | | |
|---|---|---|---|---|
| 1 | MGWSCIILFL | VATATGVHSD | IVMTQSPLSL | PVTPGEPASI |
| 41 | SCRSSKNLLH | SNGITYLYWY | LQKPGQSPQL | LIYQMSNLAS |
| 81 | GVPDRFSSSG | SGTDFTLKIS | RVEAEDVGVY | YCAQNLEIPR |
| 121 | TFGQGTKVEI | KRTVAAPSVF | IFPPSDEQLK | SGTASVVCLL |
| 161 | NNFYPREAKV | QWKVDNALQS | GNSQESVTEQ | DSKDSTYSLS |
| 201 | STLTLSKADY | EKHKVYACEV | THQGLSSPVT | KSFNRGEC |

FIG. 13

Humanised 323/A3 (IgG$_{2cys}$) Heavy Chain Amino Acid Sequence SEQ ID NO:16

The final amino acid sequence of the humanized heavy chain of 323/A3 IgG$_{2cys}$, including leader peptide, is shown below.

| | | | | |
|---|---|---|---|---|
| 1 | MGWSCIILFL | VATATGVHSQ | VQLVQSGPEV | KKPGASVKVS |
| 41 | CKASGYTFTN | YGMNWVRQAP | GQGLEWMGWI | NTYTGEPTYG |
| 81 | EDFKGRFAFS | LDTSASTAYM | ELSSLRSEDT | AVYFCARFGN |
| 121 | YVDYWGQGSL | VTVSSASTKG | PSVFPLAPCS | RSTSESTAAL |
| 161 | GCLVKDYFPE | PVTVSWNSGA | LTSGVHTFPA | VLQSSGLYSL |
| 201 | SSVVTVPSSN | FGTQTYTCNV | DHKPSNTKVD | KTVERKCCVE |
| 241 | CPPCPAPPVA | GPSVFLFPPK | PKDTLMISRT | PEVTCVVVDV |
| 281 | SHEDPEVQFN | WYVDGVEVHN | AKTKPREEQF | NSTFRVVSVL |
| 321 | TVVHQDWLNG | KEYKCKVSNK | GLPAPAIEKTI | SKTKGQPREP |
| 361 | QVYTLPPSRE | EMTKNQVSLT | CLVKGFYPSD | IAVEWESNGQ |
| 401 | PENNYKTTPP | MLDSDGSFFL | YSKLTVDKSR | WQQGNVFSCS |
| 441 | VMHEALHNHY | TQKSLCLSLG | K | |

FIG. 14

Humanised 323/A3 (IgG₁) light chain DNA sequence
(also 323/A3 (IgG₄cys and IgG₂cys) light chain cDNA sequence) SEQ ID NOs: 1, 2 and 3

```
           10          20                   30          40          50
CGTAAGCTTC  ACAGGACCTC  ACC  ATG  GGA  TGG  AGC  TGT  ATC  ATC  CTC  TTC  TTG
GCATTCGAAG  TGTCCTGGAG  TGG  TAC  CCT  ACC  TCG  ACA  TAG  TAG  GAG  AAG  AAC
                        Met  Gly  Trp  Ser  Cys  Ile  Ile  Leu  Phe  Leu>

60              70              80              90         100
GTA  GCA  ACA  GCT  ACA  GGT  GTC  CAC  TCC  GAT  ATT  GTG  ATG  ACT  CAG  TCT
CAT  CGT  TGT  CGA  TGT  CCA  CAG  GTG  AGG  CTA  TAA  CAC  TAC  TGA  GTC  AGA
Val  Ala  Thr  Ala  Thr  Gly  Val  His  Ser>
                                       Asp  Ile  Val  Met  Thr  Gln  Ser>

110             120             130             140
CCA  CTC  TCC  CTG  CCC  GTC  ACC  CCT  GGA  GAG  CCG  GCC  TCC  ATC  TCC  TGT
GGT  GAG  AGG  GAC  GGG  CAG  TGG  GGA  CCT  CTC  GGC  CGG  AGG  TAG  AGG  ACA
Pro  Leu  Ser  Leu  Pro  Val  Thr  Pro  Gly  Glu  Pro  Ala  Ser  Ile  Ser  Cys>

150            160             170             180             190
AGG  TCT  AGT  AAG  AAT  CTC  CTG  CAT  AGT  AAT  GGC  ATC  ACT  TAT  TTG  TAT
TCC  AGA  TCA  TTC  TTA  GAG  GAC  GTA  TCA  TTA  CCG  TAG  TGA  ATA  AAC  ATA
Arg  Ser  Ser  Lys  Asn  Leu  Leu  His  Ser  Asn  Gly  Ile  Thr  Tyr  Leu  Tyr>

200            210             220             230             240
TGG  TAC  CTG  CAG  AAG  CCA  GGG  CAG  TCT  CCA  CAG  CTC  CTG  ATC  TAT  CAG
ACC  ATG  GAC  GTC  TTC  GGT  CCC  GTC  AGA  GGT  GTC  GAG  GAC  TAG  ATA  GTC
Trp  Tyr  Leu  Gln  Lys  Pro  Gly  Gln  Ser  Pro  Gln  Leu  Leu  Ile  Tyr  Gln>

250             260             270             280             290
ATG  TCC  AAC  CTT  GCC  TCA  GGG  GTC  CCT  GAC  AGG  TTC  AGT  AGC  AGT  GGA
TAC  AGG  TTG  GAA  CGG  AGT  CCC  CAG  GGA  CTG  TCC  AAG  TCA  TCG  TCA  CCT
Met  Ser  Asn  Leu  Ala  Ser  Gly  Val  Pro  Asp  Arg  Phe  Ser  Ser  Ser  Gly>

300             310             320             330             340
TCA  GGC  ACA  GAT  TTT  ACA  CTG  AAA  ATC  AGC  AGA  GTG  GAG  GCT  GAG  GAT
AGT  CCG  TGT  CTA  AAA  TGT  GAC  TTT  TAG  TCG  TCT  CAC  CTC  CGA  CTC  CTA
Ser  Gly  Thr  Asp  Phe  Thr  Leu  Lys  Ile  Ser  Arg  Val  Glu  Ala  Glu  Asp>

350             360             370             380
GTT  GGG  GTT  TAT  TAC  TGT  GCT  CAA  AAT  CTA  GAG  ATT  CCT  CGG  ACG  TTC
CAA  CCC  CAA  ATA  ATG  ACA  CGA  GTT  TTA  GAT  CTC  TAA  GGA  GCC  TGC  AAG
Val  Gly  Val  Tyr  Tyr  Cys  Ala  Gln  Asn  Leu  Glu  Ile  Pro  Arg  Thr  Phe>
```

FIG. 15

```
      390            400            410            420            430
GGC  CAA  GGG  ACC  AAG  GTG  GAG  ATC  AAA  CGT  ACG  GTG  GCT  GCA  CCA  TCT
CCG  GTT  CCC  TGG  TTC  CAC  CTC  TAG  TTT  GCA  TGC  CAC  CGA  CGT  GGT  AGA
Gly  Gln  Gly  Thr  Lys  Val  Glu  Ile  Lys  Arg>
                                             Thr  Val  Ala  Ala  Pro  Ser>

440            450            460            470            480
GTC  TTC  ATC  TTC  CCG  CCA  TCT  GAT  GAG  CAG  TTG  AAA  TCT  GGA  ACT  GCC
CAG  AAG  TAG  AAG  GGC  GGT  AGA  CTA  CTC  GTC  AAC  TTT  AGA  CCT  TGA  CGG
Val  Phe  Ile  Phe  Pro  Pro  Ser  Asp  Glu  Gln  Leu  Lys  Ser  Gly  Thr  Ala>

490            500            510            520            530
TCT  GTT  GTG  TGC  CTG  CTG  AAT  AAC  TTC  TAT  CCC  AGA  GAG  GCC  AAA  GTA
AGA  CAA  CAC  ACG  GAC  GAC  TTA  TTG  AAG  ATA  GGG  TCT  CTC  CGG  TTT  CAT
Ser  Val  Val  Cys  Leu  Leu  Asn  Asn  Phe  Tyr  Pro  Arg  Glu  Ala  Lys  Val>

540            550            560            570            580
CAG  TGG  AAG  GTG  GAT  AAC  GCC  CTC  CAA  TCG  GGT  AAC  TCC  CAG  GAG  AGT
GTC  ACC  TTC  CAC  CTA  TTG  CGG  GAG  GTT  AGC  CCA  TTG  AGG  GTC  CTC  TCA
Gln  Trp  Lys  Val  Asp  Asn  Ala  Leu  Gln  Ser  Gly  Asn  Ser  Gln  Glu  Ser>

590            600            610            620
GTC  ACA  GAG  CAG  GAC  AGC  AAG  GAC  AGC  ACC  TAC  AGC  CTC  AGC  AGC  ACC
CAG  TGT  CTC  GTC  CTG  TCG  TTC  CTG  TCG  TGG  ATG  TCG  GAG  TCG  TCG  TGG
Val  Thr  Glu  Gln  Asp  Ser  Lys  Asp  Ser  Thr  Tyr  Ser  Leu  Ser  Ser  Thr>

630            640            650            660            670
CTG  ACG  CTG  AGC  AAA  GCA  GAC  TAC  GAG  AAA  CAC  AAA  GTC  TAC  GCC  TGC
GAC  TGC  GAC  TCG  TTT  CGT  CTG  ATG  CTC  TTT  GTG  TTT  CAG  ATG  CGG  ACG
Leu  Thr  Leu  Ser  Lys  Ala  Asp  Tyr  Glu  Lys  His  Lys  Val  Tyr  Ala  Cys>

680            690            700            710            720
GAA  GTC  ACC  CAT  CAG  GGC  CTG  AGC  TCG  CCC  GTC  ACA  AAG  AGC  TTC  AAC
CTT  CAG  TGG  GTA  GTC  CCG  GAC  TCG  AGC  GGG  CAG  TGT  TTC  TCG  AAG  TTG
Glu  Val  Thr  His  Gln  Gly  Leu  Ser  Ser  Pro  Val  Thr  Lys  Ser  Phe  Asn>

730            740
AGG  GGA  GAG  TGT  TAG
TCC  CCT  CTC  ACA  ATC
Arg  Gly  Glu  Cys  --->
```

FIG. 15 cont.

FIG. 16

Humanised 323/A3 (IgG$_1$) heavy chain DNA sequence  SEQ ID NOs: 4 and 5

```
            10              20                  30          40          50
            .               .                   .           .           .
CGTAAGCTTC      ACAGATCCTC      ACC ATG GGA TGG AGC TGT ATC ATC CTC TTT CTG
                                    Met Gly Trp Ser Cys Ile Ile Leu Phe Leu>

60              70              80              90          100
        .               .               .               .           .
GTG GCA ACA GCT ACA GGT GTC CAC TCC CAG GTA CAG CTA GTG CAA TCA
Val Ala Thr Ala Thr Gly Val His Ser  Gln Val Gln Leu Val Gln Ser>

110             120             130             140
            .               .               .               .
GGG CCT GAA GTG AAG AAG CCT GGG GCC TCA GTG AAA GTT TCC TGC AAG
Gly Pro Glu Val Lys Lys Pro Gly Ala Ser Val Lys Val Ser Cys Lys>

150             160             170             180             190
.               .               .               .               .
GCT TCT GGC TAC ACC TTC ACC AAC TAT GGA ATG AAC TGG GTA AGG CAG
Ala Ser Gly Tyr Thr Phe Thr Asn Tyr Gly Met Asn Trp Val Arg Gln>

200             210             220             230             240
.               .               .               .               .
GCG CCT GGA CAG GGG CTT GAG TGG ATG GGG TGG ATA AAC ACC TAC ACT
Ala Pro Gly Gln Gly Leu Glu Trp Met Gly Trp Ile Asn Thr Tyr Thr>

250             260             270             280             290
    .               .               .               .               .
GGA GAG CCA ACA TAT GGT GAA GAT TTC AAG GGA CGG TTT GCA TTC TCT
Gly Glu Pro Thr Tyr Gly Glu Asp Phe Lys Gly Arg Phe Ala Phe Ser>

300             310             320             330             340
        .               .               .               .               .
CTA GAC ACA TCC GCC AGC ACA GCC TAT ATG GAG CTC AGC TCG CTG AGA
Leu Asp Thr Ser Ala Ser Thr Ala Tyr Met Glu Leu Ser Ser Leu Arg>

350             360             370             380
            .               .               .               .
TCC GAG GAC ACT GCA GTC TAT TTC TGT GCG AGA TTT GGT AAC TAC GTA
Ser Glu Asp Thr Ala Val Tyr Phe Cys Ala Arg Phe Gly Asn Tyr Val>

390             400             410             420             430
.               .               .               .               .
GAC TAC TGG GGT CAA GGA TCA CTA GTC ACT GTC TCC TCA GCC TCC ACC
Asp Tyr Trp Gly Gln Gly Ser Leu Val Thr Val Ser Ser  Ala Ser Thr>
```

|     | 440 |     |     | 450 |     |     | 460 |     |     | 470 |     |     | 480 |     |
| --- | --- | --- | --- | --- | --- | --- | --- | --- | --- | --- | --- | --- | --- | --- |
| AAG | GGC | CCA | TCG | GTC | TTC | CCC | CTG | GCA | CCC | TCC | TCC | AAG | AGC | ACC | TCT |
| Lys | Gly | Pro | Ser | Val | Phe | Pro | Leu | Ala | Pro | Ser | Ser | Lys | Ser | Thr | Ser> |

|     | 490 |     |     | 500 |     |     | 510 |     |     | 520 |     |     | 530 |     |
| --- | --- | --- | --- | --- | --- | --- | --- | --- | --- | --- | --- | --- | --- | --- |
| GGG | GGC | ACA | GCG | GCC | CTG | GGC | TGC | CTG | GTC | AAG | GAC | TAC | TTC | CCC | GAA |
| Gly | Gly | Thr | Ala | Ala | Leu | Gly | Cys | Leu | Val | Lys | Asp | Tyr | Phe | Pro | Glu> |

|     | 540 |     |     | 550 |     |     | 560 |     |     | 570 |     |     | 580 |     |
| --- | --- | --- | --- | --- | --- | --- | --- | --- | --- | --- | --- | --- | --- | --- |
| CCG | GTG | ACG | GTG | TCG | TGG | AAC | TCA | GGC | GCC | CTG | ACC | AGC | GGC | GTG | CAC |
| Pro | Val | Thr | Val | Ser | Trp | Asn | Ser | Gly | Ala | Leu | Thr | Ser | Gly | Val | His> |

|     | 590 |     |     | 600 |     |     | 610 |     |     | 620 |     |     |     |     |
| --- | --- | --- | --- | --- | --- | --- | --- | --- | --- | --- | --- | --- | --- | --- |
| ACC | TTC | CCG | GCT | GTC | CTA | CAG | TCC | TCA | GGA | CTC | TAC | TCC | CTC | AGC | AGC |
| Thr | Phe | Pro | Ala | Val | Leu | Gln | Ser | Ser | Gly | Leu | Tyr | Ser | Leu | Ser | Ser> |

| 630 |     |     | 640 |     |     | 650 |     |     | 660 |     |     | 670 |     |     |     |
| --- | --- | --- | --- | --- | --- | --- | --- | --- | --- | --- | --- | --- | --- | --- | --- |
| GTG | GTG | ACC | GTG | CCC | TCC | AGC | AGC | TTG | GGC | ACC | CAG | ACC | TAC | ATC | TGC |
| Val | Val | Thr | Val | Pro | Ser | Ser | Ser | Leu | Gly | Thr | Gln | Thr | Tyr | Ile | Cys> |

| 680 |     |     | 690 |     |     | 700 |     |     | 710 |     |     | 720 |     |     |     |
| --- | --- | --- | --- | --- | --- | --- | --- | --- | --- | --- | --- | --- | --- | --- | --- |
| AAC | GTG | AAT | CAC | AAG | CCC | AGC | AAC | ACC | AAG | GTG | GAC | AAG | AAA | GTT | GAG |
| Asn | Val | Asn | His | Lys | Pro | Ser | Asn | Thr | Lys | Val | Asp | Lys | Lys | Val | Glu> |

|     | 730 |     |     | 740 |     |     | 750 |     |     | 760 |     |     | 770 |     |
| --- | --- | --- | --- | --- | --- | --- | --- | --- | --- | --- | --- | --- | --- | --- | --- |
| CCC | AAA | TCT | TGT | GAC | AAA | ACT | CAC | ACA | TGC | CCA | CCG | TGC | CCA | GCA | CCT |
| Pro | Lys | Ser | Cys | Asp | Lys | Thr | His | Thr | Cys | Pro | Pro | Cys | Pro | Ala | Pro> |

|     | 780 |     |     | 790 |     |     | 800 |     |     | 810 |     |     | 820 |     |
| --- | --- | --- | --- | --- | --- | --- | --- | --- | --- | --- | --- | --- | --- | --- | --- |
| GAA | CTC | CTG | GGG | GGA | CCG | TCA | GTC | TTC | CTC | TTC | CCC | CCA | AAA | CCC | AAG |
| Glu | Leu | Leu | Gly | Gly | Pro | Ser | Val | Phe | Leu | Phe | Pro | Pro | Lys | Pro | Lys> |

|     | 830 |     |     | 840 |     |     | 850 |     |     | 860 |     |     |     |     |
| --- | --- | --- | --- | --- | --- | --- | --- | --- | --- | --- | --- | --- | --- | --- | --- |
| GAC | ACC | CTC | ATG | ATC | TCC | CGG | ACC | CCT | GAG | GTC | ACA | TGC | GTG | GTG | GTG |
| Asp | Thr | Leu | Met | Ile | Ser | Arg | Thr | Pro | Glu | Val | Thr | Cys | Val | Val | Val> |

| 870 |     |     | 880 |     |     | 890 |     |     | 900 |     |     | 910 |     |     |     |
| --- | --- | --- | --- | --- | --- | --- | --- | --- | --- | --- | --- | --- | --- | --- | --- |
| GAC | GTG | AGC | CAC | GAA | GAC | CCT | GAG | GTC | AAG | TTC | AAC | TGG | TAC | GTG | GAC |
| Asp | Val | Ser | His | Glu | Asp | Pro | Glu | Val | Lys | Phe | Asn | Trp | Tyr | Val | Asp> |

FIG. 16 cont.

```
      920              930              940              950              960
GGC  GTG  GAG  GTG  CAT  AAT  GCC  AAG  ACA  AAG  CCG  CGG  GAG  GAG  CAG  TAC
Gly  Val  Glu  Val  His  Asn  Ala  Lys  Thr  Lys  Pro  Arg  Glu  Glu  Gln  Tyr>
      970              980              990             1000             1010
AAC  AGC  ACG  TAC  CGT  GTG  GTC  AGC  GTC  CTC  ACC  GTC  CTG  CAC  CAG  GAC
Asn  Ser  Thr  Tyr  Arg  Val  Val  Ser  Val  Leu  Thr  Val  Leu  His  Gln  Asp>
     1020             1030             1040             1050             1060
TGG  CTG  AAT  GGC  AAG  GAG  TAC  AAG  TGC  AAG  GTC  TCC  AAC  AAA  GCC  CTC
Trp  Leu  Asn  Gly  Lys  Glu  Tyr  Lys  Cys  Lys  Val  Ser  Asn  Lys  Ala  Leu>
          1070             1080             1090             1100
CCA  GCC  CCC  ATC  GAG  AAA  ACC  ATC  TCC  AAA  GCC  AAA  GGG  CAG  CCC  CGA
Pro  Ala  Pro  Ile  Glu  Lys  Thr  Ile  Ser  Lys  Ala  Lys  Gly  Gln  Pro  Arg>
1110           1120             1130             1140             1150
GAA  CCA  CAG  GTG  TAC  ACC  CTG  CCC  CCA  TCC  CGG  GAT  GAG  CTG  ACC  AAG
Glu  Pro  Gln  Val  Tyr  Thr  Leu  Pro  Pro  Ser  Arg  Asp  Glu  Leu  Thr  Lys>
1160             1170             1180             1190             1200
AAC  CAG  GTC  AGC  CTG  ACC  TGC  CTG  GTC  AAA  GGC  TTC  TAT  CCC  AGC  GAC
Asn  Gln  Val  Ser  Leu  Thr  Cys  Leu  Val  Lys  Gly  Phe  Tyr  Pro  Ser  Asp>
     1210             1220             1230             1240             1250
ATC  GCC  GTG  GAG  TGG  GAG  AGC  AAT  GGG  CAG  CCG  GAG  AAC  AAC  TAC  AAG
Ile  Ala  Val  Glu  Trp  Glu  Ser  Asn  Gly  Gln  Pro  Glu  Asn  Asn  Tyr  Lys>
          1260             1270             1280             1290             1300
ACC  ACG  CCT  CCC  GTG  CTG  GAC  TCC  GAC  GGC  TCC  TTC  TTC  CTC  TAC  AGC
Thr  Thr  Pro  Pro  Val  Leu  Asp  Ser  Asp  Gly  Ser  Phe  Phe  Leu  Tyr  Ser>
          1310             1320             1330             1340
AAG  CTC  ACC  GTG  GAC  AAG  AGC  AGG  TGG  CAG  CAG  GGG  AAC  GTC  TTC  TCA
Lys  Leu  Thr  Val  Asp  Lys  Ser  Arg  Trp  Gln  Gln  Gly  Asn  Val  Phe  Ser>
1350             1360             1370             1380             1390
TGC  TCC  GTG  ATG  CAT  GAG  GCT  CTG  CAC  AAC  CAC  TAC  ACG  CAG  AAG  AGC
Cys  Ser  Val  Met  His  Glu  Ala  Leu  His  Asn  His  Tyr  Thr  Gln  Lys  Ser>
1400             1410
CTC  TCC  CTG  TCT  CCG  GGT  AAA
Leu  Ser  Leu  Ser  Pro  Gly  Lys>
```

FIG. 16 cont.

FIG. 17.

Humanised 323/A3 (IgG4cys) heavy chain cDNA sequence)
SEQ ID NOs: 6 and 7

```
            10            20                    30              40              50
CGTAAGCTTC     ACAGATCCTC     ACC  ATG  GGA  TGG  AGC  TGT  ATC  ATC  CTC  TTT  CTG
                                   Met  Gly  Trp  Ser  Cys  Ile  Ile  Leu  Phe  Leu>

60             70              80             90             100
GTG  GCA  ACA  GCT  ACA  GGT  GTC  CAC  TCC  CAG  GTA  CAG  CTA  GTG  CAA  TCA
Val  Ala  Thr  Ala  Thr  Gly  Val  His  Ser  Xaa> Val  Gln  Leu  Val  Gln  Ser>
                                           Gln 110            120            130            140
GGG  CCT  GAA  GTG  AAG  AAG  CCT  GGG  GCC  TCA  GTG  AAA  GTT  TCC  TGC  AAG
Gly  Pro  Glu  Val  Lys  Lys  Pro  Gly  Ala  Ser  Val  Lys  Val  Ser  Cys  Lys>

150            160            170            180            190
GCT  TCT  GGC  TAC  ACC  TTC  ACC  AAC  TAT  GGA  ATG  AAC  TGG  GTA  AGG  CAG
Ala  Ser  Gly  Tyr  Thr  Phe  Thr  Asn  Tyr  Gly  Met  Asn  Trp  Val  Arg  Gln>

200            210            220            230            240
GCG  CCT  GGA  CAG  GGG  CTT  GAG  TGG  ATG  GGG  TGG  ATA  AAC  ACC  TAC  ACT
Ala  Pro  Gly  Gln  Gly  Leu  Glu  Trp  Met  Gly  Trp  Ile  Asn  Thr  Tyr  Thr>

250            260            270            280            290
GGA  GAG  CCA  ACA  TAT  GGT  GAA  GAT  TTC  AAG  GGA  CGG  TTT  GCA  TTC  TCT
Gly  Glu  Pro  Thr  Tyr  Gly  Glu  Asp  Phe  Lys  Gly  Arg  Phe  Ala  Phe  Ser>

300            310            320            330            340
CTA  GAC  ACA  TCC  GCC  AGC  ACA  GCC  TAT  ATG  GAG  CTC  AGC  TCG  CTG  AGA
Leu  Asp  Thr  Ser  Ala  Ser  Thr  Ala  Tyr  Met  Glu  Leu  Ser  Ser  Leu  Arg>

350            360            370            380
TCC  GAG  GAC  ACT  GCA  GTC  TAT  TTC  TGT  GCG  AGA  TTT  GGT  AAC  TAC  GTA
Ser  Glu  Asp  Thr  Ala  Val  Tyr  Phe  Cys  Ala  Arg  Phe  Gly  Asn  Tyr  Val>

390            400            410            420            430
GAC  TAC  TGG  GGT  CAA  GGA  TCA  CTA  GTC  ACT  GTC  TCC  TCA  GCT  TCC  ACC
Asp  Tyr  Trp  Gly  Gln  Gly  Ser  Leu  Val  Thr  Val  Ser  Ser> Ala  Ser  Thr>

440            450            460            470            480
AAG  GGC  CCA  TCC  GTC  TTC  CCC  CTG  GCG  CCC  TGC  TCC  AGG  AGC  ACC  TCC
Lys  Gly  Pro  Ser  Val  Phe  Pro  Leu  Ala  Pro  Cys  Ser  Arg  Ser  Thr  Ser>
```

```
       490              500              510              520              530
GAG  AGC  ACA  GCC  GCC  CTG  GGC  TGC  CTG  GTC  AAG  GAC  TAC  TTC  CCC  GAA
Glu  Ser  Thr  Ala  Ala  Leu  Gly  Cys  Leu  Val  Lys  Asp  Tyr  Phe  Pro  Glu>

540              550              560              570         580
CCG  GTG  ACG  GTG  TCG  TGG  AAC  TCA  GGC  GCC  CTG  ACC  AGC  GGC  GTG  CAC
Pro  Val  Thr  Val  Ser  Trp  Asn  Ser  Gly  Ala  Leu  Thr  Ser  Gly  Val  His>

590              600              610         620
ACC  TTC  CCG  GCT  GTC  CTA  CAG  TCC  TCA  GGA  CTC  TAC  TCC  CTC  AGC  AGC
Thr  Phe  Pro  Ala  Val  Leu  Gln  Ser  Ser  Gly  Leu  Tyr  Ser  Leu  Ser  Ser>

630              640              650              660              670
GTG  GTG  ACC  GTG  CCC  TCC  AGC  AGC  TTG  GGC  ACG  AAG  ACC  TAC  ACC  TGC
Val  Val  Thr  Val  Pro  Ser  Ser  Ser  Leu  Gly  Thr  Lys  Thr  Tyr  Thr  Cys>

680              690              700              710              720
AAC  GTA  GAT  CAC  AAG  CCC  AGC  AAC  ACC  AAG  GTG  GAC  AAG  AGA  GTT  GAG
Asn  Val  Asp  His  Lys  Pro  Ser  Asn  Thr  Lys  Val  Asp  Lys  Arg  Val  Glu>

730              740              750              760         770
TCC  AAA  TAT  GGT  CCC  CCA  TGC  CCA  CCG  TGC  CCT  GCA  CCT  GAG  TTC  GCG
Ser  Lys  Tyr  Gly  Pro  Pro  Cys  Pro  Pro  Cys  Pro  Ala  Pro  Glu  Phe  Ala>

780              790              800              810         820
GGG  GCA  CCA  TCA  GTC  TTC  CTG  TTC  CCC  CCA  AAA  CCC  AAG  GAC  ACT  CTC
Gly  Ala  Pro  Ser  Val  Phe  Leu  Phe  Pro  Pro  Lys  Pro  Lys  Asp  Thr  Leu>

830              840              850              860
ATG  ATC  TCC  CGG  ACC  CCT  GAG  GTC  ACG  TGC  GTG  GTG  GTG  GAC  GTG  AGC
Met  Ile  Ser  Arg  Thr  Pro  Glu  Val  Thr  Cys  Val  Val  Val  Asp  Val  Ser>

870         880              890              900              910
CAG  GAA  GAC  CCC  GAG  GTC  CAG  TTC  AAC  TGG  TAC  GTG  GAT  GGC  GTG  GAG
Gln  Glu  Asp  Pro  Glu  Val  Gln  Phe  Asn  Trp  Tyr  Val  Asp  Gly  Val  Glu>

920              930              940              950         960
GTG  CAT  AAT  GCC  AAG  ACA  AAG  CCG  CGG  GAG  GAG  CAG  TTC  AAC  AGC  ACG
Val  His  Asn  Ala  Lys  Thr  Lys  Pro  Arg  Glu  Glu  Gln  Phe  Asn  Ser  Thr>
```

FIG. 17cont.

```
        970             980             990            1000            1010
  TAC  CGT  GTG  GTC  AGC  GTC  CTC  ACC  GTC  CTG  CAC  CAG  GAC  TGG  CTG  ACC
  Tyr  Arg  Val  Val  Ser  Val  Leu  Thr  Val  Leu  His  Gln  Asp  Trp  Leu  Asn>

1020            1030            1040            1050            1060
  GGC  AAG  GCG  TAC  AAG  TGC  AAG  GTC  TCC  AAC  AAA  GGC  CTC  CCG  TCC  TCC
  Gly  Lys  Ala  Tyr  Lys  Cys  Lys  Val  Ser  Asn  Lys  Gly  Leu  Pro  Ser  Ser>

1070            1080            1090            1100
  ATC  GAG  AAA  ACC  ATC  TCC  AAA  GCC  AAA  GGG  CAG  CCC  CGA  GAG  CCA  CAG
  Ile  Glu  Lys  Thr  Ile  Ser  Lys  Ala  Lys  Gly  Gln  Pro  Arg  Glu  Pro  Gln>

1110            1120            1130            1140            1150
  GTG  TAC  ACC  CTG  CCC  CCA  TCC  CAG  GAG  GAG  ATG  ACC  AAG  AAC  CAG  GTC
  Val  Tyr  Thr  Leu  Pro  Pro  Ser  Gln  Glu  Glu  Met  Thr  Lys  Asn  Gln  Val>

1160            1170            1180            1190            1200
  AGC  CTG  ACC  TGC  CTG  GTC  AAA  GGC  TTC  TAC  CCC  AGC  GAC  ATC  GCC  GTG
  Ser  Leu  Thr  Cys  Leu  Val  Lys  Gly  Phe  Tyr  Pro  Ser  Asp  Ile  Ala  Val>

1210            1220            1230            1240            1250
  GAG  TGG  GAG  AGC  AAT  GGG  CAG  CCG  GAG  AAC  AAC  TAC  AAG  ACC  ACG  CCT
  Glu  Trp  Glu  Ser  Asn  Gly  Gln  Pro  Glu  Asn  Asn  Tyr  Lys  Thr  Thr  Pro>

1260            1270            1280            1290            1300
  CCC  GTG  CTG  GAC  TCC  GAC  GGC  TCC  TTC  TTC  CTC  TAC  AGC  AGG  CTA  ACC
  Pro  Val  Leu  Asp  Ser  Asp  Gly  Ser  Phe  Phe  Leu  Tyr  Ser  Arg  Leu  Thr>

1310            1320            1330            1340
  GTG  GAC  AAG  AGC  AGG  TGG  CAG  GAG  GGG  AAT  GTC  TTC  TCA  TGC  TCC  GTG
  Val  Asp  Lys  Ser  Arg  Trp  Gln  Glu  Gly  Asn  Val  Phe  Ser  Cys  Ser  Val>

1350            1360            1370            1380            1390
  ATG  CAT  GAG  GCT  CTG  CAC  AAC  CAC  TAC  ACA  CAG  AAG  AGC  CTC  TGC  CTG
  Met  His  Glu  Ala  Leu  His  Asn  His  Tyr  Thr  Gln  Lys  Ser  Leu  Cys  Leu>

1400            1410
  TCT  CTG  GGT  AAA  T    GAGAATTC
  Ser  Leu  Gly  Lys>
```

FIG. 17cont.

FIG. 18.

Humanised 323/A3 (IgG$_{2cys}$) heavy chain cDNA sequence

SEQ ID NOs: 8, 9 and 10

```
          10             20              30             40              50             60
          .              .               .              .               .              .
  ATGGATTGGC      TGTGGAACTT       GCTATTCCTG     ATGGCAGCTG      CCCAAAGTAT     CCAAGCA    CAG
  TACCTAACCG      ACACCTTGAA       CGATAAGGAC     TACCGTCGAC      GGGTTTCATA     GGTTCGT    GTC
                                                                                            Gln>

70                    80                    90                   100
              .                     .                     .                    .
  ATC   CAG   TTG   GTG   CAG   TCT   GGA   CCT   GAA   CTG   AAG   AAG   CCT   GGA   GAG   ACA
  TAG   GTC   AAC   CAC   GTC   AGA   CCT   GGA   CTT   GAC   TTC   TTC   GGA   CCT   CTC   TGT
  Ile   Gln   Leu   Val   Gln   Ser   Gly   Pro   Glu   Leu   Lys   Lys   Pro   Gly   Glu   Thr>

110               120                   130                  140                  150
   .                 .                     .                    .                    .
  GTC   AAG   ATC   TCC   TGC   AAG   GCT   TCT   GGA   TAT   ACC   TTC   ACA   AAC   TAT   GGA
  CAG   TTC   TAG   AGG   ACG   TTC   CGA   AGA   CCT   ATA   TGG   AAG   TGT   TTG   ATA   CCT
  Val   Lys   Ile   Ser   Cys   Lys   Ala   Ser   Gly   Tyr   Thr   Phe   Thr   Asn   Tyr   Gly>

160                   170                   180                  190                  200
        .                     .                     .                    .                    .
  ATG   AAC   TGG   GTG   AGG   CAG   GCT   TCA   GGA   GAG   GGT   TTA   AAG   TGG   ATG   GGC
  TAC   TTG   ACC   CAC   TCC   GTC   CGA   AGT   CCT   CTC   CCA   AAT   TTC   ACC   TAC   CCG
  Met   Asn   Trp   Val   Arg   Gln   Ala   Ser   Gly   Glu   Gly   Leu   Lys   Trp   Met   Gly>

210                   220                  230                   240                  250
           .                     .                    .                     .                    .
  TGG   ATA   AAC   ACC   TAC   ACT   GGA   GAG   CCA   ACA   TAT   GGT   GAA   GAT   TTC   AAG
  ACC   TAT   TTG   TGG   ATG   TGA   CCT   CTC   GGT   TGT   ATA   CCA   CTT   CTA   AAG   TTC
  Trp   Ile   Asn   Thr   Tyr   Thr   Gly   Glu   Pro   Thr   Tyr   Gly   Glu   Asp   Phe   Lys>

260                   270                  280                   290                  300
               .                     .                    .                     .                    .
  GGA   CGG   TTT   GCC   TTC   TCT   TTG   GAA   ACC   TCT   GCC   AGC   ACT   GCC   TAT   TTG
  CCT   GCC   AAA   CGG   AAG   AGA   AAC   CTT   TGG   AGA   CGG   TCG   TGA   CGG   ATA   AAC
  Gly   Arg   Phe   Ala   Phe   Ser   Leu   Glu   Thr   Ser   Ala   Ser   Thr   Ala   Tyr   Leu>

310                   320                  330                   340
               .                     .                    .                     .
  CAG   ATC   AAC   AAC   CTC   AAA   AAT   GAA   GAC   ACG   GCT   ACA   TAT   TTC   TGT   GCA
  GTC   TAG   TTG   TTG   GAG   TTT   TTA   CTT   CTG   TGC   CGA   TGT   ATA   AAG   ACA   CGT
  Gln   Ile   Asn   Asn   Leu   Lys   Asn   Glu   Asp   Thr   Ala   Thr   Tyr   Phe   Cys   Ala>

350                   360                   370                  380                   390
   .                     .                     .                    .                     .
  AGA   TTT   GGT   AAC   TAC   GTA   GAC   TAC   TGG   GGC   CAA   GGC   ACC   ACT   CTC   ACA
  TCT   AAA   CCA   TTG   ATG   CAT   CTG   ATG   ACC   CCG   GTT   CCG   TGG   TGA   GAG   TGT
  Arg   Phe   Gly   Asn   Tyr   Val   Asp   Tyr   Trp   Gly   Gln   Gly   Thr   Thr   Leu   Thr>

400                   410                  420                   430                  440
           .                     .                    .                     .                    .
  GTC   TCC   TCA   GCC   TCC   ACC   AAG   GGC   CCA   TCG   GTC   TTC   CCC   CTG   GCG   CCC
  CAG   AGG   AGT   CGG   AGG   TGG   TTC   CCG   GGT   AGC   CAG   AAG   GGG   GAC   CGC   GGG
  Val   Ser   Ser>
                    Ala   Ser   Thr   Lys   Gly   Pro   Ser   Val   Phe   Pro   Leu   Ala   Pro>
```

```
         450                    460                    470                    480                    490
     •    •                 •    •                 •    •                 •    •                 •    •
TGC  TCC  AGG  AGC  ACC  TCC  GAG  AGC  ACA  GCG  GCC  CTG  GGC  TGC  CTG  GTC
ACG  AGG  TCC  TCG  TGG  AGG  CTC  TCG  TGT  CGC  CGG  GAC  CCG  ACG  GAC  CAG
Cys  Ser  Arg  Ser  Thr  Ser  Glu  Ser  Thr  Ala  Ala  Leu  Gly  Cys  Leu  Val>

500                    510                    520                    530              540
          •    •                 •    •                 •    •                 •    •            •    •
AAG  GAC  TAC  TTC  CCC  GAA  CCG  GTG  ACG  GTG  TCG  TGG  AAC  TCA  GGC  GCT
TTC  CTG  ATG  AAG  GGG  CTT  GGC  CAC  TGC  CAC  AGC  ACC  TTG  AGT  CCG  CGA
Lys  Asp  Tyr  Phe  Pro  Glu  Pro  Val  Thr  Val  Ser  Trp  Asn  Ser  Gly  Ala>

550             .      560                    570                    580
          •    •            •                        •    •                 •    •            •
CTG  ACC  AGC  GGC  GTG  CAC  ACC  TTC  CCA  GCT  GTC  CTA  CAG  TCC  TCA  GGA
GAC  TGG  TCG  CCG  CAC  GTG  TGG  AAG  GGT  CGA  CAG  GAT  GTC  AGG  AGT  CCT
Leu  Thr  Ser  Gly  Val  His  Thr  Phe  Pro  Ala  Val  Leu  Gln  Ser  Ser  Gly>

590                    600                    610                    620                630
  •    •                 •    •                 •    •                 •    •             •    •
CTC  TAC  TCC  CTC  AGC  AGC  GTG  GTG  ACC  GTG  CCC  TCC  AGC  AAC  TTC  GGC
GAG  ATG  AGG  GAG  TCG  TCG  CAC  CAC  TGG  CAC  GGG  AGG  TCG  TTG  AAG  CCG
Leu  Tyr  Ser  Leu  Ser  Ser  Val  Val  Thr  Val  Pro  Ser  Ser  Asn  Phe  Gly>

640                    650                    660                   670                     680
     •    •                 •    •                 •    •                •    •                  •    •
ACC  CAG  ACC  TAC  ACC  TGC  AAC  GTA  GAT  CAC  AAG  CCC  AGC  AAC  ACC  AAG
TGG  GTC  TGG  ATG  TGG  ACG  TTG  CAT  CTA  GTG  TTC  GGG  TCG  TTG  TGG  TTC
Thr  Gln  Thr  Tyr  Thr  Cys  Asn  Val  Asp  His  Lys  Pro  Ser  Asn  Thr  Lys>

690                    700                    710                    720                 730
          •    •                 •    •                 •    •                 •    •             •    •
GTG  GAC  AAG  ACA  GTT  GAG  CGC  AAA  TGT  TGT  GTC  GAG  TGC  CCA  CCG  TGC
CAC  CTG  TTC  TGT  CAA  CTC  GCG  TTT  ACA  ACA  CAG  CTC  ACG  GGT  GGC  ACG
Val  Asp  Lys  Thr  Val  Glu  Arg  Lys  Cys  Cys  Val  Glu  Cys  Pro  Pro  Cys>

•    740              •    750                    760                    770             780
                             •                        •    •                 •    •             •    •
CCA  GCA  CCA  CCT  GTG  GCA  GGA  CCG  TCA  GTC  TTC  CTC  TTC  CCC  CCA  AAA
GGT  CGT  GGT  GGA  CAC  CGT  CCT  GGC  AGT  CAG  AAG  GAG  AAG  GGG  GGT  TTT
Pro  Ala  Pro  Pro  Val  Ala  Gly  Pro  Ser  Val  Phe  Leu  Phe  Pro  Pro  Lys>

790                    800                    810                    820
          •    •            •                   •     •                 •    •             •    •
CCC  AAG  GAC  ACC  CTC  ATG  ATC  TCC  CGG  ACC  CCT  GAG  GTC  ACG  TGC  GTG
GGG  TTC  CTG  TGG  GAG  TAC  TAG  AGG  GCC  TGG  GGA  CTC  CAG  TGC  ACG  CAC
Pro  Lys  Asp  Thr  Leu  Met  Ile  Ser  Arg  Thr  Pro  Glu  Val  Thr  Cys  Val>

830                    840                    850                    860                    870
  •    •            •    •                 •    •                 •    •                 •    •
GTG  GTG  GAC  GTG  AGC  CAC  GAA  GAC  CCC  GAG  GTC  CAG  TTC  AAC  TGG  TAC
CAC  CAC  CTG  CAC  TCG  GTG  CTT  CTG  GGG  CTC  CAG  GTC  AAG  TTG  ACC  ATG
Val  Val  Asp  Val  Ser  His  Glu  Asp  Pro  Glu  Val  Gln  Phe  Asn  Trp  Tyr>
```

FIG. 18 cont.

|     | 880 |     |     |     | 890 |     |     |     | 900 |     |     |     | 910 |     |     |     | 920 |     |
| --- | --- | --- | --- | --- | --- | --- | --- | --- | --- | --- | --- | --- | --- | --- | --- | --- | --- | --- |
| GTG | GAC | GGC | GTG | GAG | GTG | CAT | AAT | GCC | AAG | ACA | AAG | CCA | CGG | GAG | GAG |
| CAC | CTG | CCG | CAC | CTC | CAC | GTA | TTA | CGG | TTC | TGT | TTC | GGT | GCC | CTC | CTC |
| Val | Asp | Gly | Val | Glu | Val | His | Asn | Ala | Lys | Thr | Lys | Pro | Arg | Glu | Glu> |

|     | 930 |     |     |     | 940 |     |     |     | 950 |     |     |     | 960 |     |     |     | 970 |
| --- | --- | --- | --- | --- | --- | --- | --- | --- | --- | --- | --- | --- | --- | --- | --- | --- | --- |
| CAG | TTC | AAC | AGC | ACG | TTC | CGT | GTG | GTC | AGC | GTC | CTC | ACC | GTT | GTG | CAC |
| GTC | AAG | TTG | TCG | TGC | AAG | GCA | CAC | CAG | TCG | CAG | GAG | TGG | CAA | CAC | GTG |
| Gln | Phe | Asn | Ser | Thr | Phe | Arg | Val | Val | Ser | Val | Leu | Thr | Val | Val | His> |

|     | 980 |     |     |     | 990 |     |     |     | 1000 |     |     |     | 1010 |     |     |     | 1020 |
| --- | --- | --- | --- | --- | --- | --- | --- | --- | --- | --- | --- | --- | --- | --- | --- | --- | --- |
| CAG | GAC | TGG | CTG | AAC | GGC | AAG | GAG | TAC | AAG | TGC | AAG | GTC | TCC | AAC | AAA |
| GTC | CTG | ACC | GAC | TTG | CCG | TTC | CTC | ATG | TTC | ACG | TTC | CAG | AGG | TTG | TTT |
| Gln | Asp | Trp | Leu | Asn | Gly | Lys | Glu | Tyr | Lys | Cys | Lys | Val | Ser | Asn | Lys> |

|     | 1030 |     |     |     | 1040 |     |     |     | 1050 |     |     |     | 1060 |     |     |
| --- | --- | --- | --- | --- | --- | --- | --- | --- | --- | --- | --- | --- | --- | --- | --- |
| GGC | CTC | CCA | GCC | CCC | ATC | GAG | AAA | ACC | ATC | TCC | AAA | ACC | AAA | GGG | CAG |
| CCG | GAG | GGT | CGG | GGG | TAG | CTC | TTT | TGG | TAG | AGG | TTT | TGG | TTT | CCC | GTC |
| Gly | Leu | Pro | Ala | Pro | Ile | Glu | Lys | Thr | Ile | Ser | Lys | Thr | Lys | Gly | Gln> |

| 1070 |     |     |     | 1080 |     |     |     | 1090 |     |     |     | 1100 |     |     |     | 1110 |     |     |
| --- | --- | --- | --- | --- | --- | --- | --- | --- | --- | --- | --- | --- | --- | --- | --- | --- | --- | --- |
| CCC | CGA | GAA | CCA | CAG | GTG | TAC | ACC | CTG | CCC | CCA | TCC | CGG | GAG | GAG | ATG |
| GGG | GCT | CTT | GGT | GTC | CAC | ATG | TGG | GAC | GGG | GGT | AGG | GCC | CTC | CTC | TAC |
| Pro | Arg | Glu | Pro | Gln | Val | Tyr | Thr | Leu | Pro | Pro | Ser | Arg | Glu | Glu | Met> |

| 1120 |     |     |     | 1130 |     |     |     | 1140 |     |     |     | 1150 |     |     |     | 1160 |     |     |
| --- | --- | --- | --- | --- | --- | --- | --- | --- | --- | --- | --- | --- | --- | --- | --- | --- | --- | --- |
| ACC | AAG | AAC | CAG | GTC | AGC | CTG | ACC | TGC | CTG | GTC | AAA | GGC | TTC | TAC | CCC |
| TGG | TTC | TTG | GTC | CAG | TCG | GAC | TGG | ACG | GAC | CAG | TTT | CCG | AAG | ATG | GGG |
| Thr | Lys | Asn | Gln | Val | Ser | Leu | Thr | Cys | Leu | Val | Lys | Gly | Phe | Tyr | Pro> |

|     | 1170 |     |     |     | 1180 |     |     |     | 1190 |     |     |     | 1200 |     |     |     | 1210 |
| --- | --- | --- | --- | --- | --- | --- | --- | --- | --- | --- | --- | --- | --- | --- | --- | --- | --- |
| AGC | GAC | ATC | GCC | GTG | GAG | TGG | GAG | AGC | AAT | GGG | CAG | CCG | GAG | AAC | AAC |
| TCG | CTG | TAG | CGG | CAC | CTC | ACC | CTC | TCG | TTA | CCC | GTC | GGC | CTC | TTG | TTG |
| Ser | Asp | Ile | Ala | Val | Glu | Trp | Glu | Ser | Asn | Gly | Gln | Pro | Glu | Asn | Asn> |

|     | 1220 |     |     |     | 1230 |     |     |     | 1240 |     |     |     | 1250 |     |     |     | 1260 |
| --- | --- | --- | --- | --- | --- | --- | --- | --- | --- | --- | --- | --- | --- | --- | --- | --- | --- |
| TAC | AAG | ACC | ACA | CCT | CCC | ATG | CTG | GAC | TCC | GAC | GGC | TCC | TTC | TTC | CTC |
| ATG | TTC | TGG | TGT | GGA | GGG | TAC | GAC | CTG | AGG | CTG | CCG | AGG | AAG | AAG | GAG |
| Tyr | Lys | Thr | Thr | Pro | Pro | Met | Leu | Asp | Ser | Asp | Gly | Ser | Phe | Phe | Leu> |

FIG. 18 cont.

```
        1270            1280            1290            1300
TAC AGC AAG CTC ACC GTG GAC AAG AGC AGG TGG CAG CAG GGG AAC GTC
ATG TCG TTC GAG TGG CAC CTG TTC TCG TCC ACC GTC GTC CCC TTG CAG
Tyr Ser Lys Leu Thr Val Asp Lys Ser Arg Trp Gln Gln Gly Asn Val>

1310            1320            1330            1340            1350
TTC TCA TGC TCC GTG ATG CAT GAG GCT CTG CAC AAC CAC TAC ACA CAG
AAG AGT ACG AGG CAC TAC GTA CTC CGA GAC GTG TTG GTG ATG TGT GTC
Phe Ser Cys Ser Val Met His Glu Ala Leu His Asn His Tyr Thr Gln>

1360            1370            1380            1390
AAG AGC CTC TGC CTG TCT CTG GGT AAA TGAGAAT TC
TTC TCG GAG ACG GAC AGA GAC CCA TTT ACTCTTA AG
Lys Ser Leu Cys Leu Ser Leu Gly Lys>
```

FIG. 18cont.

SEQUENCE LISTING

```
<160> NUMBER OF SEQ ID NOS: 16

<210> SEQ ID NO 1
<211> LENGTH: 740
<212> TYPE: DNA
<213> ORGANISM: Artificial Sequence
<220> FEATURE:
<221> NAME/KEY: CDS
<222> LOCATION: (24)..(740)
<220> FEATURE:
<223> OTHER INFORMATION: Description of Artificial Sequence: Synthetic
      sequence

<400> SEQUENCE: 1
cgtaagcttc acaggacctc acc atg gga tgg agc tgt atc atc ctc ttc ttg      53
                       Met Gly Trp Ser Cys Ile Ile Leu Phe Leu
                        1               5                  10 gta gca aca gct aca ggt gtc cac tcc gat att gtg atg act cag tct       101
Val Ala Thr Ala Thr Gly Val His Ser Asp Ile Val Met Thr Gln Ser
```

```
                15                  20                  25
cca ctc tcc ctg ccc gtc acc cct gga gag ccg gcc tcc atc tcc tgt    149
Pro Leu Ser Leu Pro Val Thr Pro Gly Glu Pro Ala Ser Ile Ser Cys
             30                  35                  40 agg tct agt aag aat ctc ctg cat agt aat ggc atc act tat ttg tat    197
Arg Ser Ser Lys Asn Leu Leu His Ser Asn Gly Ile Thr Tyr Leu Tyr
         45                  50                  55 tgg tac ctg cag aag cca ggg cag tct cca cag ctc ctg atc tat cag    245
Trp Tyr Leu Gln Lys Pro Gly Gln Ser Pro Gln Leu Leu Ile Tyr Gln
     60                  65                  70 atg tcc aac ctt gcc tca ggg gtc cct gac agg ttc agt agc agt gga    293
Met Ser Asn Leu Ala Ser Gly Val Pro Asp Arg Phe Ser Ser Ser Gly
 75                  80                  85                  90 tca ggc aca gat ttt aca ctg aaa atc agc aga gtg gag gct gag gat    341
Ser Gly Thr Asp Phe Thr Leu Lys Ile Ser Arg Val Glu Ala Glu Asp
                 95                 100                 105 gtt ggg gtt tat tac tgt gct caa aat cta gag att cct cgg acg ttc    389
Val Gly Val Tyr Tyr Cys Ala Gln Asn Leu Glu Ile Pro Arg Thr Phe
             110                 115                 120 ggc caa ggg acc aag gtg gag atc aaa cgt acg gtg gct gca cca tct    437
Gly Gln Gly Thr Lys Val Glu Ile Lys Arg Thr Val Ala Ala Pro Ser
         125                 130                 135 gtc ttc atc ttc ccg cca tct gat gag cag ttg aaa tct gga act gcc    485
Val Phe Ile Phe Pro Pro Ser Asp Glu Gln Leu Lys Ser Gly Thr Ala
     140                 145                 150 tct gtt gtg tgc ctg ctg aat aac ttc tat ccc aga gag gcc aaa gta    533
Ser Val Val Cys Leu Leu Asn Asn Phe Tyr Pro Arg Glu Ala Lys Val
155                 160                 165                 170 cag tgg aag gtg gat aac gcc ctc caa tcg ggt aac tcc cag gag agt    581
Gln Trp Lys Val Asp Asn Ala Leu Gln Ser Gly Asn Ser Gln Glu Ser
                175                 180                 185 gtc aca gag cag gac agc aag gac agc acc tac agc ctc agc agc acc    629
Val Thr Glu Gln Asp Ser Lys Asp Ser Thr Tyr Ser Leu Ser Ser Thr
            190                 195                 200 ctg acg ctg agc aaa gca gac tac gag aaa cac aaa gtc tac gcc tgc    677
Leu Thr Leu Ser Lys Ala Asp Tyr Glu Lys His Lys Val Tyr Ala Cys
        205                 210                 215 gaa gtc acc cat cag ggc ctg agc tcg ccc gtc aca aag agc ttc aac    725
Glu Val Thr His Gln Gly Leu Ser Ser Pro Val Thr Lys Ser Phe Asn
    220                 225                 230 agg gga gag tgt tag                                                740
Arg Gly Glu Cys
235

<210> SEQ ID NO 2
<211> LENGTH: 238
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 2

Met Gly Trp Ser Cys Ile Ile Leu Phe Leu Val Ala Thr Ala Thr Gly
  1               5                  10                  15

Val His Ser Asp Ile Val Met Thr Gln Ser Pro Leu Ser Leu Pro Val
                 20                  25                  30

Thr Pro Gly Glu Pro Ala Ser Ile Ser Cys Arg Ser Ser Lys Asn Leu
             35                  40                  45

Leu His Ser Asn Gly Ile Thr Tyr Leu Tyr Trp Tyr Leu Gln Lys Pro
```

```
                50                    55                    60
Gly Gln Ser Pro Gln Leu Leu Ile Tyr Gln Met Ser Asn Leu Ala Ser
 65                      70                      75                      80

Gly Val Pro Asp Arg Phe Ser Ser Gly Ser Gly Thr Asp Phe Thr
                     85                      90                      95

Leu Lys Ile Ser Arg Val Glu Ala Glu Asp Val Gly Val Tyr Tyr Cys
                100                     105                     110

Ala Gln Asn Leu Glu Ile Pro Arg Thr Phe Gly Gln Gly Thr Lys Val
                115                     120                     125

Glu Ile Lys Arg Thr Val Ala Ala Pro Ser Val Phe Ile Phe Pro Pro
130                     135                     140

Ser Asp Glu Gln Leu Lys Ser Gly Thr Ala Ser Val Val Cys Leu Leu
145                     150                     155                     160

Asn Asn Phe Tyr Pro Arg Glu Ala Lys Val Gln Trp Lys Val Asp Asn
                165                     170                     175

Ala Leu Gln Ser Gly Asn Ser Gln Glu Ser Val Thr Glu Gln Asp Ser
                180                     185                     190

Lys Asp Ser Thr Tyr Ser Leu Ser Ser Thr Leu Thr Leu Ser Lys Ala
                195                     200                     205

Asp Tyr Glu Lys His Lys Val Tyr Ala Cys Glu Val Thr His Gln Gly
210                     215                     220

Leu Ser Ser Pro Val Thr Lys Ser Phe Asn Arg Gly Glu Cys
225                     230                     235

<210> SEQ ID NO 3
<211> LENGTH: 740
<212> TYPE: DNA
<213> ORGANISM: Artificial Sequence
<220> FEATURE:
<223> OTHER INFORMATION: Description of Artificial Sequence: Synthetic
      sequence

<400> SEQUENCE: 3
ctaacactct cccctgttga agctctttgt gacgggcgag ctcaggccct gatgggtgac     60
ttcgcaggcg tagactttgt gtttctcgta gtctgctttg ctcagcgtca gggtgctgct    120
gaggctgtag gtgctgtcct tgctgtcctg ctctgtgaca ctctcctggg agttacccga    180
ttggagggcg ttatccacct tccactgtac tttggcctct ctgggataga agttattcag    240
caggcacaca acagaggcag ttccagattt caactgctca tcagatggcg ggaagatgaa    300
gacagatggt gcagccaccg tacgtttgat ctccaccttg gtcccttggc cgaacgtccg    360
aggaatctct agattttgag cacagtaata acccccaaca tcctcagcct ccactctgct    420
gattttcagt gtaaaatctg tgcctgatcc actgctactg aacctgtcag ggaccctga    480 ggcaaggttg acatctgat agatcaggag ctgtggagac tgccctggct tctgcaggta    540
ccaatacaaa taagtgatgc cattactatg caggagattc ttactagacc tacaggagat    600
ggaggccggc tctccagggg tgacgggcag ggagagtgga gactgagtca tcacaatatc    660
ggagtggaca cctgtagctg ttgctaccaa gaagaggatg atacagctcc atcccatggt    720
gaggtcctgt gaagcttacg                                                740

<210> SEQ ID NO 4
<211> LENGTH: 1418
<212> TYPE: DNA
<213> ORGANISM: Artificial Sequence
<220> FEATURE:
<221> NAME/KEY: CDS
```

<222> LOCATION: (24)..(1418)
<220> FEATURE:
<223> OTHER INFORMATION: Description of Artificial Sequence: Synthetic
      sequence

<400> SEQUENCE: 4

```
cgtaagcttc acagatcctc acc atg gga tgg agc tgt atc atc ctc ttt ctg      53
                         Met Gly Trp Ser Cys Ile Ile Leu Phe Leu
                          1               5                  10 gtg gca aca gct aca ggt gtc cac tcc cag gta cag cta gtg caa tca        101
Val Ala Thr Ala Thr Gly Val His Ser Gln Val Gln Leu Val Gln Ser
                 15                  20                  25 ggg cct gaa gtg aag aag cct ggg gcc tca gtg aaa gtt tcc tgc aag        149
Gly Pro Glu Val Lys Lys Pro Gly Ala Ser Val Lys Val Ser Cys Lys
             30                  35                  40 gct tct ggc tac acc ttc acc aac tat gga atg aac tgg gta agg cag        197
Ala Ser Gly Tyr Thr Phe Thr Asn Tyr Gly Met Asn Trp Val Arg Gln
         45                  50                  55 gcg cct gga cag ggg ctt gag tgg atg ggg tgg ata aac acc tac act        245
Ala Pro Gly Gln Gly Leu Glu Trp Met Gly Trp Ile Asn Thr Tyr Thr
     60                  65                  70 gga gag cca aca tat ggt gaa gat ttc aag gga cgg ttt gca ttc tct        293
Gly Glu Pro Thr Tyr Gly Glu Asp Phe Lys Gly Arg Phe Ala Phe Ser
 75                  80                  85                  90 cta gac aca tcc gcc agc aca gcc tat atg gag ctc agc tcg ctg aga        341
Leu Asp Thr Ser Ala Ser Thr Ala Tyr Met Glu Leu Ser Ser Leu Arg
                 95                 100                 105 tcc gag gac act gca gtc tat ttc tgt gcg aga ttt ggt aac tac gta        389
Ser Glu Asp Thr Ala Val Tyr Phe Cys Ala Arg Phe Gly Asn Tyr Val
            110                 115                 120 gac tac tgg ggt caa gga tca cta gtc act gtc tcc tca gcc tcc acc        437
Asp Tyr Trp Gly Gln Gly Ser Leu Val Thr Val Ser Ser Ala Ser Thr
        125                 130                 135 aag ggc cca tcg gtc ttc ccc ctg gca ccc tcc tcc aag agc acc tct        485
Lys Gly Pro Ser Val Phe Pro Leu Ala Pro Ser Ser Lys Ser Thr Ser
    140                 145                 150 ggg ggc aca gcg gcc ctg ggc tgc ctg gtc aag gac tac ttc ccc gaa        533
Gly Gly Thr Ala Ala Leu Gly Cys Leu Val Lys Asp Tyr Phe Pro Glu
155                 160                 165                 170 ccg gtg acg gtg tcg tgg aac tca ggc gcc ctg acc agc ggc gtg cac        581
Pro Val Thr Val Ser Trp Asn Ser Gly Ala Leu Thr Ser Gly Val His
                175                 180                 185 acc ttc ccg gct gtc cta cag tcc tca gga ctc tac tcc ctc agc agc        629
Thr Phe Pro Ala Val Leu Gln Ser Ser Gly Leu Tyr Ser Leu Ser Ser
            190                 195                 200 gtg gtg acc gtg ccc tcc agc agc ttg ggc acc cag acc tac atc tgc        677
Val Val Thr Val Pro Ser Ser Ser Leu Gly Thr Gln Thr Tyr Ile Cys
        205                 210                 215 aac gtg aat cac aag ccc agc aac acc aag gtg gac aag aaa gtt gag        725
Asn Val Asn His Lys Pro Ser Asn Thr Lys Val Asp Lys Lys Val Glu
    220                 225                 230 ccc aaa tct tgt gac aaa act cac aca tgc cca ccg tgc cca gca cct        773
Pro Lys Ser Cys Asp Lys Thr His Thr Cys Pro Pro Cys Pro Ala Pro
235                 240                 245                 250 gaa ctc ctg ggg gga ccg tca gtc ttc ctc ttc ccc cca aaa ccc aag        821
Glu Leu Leu Gly Gly Pro Ser Val Phe Leu Phe Pro Pro Lys Pro Lys
                255                 260                 265 gac acc ctc atg atc tcc cgg acc cct gag gtc aca tgc gtg gtg gtg        869
Asp Thr Leu Met Ile Ser Arg Thr Pro Glu Val Thr Cys Val Val Val
            270                 275                 280
```

-continued

```
gac gtg agc cac gaa gac cct gag gtc aag ttc aac tgg tac gtg gac        917
Asp Val Ser His Glu Asp Pro Glu Val Lys Phe Asn Trp Tyr Val Asp
        285                 290                 295 ggc gtg gag gtg cat aat gcc aag aca aag ccg cgg gag gag cag tac        965
Gly Val Glu Val His Asn Ala Lys Thr Lys Pro Arg Glu Glu Gln Tyr
300                 305                 310 aac agc acg tac cgt gtg gtc agc gtc ctc acc gtc ctg cac cag gac       1013
Asn Ser Thr Tyr Arg Val Val Ser Val Leu Thr Val Leu His Gln Asp
315                 320                 325                 330 tgg ctg aat ggc aag gag tac aag tgc aag gtc tcc aac aaa gcc ctc       1061
Trp Leu Asn Gly Lys Glu Tyr Lys Cys Lys Val Ser Asn Lys Ala Leu
                335                 340                 345 cca gcc ccc atc gag aaa acc atc tcc aaa gcc aaa ggg cag ccc cga       1109
Pro Ala Pro Ile Glu Lys Thr Ile Ser Lys Ala Lys Gly Gln Pro Arg
        350                 355                 360 gaa cca cag gtg tac acc ctg ccc cca tcc cgg gat gag ctg acc aag       1157
Glu Pro Gln Val Tyr Thr Leu Pro Pro Ser Arg Asp Glu Leu Thr Lys
365                 370                 375 aac cag gtc agc ctg acc tgc ctg gtc aaa ggc ttc tat ccc agc gac       1205
Asn Gln Val Ser Leu Thr Cys Leu Val Lys Gly Phe Tyr Pro Ser Asp
380                 385                 390 atc gcc gtg gag tgg gag agc aat ggg cag ccg gag aac aac tac aag       1253
Ile Ala Val Glu Trp Glu Ser Asn Gly Gln Pro Glu Asn Asn Tyr Lys
395                 400                 405                 410 acc acg cct ccc gtg ctg gac tcc gac ggc tcc ttc ttc ctc tac agc       1301
Thr Thr Pro Pro Val Leu Asp Ser Asp Gly Ser Phe Phe Leu Tyr Ser
                415                 420                 425 aag ctc acc gtg gac aag agc agg tgg cag cag ggg aac gtc ttc tca       1349
Lys Leu Thr Val Asp Lys Ser Arg Trp Gln Gln Gly Asn Val Phe Ser
        430                 435                 440 tgc tcc gtg atg cat gag gct ctg cac aac cac tac acg cag aag agc       1397
Cys Ser Val Met His Glu Ala Leu His Asn His Tyr Thr Gln Lys Ser
445                 450                 455 ctc tcc ctg tct ccg ggt aaa                                           1418
Leu Ser Leu Ser Pro Gly Lys
460                 465

<210> SEQ ID NO 5
<211> LENGTH: 465
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 5

Met Gly Trp Ser Cys Ile Ile Leu Phe Leu Val Ala Thr Ala Thr Gly
1               5                   10                  15

Val His Ser Gln Val Gln Leu Val Gln Ser Gly Pro Glu Val Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Glu Trp Met Gly Trp Ile Asn Thr Tyr Thr Gly Glu Pro Thr Tyr Gly
65                  70                  75                  80

Glu Asp Phe Lys Gly Arg Phe Ala Phe Ser Leu Asp Thr Ser Ala Ser
                85                  90                  95

Thr Ala Tyr Met Glu Leu Ser Ser Leu Arg Ser Glu Asp Thr Ala Val
            100                 105                 110
```

```
Tyr Phe Cys Ala Arg Phe Gly Asn Tyr Val Asp Tyr Trp Gly Gln Gly
            115                 120                 125
Ser Leu Val Thr Val Ser Ser Ala Ser Thr Lys Gly Pro Ser Val Phe
        130                 135                 140
Pro Leu Ala Pro Ser Ser Lys Ser Thr Ser Gly Gly Thr Ala Ala Leu
145                 150                 155                 160
Gly Cys Leu Val Lys Asp Tyr Phe Pro Glu Pro Val Thr Val Ser Trp
                165                 170                 175
Asn Ser Gly Ala Leu Thr Ser Gly Val His Thr Phe Pro Ala Val Leu
            180                 185                 190
Gln Ser Ser Gly Leu Tyr Ser Leu Ser Ser Val Val Thr Val Pro Ser
        195                 200                 205
Ser Ser Leu Gly Thr Gln Thr Tyr Ile Cys Asn Val Asn His Lys Pro
210                 215                 220
Ser Asn Thr Lys Val Asp Lys Lys Val Glu Pro Lys Ser Cys Asp Lys
225                 230                 235                 240
Thr His Thr Cys Pro Pro Cys Pro Ala Pro Glu Leu Leu Gly Gly Pro
                245                 250                 255
Ser Val Phe Leu Phe Pro Pro Lys Pro Lys Asp Thr Leu Met Ile Ser
            260                 265                 270
Arg Thr Pro Glu Val Thr Cys Val Val Val Asp Val Ser His Glu Asp
        275                 280                 285
Pro Glu Val Lys Phe Asn Trp Tyr Val Asp Gly Val Glu Val His Asn
290                 295                 300
Ala Lys Thr Lys Pro Arg Glu Glu Gln Tyr Asn Ser Thr Tyr Arg Val
305                 310                 315                 320
Val Ser Val Leu Thr Val Leu His Gln Asp Trp Leu Asn Gly Lys Glu
                325                 330                 335
Tyr Lys Cys Lys Val Ser Asn Lys Ala Leu Pro Ala Pro Ile Glu Lys
            340                 345                 350
Thr Ile Ser Lys Ala Lys Gly Gln Pro Arg Glu Pro Gln Val Tyr Thr
        355                 360                 365
Leu Pro Pro Ser Arg Asp Glu Leu Thr Lys Asn Gln Val Ser Leu Thr
370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Val Leu
                405                 410                 415
Asp Ser Asp Gly Ser Phe Phe Leu Tyr Ser Lys Leu Thr Val Asp Lys
            420                 425                 430
Ser Arg Trp Gln Gln Gly Asn Val Phe Ser Cys Ser Val Met His Glu
        435                 440                 445
Ala Leu His Asn His Tyr Thr Gln Lys Ser Leu Ser Leu Ser Pro Gly
            450                 455                 460
Lys
465

<210> SEQ ID NO 6
<211> LENGTH: 1418
<212> TYPE: DNA
<213> ORGANISM: Artificial Sequence
<220> FEATURE:
<221> NAME/KEY: CDS
<222> LOCATION: (24)..(1412)
<220> FEATURE:
```

<223> OTHER INFORMATION: Description of Artificial Sequence: Synthetic
      sequence

<400> SEQUENCE: 6

```
cgtaagcttc acagatcctc acc atg gga tgg agc tgt atc atc ctc ttt ctg           53
                        Met Gly Trp Ser Cys Ile Ile Leu Phe Leu
                         1               5                  10 gtg gca aca gct aca ggt gtc cac tcc cag gta cag cta gtg caa tca            101
Val Ala Thr Ala Thr Gly Val His Ser Gln Val Gln Leu Val Gln Ser
             15                  20                  25 ggg cct gaa gtg aag aag cct ggg gcc tca gtg aaa gtt tcc tgc aag            149
Gly Pro Glu Val Lys Lys Pro Gly Ala Ser Val Lys Val Ser Cys Lys
         30                  35                  40 gct tct ggc tac acc ttc acc aac tat gga atg aac tgg gta agg cag            197
Ala Ser Gly Tyr Thr Phe Thr Asn Tyr Gly Met Asn Trp Val Arg Gln
     45                  50                  55 gcg cct gga cag ggg ctt gag tgg atg ggg tgg ata aac acc tac act            245
Ala Pro Gly Gln Gly Leu Glu Trp Met Gly Trp Ile Asn Thr Tyr Thr
 60                  65                  70 gga gag cca aca tat ggt gaa gat ttc aag gga cgg ttt gca ttc tct            293
Gly Glu Pro Thr Tyr Gly Glu Asp Phe Lys Gly Arg Phe Ala Phe Ser
 75                  80                  85                  90 cta gac aca tcc gcc agc aca gcc tat atg gag ctc agc tcg ctg aga            341
Leu Asp Thr Ser Ala Ser Thr Ala Tyr Met Glu Leu Ser Ser Leu Arg
                 95                 100                 105 tcc gag gac act gca gtc tat ttc tgt gcg aga ttt ggt aac tac gta            389
Ser Glu Asp Thr Ala Val Tyr Phe Cys Ala Arg Phe Gly Asn Tyr Val
             110                 115                 120 gac tac tgg ggt caa gga tca cta gtc act gtc tcc tca gct tcc acc            437
Asp Tyr Trp Gly Gln Gly Ser Leu Val Thr Val Ser Ser Ala Ser Thr
         125                 130                 135 aag ggc cca tcc gtc ttc ccc ctg gcg ccc tgc tcc agg agc acc tcc            485
Lys Gly Pro Ser Val Phe Pro Leu Ala Pro Cys Ser Arg Ser Thr Ser
     140                 145                 150 gag agc aca gcc gcc ctg ggc tgc ctg gtc aag gac tac ttc ccc gaa            533
Glu Ser Thr Ala Ala Leu Gly Cys Leu Val Lys Asp Tyr Phe Pro Glu
155                 160                 165                 170 ccg gtg acg gtg tcg tgg aac tca ggc gcc ctg acc agc ggc gtg cac            581
Pro Val Thr Val Ser Trp Asn Ser Gly Ala Leu Thr Ser Gly Val His
                 175                 180                 185 acc ttc ccg gct gtc cta cag tcc tca gga ctc tac tcc ctc agc agc            629
Thr Phe Pro Ala Val Leu Gln Ser Ser Gly Leu Tyr Ser Leu Ser Ser
             190                 195                 200 gtg gtg acc gtg ccc tcc agc agc ttg ggc acg aag acc tac acc tgc            677
Val Val Thr Val Pro Ser Ser Ser Leu Gly Thr Lys Thr Tyr Thr Cys
         205                 210                 215 aac gta gat cac aag ccc agc aac acc aag gtg gac aag aga gtt gag            725
Asn Val Asp His Lys Pro Ser Asn Thr Lys Val Asp Lys Arg Val Glu
     220                 225                 230 tcc aaa tat ggt ccc cca tgc cca ccg tgc cct gca cct gag ttc gcg            773
Ser Lys Tyr Gly Pro Pro Cys Pro Pro Cys Pro Ala Pro Glu Phe Ala
235                 240                 245                 250 ggg gca cca tca gtc ttc ctg ttc ccc cca aaa ccc aag gac act ctc            821
Gly Ala Pro Ser Val Phe Leu Phe Pro Pro Lys Pro Lys Asp Thr Leu
                 255                 260                 265 atg atc tcc cgg acc cct gag gtc acg tgc gtg gtg gtg gac gtg agc            869
Met Ile Ser Arg Thr Pro Glu Val Thr Cys Val Val Val Asp Val Ser
             270                 275                 280 cag gaa gac ccc gag gtc cag ttc aac tgg tac gtg gat ggc gtg gag            917
Gln Glu Asp Pro Glu Val Gln Phe Asn Trp Tyr Val Asp Gly Val Glu
```

```
                    285                 290                 295
gtg cat aat gcc aag aca aag ccg cgg gag gag cag ttc aac agc acg        965
Val His Asn Ala Lys Thr Lys Pro Arg Glu Glu Gln Phe Asn Ser Thr
    300                 305                 310 tac cgt gtg gtc agc gtc ctc acc gtc ctg cac cag gac tgg ctg acc       1013
Tyr Arg Val Val Ser Val Leu Thr Val Leu His Gln Asp Trp Leu Thr
315                 320                 325                 330 ggc aag gcg tac aag tgc aag gtc tcc aac aaa ggc ctc ccg tcc tcc       1061
Gly Lys Ala Tyr Lys Cys Lys Val Ser Asn Lys Gly Leu Pro Ser Ser
                335                 340                 345 atc gag aaa acc atc tcc aaa gcc aaa ggg cag ccc cga gag cca cag       1109
Ile Glu Lys Thr Ile Ser Lys Ala Lys Gly Gln Pro Arg Glu Pro Gln
        350                 355                 360 gtg tac acc ctg ccc cca tcc cag gag gag atg acc aag aac cag gtc       1157
Val Tyr Thr Leu Pro Pro Ser Gln Glu Glu Met Thr Lys Asn Gln Val
            365                 370                 375 agc ctg acc tgc ctg gtc aaa ggc ttc tac ccc agc gac atc gcc gtg       1205
Ser Leu Thr Cys Leu Val Lys Gly Phe Tyr Pro Ser Asp Ile Ala Val
    380                 385                 390 gag tgg gag agc aat ggg cag ccg gag aac aac tac aag acc acg cct       1253
Glu Trp Glu Ser Asn Gly Gln Pro Glu Asn Asn Tyr Lys Thr Thr Pro
395                 400                 405                 410 ccc gtg ctg gac tcc gac ggc tcc ttc ttc ctc tac agc agg cta acc       1301
Pro Val Leu Asp Ser Asp Gly Ser Phe Phe Leu Tyr Ser Arg Leu Thr
                415                 420                 425 gtg gac aag agc agg tgg cag gag ggg aat gtc ttc tca tgc tcc gtg       1349
Val Asp Lys Ser Arg Trp Gln Glu Gly Asn Val Phe Ser Cys Ser Val
        430                 435                 440 atg cat gag gct ctg cac aac cac tac aca cag aag agc ctc tgc ctg       1397
Met His Glu Ala Leu His Asn His Tyr Thr Gln Lys Ser Leu Cys Leu
            445                 450                 455 tct ctg ggt aaa tga gaattc                                            1418
Ser Leu Gly Lys
    460

<210> SEQ ID NO 7
<211> LENGTH: 462
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 7

Met Gly Trp Ser Cys Ile Ile Leu Phe Leu Val Ala Thr Ala Thr Gly
1               5                   10                  15
Val His Ser Gln Val Gln Leu Val Gln Ser Gly Pro Glu Val Lys Lys
            20                  25                  30
Pro Gly Ala Ser Val Lys Val Ser Cys Lys Ala Ser Gly Tyr Thr Phe
        35                  40                  45
Thr Asn Tyr Gly Met Asn Trp Val Arg Gln Ala Pro Gly Gln Gly Leu
    50                  55                  60
Glu Trp Met Gly Trp Ile Asn Thr Tyr Thr Gly Glu Pro Thr Tyr Gly
65                  70                  75                  80
Glu Asp Phe Lys Gly Arg Phe Ala Phe Ser Leu Asp Thr Ser Ala Ser
                85                  90                  95
Thr Ala Tyr Met Glu Leu Ser Ser Leu Arg Ser Glu Asp Thr Ala Val
            100                 105                 110
Tyr Phe Cys Ala Arg Phe Gly Asn Tyr Val Asp Tyr Trp Gly Gln Gly
        115                 120                 125
Ser Leu Val Thr Val Ser Ser Ala Ser Thr Lys Gly Pro Ser Val Phe
    130                 135                 140
Pro Leu Ala Pro Cys Ser Arg Ser Thr Ser Glu Ser Thr Ala Ala Leu
145                 150                 155                 160
Gly Cys Leu Val Lys Asp Tyr Phe Pro Glu Pro Val Thr Val Ser Trp
                165                 170                 175
```

-continued

```
Asn Ser Gly Ala Leu Thr Ser Gly Val His Thr Phe Pro Ala Val Leu
            180                 185                 190
Gln Ser Ser Gly Leu Tyr Ser Leu Ser Ser Val Val Thr Val Pro Ser
        195                 200                 205
Ser Ser Leu Gly Thr Lys Thr Tyr Thr Cys Asn Val Asp His Lys Pro
    210                 215                 220
Ser Asn Thr Lys Val Asp Lys Arg Val Glu Ser Lys Tyr Gly Pro Pro
225                 230                 235                 240
Cys Pro Pro Cys Pro Ala Pro Glu Phe Ala Gly Ala Pro Ser Val Phe
                245                 250                 255
Leu Phe Pro Pro Lys Pro Lys Asp Thr Leu Met Ile Ser Arg Thr Pro
            260                 265                 270
Glu Val Thr Cys Val Val Val Asp Val Ser Gln Glu Asp Pro Glu Val
        275                 280                 285
Gln Phe Asn Trp Tyr Val Asp Gly Val Glu Val His Asn Ala Lys Thr
    290                 295                 300
Lys Pro Arg Glu Glu Gln Phe Asn Ser Thr Tyr Arg Val Val Ser Val
305                 310                 315                 320
Leu Thr Val Leu His Gln Asp Trp Leu Thr Gly Lys Ala Tyr Lys Cys
                325                 330                 335
Lys Val Ser Asn Lys Gly Leu Pro Ser Ser Ile Glu Lys Thr Ile Ser
            340                 345                 350
Lys Ala Lys Gly Gln Pro Arg Glu Pro Gln Val Tyr Thr Leu Pro Pro
        355                 360                 365
Ser Gln Glu Glu Met Thr Lys Asn Gln Val Ser Leu Thr Cys Leu Val
    370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
                405                 410                 415
Gly Ser Phe Phe Leu Tyr Ser Arg Leu Thr Val Asp Lys Ser Arg Trp
            420                 425                 430
Gln Glu Gly Asn Val Phe Ser Cys Ser Val Met His Glu Ala Leu His
        435                 440                 445
Asn His Tyr Thr Gln Lys Ser Leu Cys Leu Ser Leu Gly Lys
    450                 455                 460
```

<210> SEQ ID NO 8
<211> LENGTH: 1392
<212> TYPE: DNA
<213> ORGANISM: Artificial Sequence
<220> FEATURE:
<221> NAME/KEY: CDS
<222> LOCATION: (58)..(1386)
<220> FEATURE:
<223> OTHER INFORMATION: Description of Artificial Sequence: Synthetic
      sequence

<400> SEQUENCE: 8

```
atggattggc tgtggaactt gctattcctg atggcagctg cccaaagtat ccaagca       57 cag atc cag ttg gtg cag tct gga cct gaa ctg aag aag cct gga gag      105
Gln Ile Gln Leu Val Gln Ser Gly Pro Glu Leu Lys Lys Pro Gly Glu
  1               5                  10                  15 aca gtc aag atc tcc tgc aag gct tct gga tat acc ttc aca aac tat     153
Thr Val Lys Ile Ser Cys Lys Ala Ser Gly Tyr Thr Phe Thr Asn Tyr
             20                  25                  30 gga atg aac tgg gtg agg cag gct tca gga gag ggt tta aag tgg atg    201
Gly Met Asn Trp Val Arg Gln Ala Ser Gly Glu Gly Leu Lys Trp Met
         35                  40                  45 ggc tgg ata aac acc tac act gga gag cca aca tat ggt gaa gat ttc    249
Gly Trp Ile Asn Thr Tyr Thr Gly Glu Pro Thr Tyr Gly Glu Asp Phe
     50                  55                  60 aag gga cgg ttt gcc ttc tct ttg gaa acc tct gcc agc act gcc tat    297
Lys Gly Arg Phe Ala Phe Ser Leu Glu Thr Ser Ala Ser Thr Ala Tyr
 65                  70                  75                  80 ttg cag atc aac aac ctc aaa aat gaa gac acg gct aca tat ttc tgt    345
Leu Gln Ile Asn Asn Leu Lys Asn Glu Asp Thr Ala Thr Tyr Phe Cys
                 85                  90                  95 gca aga ttt ggt aac tac gta gac tac tgg ggc caa ggc acc act ctc    393
Ala Arg Phe Gly Asn Tyr Val Asp Tyr Trp Gly Gln Gly Thr Thr Leu
```

-continued

```
                     100                 105                 110
aca gtc tcc tca gcc tcc acc aag ggc cca tcg gtc ttc ccc ctg gcg    441
Thr Val Ser Ser Ala Ser Thr Lys Gly Pro Ser Val Phe Pro Leu Ala
            115                 120                 125 ccc tgc tcc agg agc acc tcc gag agc aca gcg gcc ctg ggc tgc ctg    489
Pro Cys Ser Arg Ser Thr Ser Glu Ser Thr Ala Ala Leu Gly Cys Leu
    130                 135                 140 gtc aag gac tac ttc ccc gaa ccg gtg acg gtg tcg tgg aac tca ggc    537
Val Lys Asp Tyr Phe Pro Glu Pro Val Thr Val Ser Trp Asn Ser Gly
145                 150                 155                 160 gct ctg acc agc ggc gtg cac acc ttc cca gct gtc cta cag tcc tca    585
Ala Leu Thr Ser Gly Val His Thr Phe Pro Ala Val Leu Gln Ser Ser
                165                 170                 175 gga ctc tac tcc ctc agc agc gtg gtg acc gtg ccc tcc agc aac ttc    633
Gly Leu Tyr Ser Leu Ser Ser Val Val Thr Val Pro Ser Ser Asn Phe
            180                 185                 190 ggc acc cag acc tac acc tgc aac gta gat cac aag ccc agc aac acc    681
Gly Thr Gln Thr Tyr Thr Cys Asn Val Asp His Lys Pro Ser Asn Thr
        195                 200                 205 aag gtg gac aag aca gtt gag cgc aaa tgt tgt gtc gag tgc cca ccg    729
Lys Val Asp Lys Thr Val Glu Arg Lys Cys Cys Val Glu Cys Pro Pro
210                 215                 220 tgc cca gca cca cct gtg gca gga ccg tca gtc ttc ctc ttc ccc cca    777
Cys Pro Ala Pro Pro Val Ala Gly Pro Ser Val Phe Leu Phe Pro Pro
225                 230                 235                 240 aaa ccc aag gac acc ctc atg atc tcc cgg acc cct gag gtc acg tgc    825
Lys Pro Lys Asp Thr Leu Met Ile Ser Arg Thr Pro Glu Val Thr Cys
                245                 250                 255 gtg gtg gtg gac gtg agc cac gaa gac ccc gag gtc cag ttc aac tgg    873
Val Val Val Asp Val Ser His Glu Asp Pro Glu Val Gln Phe Asn Trp
            260                 265                 270 tac gtg gac ggc gtg gag gtg cat aat gcc aag aca aag cca cgg gag    921
Tyr Val Asp Gly Val Glu Val His Asn Ala Lys Thr Lys Pro Arg Glu
        275                 280                 285 gag cag ttc aac agc acg ttc cgt gtg gtc agc gtc ctc acc gtt gtg    969
Glu Gln Phe Asn Ser Thr Phe Arg Val Val Ser Val Leu Thr Val Val
    290                 295                 300 cac cag gac tgg ctg aac ggc aag gag tac aag tgc aag gtc tcc aac   1017
His Gln Asp Trp Leu Asn Gly Lys Glu Tyr Lys Cys Lys Val Ser Asn
305                 310                 315                 320 aaa ggc ctc cca gcc ccc atc gag aaa acc atc tcc aaa acc aaa ggg   1065
Lys Gly Leu Pro Ala Pro Ile Glu Lys Thr Ile Ser Lys Thr Lys Gly
                325                 330                 335 cag ccc cga gaa cca cag gtg tac acc ctg ccc cca tcc cgg gag gag   1113
Gln Pro Arg Glu Pro Gln Val Tyr Thr Leu Pro Pro Ser Arg Glu Glu
            340                 345                 350 atg acc aag aac cag gtc agc ctg acc tgc ctg gtc aaa ggc ttc tac   1161
Met Thr Lys Asn Gln Val Ser Leu Thr Cys Leu Val Lys Gly Phe Tyr
        355                 360                 365 ccc agc gac atc gcc gtg gag tgg gag agc aat ggg cag ccg gag aac   1209
Pro Ser Asp Ile Ala Val Glu Trp Glu Ser Asn Gly Gln Pro Glu Asn
    370                 375                 380 aac tac aag acc aca cct ccc atg ctg gac tcc gac ggc tcc ttc ttc   1257
Asn Tyr Lys Thr Thr Pro Pro Met Leu Asp Ser Asp Gly Ser Phe Phe
385                 390                 395                 400 ctc tac agc aag ctc acc gtg gac aag agc agg tgg cag cag ggg aac   1305
Leu Tyr Ser Lys Leu Thr Val Asp Lys Ser Arg Trp Gln Gln Gly Asn
                405                 410                 415 gtc ttc tca tgc tcc gtg atg cat gag gct ctg cac aac cac tac aca   1353
```

-continued

```
Val Phe Ser Cys Ser Val Met His Glu Ala Leu His Asn His Tyr Thr
                420                 425                 430 cag aag agc ctc tgc ctg tct ctg ggt aaa tga gaattc                    1392
Gln Lys Ser Leu Cys Leu Ser Leu Gly Lys
        435                 440
```

<210> SEQ ID NO 9
<211> LENGTH: 442
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 9

```
Gln Ile Gln Leu Val Gln Ser Gly Pro Glu Leu Lys Lys Pro Gly Glu
  1               5                  10                  15

Thr Val Lys Ile Ser Cys Lys Ala Ser Gly Tyr Thr Phe Thr Asn Tyr
             20                  25                  30

Gly Met Asn Trp Val Arg Gln Ala Ser Gly Glu Gly Leu Lys Trp Met
         35                  40                  45

Gly Trp Ile Asn Thr Tyr Thr Gly Glu Pro Thr Tyr Gly Glu Asp Phe
     50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Ala Arg Phe Gly Asn Tyr Val Asp Tyr Trp Gly Gln Gly Thr Thr Leu
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
        195                 200                 205

Lys Val Asp Lys Thr Val Glu Arg Lys Cys Cys Val Glu Cys Pro Pro
    210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Phe Arg Val Val Ser Val Leu Thr Val Val
    290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
```

|     |     |     |     |     | 325 |     |     |     |     | 330 |     |     |     |     | 335 |     |     |
| --- | --- | --- | --- | --- | --- | --- | --- | --- | --- | --- | --- | --- | --- | --- | --- | --- | --- |

Gln Pro Arg Glu Pro Gln Val Tyr Thr Leu Pro Pro Ser Arg Glu Glu
            340                         345                 350

Met Thr Lys Asn Gln Val Ser Leu Thr Cys Leu Val Lys Gly Phe Tyr
            355                         360                 365

Pro Ser Asp Ile Ala Val Glu Trp Glu Ser Asn Gly Gln Pro Glu Asn
            370                         375                 380

Asn Tyr Lys Thr Thr Pro Pro Met Leu Asp Ser Asp Gly Ser Phe Phe
385                         390                         395                         400

Leu Tyr Ser Lys Leu Thr Val Asp Lys Ser Arg Trp Gln Gln Gly Asn
            405                         410                 415

Val Phe Ser Cys Ser Val Met His Glu Ala Leu His Asn His Tyr Thr
            420                         425                 430

Gln Lys Ser Leu Cys Leu Ser Leu Gly Lys
            435                         440

<210> SEQ ID NO 10
<211> LENGTH: 1392
<212> TYPE: DNA
<213> ORGANISM: Artificial Sequence
<220> FEATURE:
<223> OTHER INFORMATION: Description of Artificial Sequence: Synthetic
      sequence

<400> SEQUENCE: 10
gaattctcat ttacccagag acaggcagag gctcttctgt gtgtagtggt tgtgcagagc      60
ctcatgcatc acggagcatg agaagacgtt ccctgctgc cacctgctct tgtccacggt     120
gagcttgctg tagaggaaga aggagccgtc ggagtccagc atgggagtg tggtcttgta     180
gttgttctcc ggctgcccat tgctctccca ctccacggcg atgtcgctgg ggtagaagcc     240
tttgaccagg caggtcaggc tgacctggtt cttggtcatc tcctcccggg atggggcag     300
ggtgtacacc tgtggttctc ggggctgccc tttggttttg agatggtttt tctcgatggg     360
ggctgggagg cctttgttgg agaccttgca cttgtactcc ttgccgttca gccagtcctg     420
gtgcacaacg gtgaggacgc tgaccacacg aacgtgctg ttgaactgct cctcccgtgg     480
cttgtcttg gcattatgca cctccacgcc gtccacgtac cagttgaact ggaccctcggg     540
gtcttcgtgg ctcacgtcca ccaccacgca cgtgacctca ggggtccggg agatcatgag     600
ggtgtccttg ggttttgggg ggaagaggaa gactgacggt cctgccacag gtggtgctgg     660
gcacggtggg cactcgacac aacatttgcg ctcaactgtc ttgtccacct tggtgttgct     720
gggcttgtga tctacgttgc aggtgtaggt ctgggtgccg aagttgctgg agggcacggt     780
caccacgctg ctgagggagt agagtcctga ggactgtagg acagctggga aggtgtgcac     840
gccgctggtc agagcgcctg agttccacga caccgtcacc ggttcgggga agtagtcctt     900
gaccaggcag cccagggccg ctgtgctctc ggaggtgctc ctggagcagg cgccagggg     960
gaagaccgat gggcccttgg tgaggctga ggagactgtg agagtggtgc cttggcccca    1020
gtagtctacg tagttaccaa atcttgcaca gaaatatgta gccgtgtctt catttttgag    1080
gttgttgatc tgcaaatagg cagtgctggc agaggtttcc aaagagaagg caaaccgtcc    1140
cttgaaatct tcaccatatg ttggctctcc agtgtaggtg tttatccagc ccatccactt    1200
taaaccctct cctgaagcct gcctcaccca gttcattcca gtttgtgtga aggtatatcc    1260
agaagccttg caggagatct tgactgtctc tccaggcttc ttcagttcag gtccagactg    1320
caccaactgg atctgtgctt ggatactttg ggcagctgcc atcaggaata gcaagttcca    1380
cagccaatcc at                                                               1392

<210> SEQ ID NO 11
<211> LENGTH: 238
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 11

Met Gly Trp Ser Cys Ile Ile Leu Phe Leu Val Ala Thr Ala Thr Gly
 1               5                  10                  15

Val His Ser Asp Ile Val Met Thr Gln Ser Pro Leu Ser Leu Pro Val
             20                  25                  30

Thr Pro Gly Glu Pro Ala Ser Ile Ser Cys Arg Ser Ser Lys Asn Leu
         35                  40                  45

Leu His Ser Asn Gly Ile Thr Tyr Leu Tyr Trp Tyr Leu Gln Lys Pro
     50                  55                  60

Gly Gln Ser Pro Gln Leu Leu Ile Tyr Gln Met Ser Asn Leu Ala Ser
 65                  70                  75                  80

Gly Val Pro Asp Arg Phe Ser Ser Gly Ser Gly Thr Asp Phe Thr
                 85                  90                  95

Leu Lys Ile Ser Arg Val Glu Ala Glu Asp Val Gly Val Tyr Tyr Cys
            100                 105                 110

Ala Gln Asn Leu Glu Ile Pro Arg Thr Phe Gly Gln Gly Thr Lys Val
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 12
<211> LENGTH: 465
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 12

Met Gly Trp Ser Cys Ile Ile Leu Phe Leu Val Ala Thr Ala Thr Gly
 1               5                  10                  15

Val His Ser Gln Val Gln Leu Val Gln Ser Gly Pro Glu Val Lys Lys
             20                  25                  30

Pro Gly Ala Ser Val Lys Val Ser Cys Lys Ala Ser Gly Tyr Thr Phe
         35                  40                  45

```
Thr Asn Tyr Gly Met Asn Trp Val Arg Gln Ala Pro Gly Gln Gly Leu
 50                  55                  60

Glu Trp Met Gly Trp Ile Asn Thr Tyr Thr Gly Glu Pro Thr Tyr Gly
 65                  70                  75                  80

Glu Asp Phe Lys Gly Arg Phe Ala Phe Ser Leu Asp Thr Ser Ala Ser
                 85                  90                  95

Thr Ala Tyr Met Glu Leu Ser Ser Leu Arg Ser Glu Asp Thr Ala Val
            100                 105                 110

Tyr Phe Cys Ala Arg Phe Gly Asn Tyr Val Asp Tyr Trp Gly Gln Gly
        115                 120                 125

Ser Leu Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
```

465

<210> SEQ ID NO 13
<211> LENGTH: 238
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 13

Met Gly Trp Ser Cys Ile Ile Leu Phe Leu Val Ala Thr Ala Thr Gly
1               5                   10                  15

Val His Ser Asp Ile Val Met Thr Gln Ser Pro Leu Ser Leu Pro Val
            20                  25                  30

Thr Pro Gly Glu Pro Ala Ser Ile Ser Cys Arg Ser Ser Lys Asn Leu
        35                  40                  45

Leu His Ser Asn Gly Ile Thr Tyr Leu Tyr Trp Tyr Leu Gln Lys Pro
    50                  55                  60

Gly Gln Ser Pro Gln Leu Leu Ile Tyr Gln Met Ser Asn Leu Ala Ser
65                  70                  75                  80

Gly Val Pro Asp Arg Phe Ser Ser Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Ala Gln Asn Leu Glu Ile Pro Arg Thr Phe Gly Gln Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 14
<211> LENGTH: 462
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 14

Met Gly Trp Ser Cys Ile Ile Leu Phe Leu Val Ala Thr Ala Thr Gly
1               5                   10                  15

Val His Ser Gln Val Gln Leu Val Gln Ser Gly Pro Glu Val Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Gln Gly Leu

```
              50                  55                  60
Glu Trp Met Gly Trp Ile Asn Thr Tyr Thr Gly Glu Pro Thr Tyr Gly
 65                  70                  75                  80

Glu Asp Phe Lys Gly Arg Phe Ala Phe Ser Leu Asp Thr Ser Ala Ser
                 85                  90                  95

Thr Ala Tyr Met Glu Leu Ser Ser Leu Arg Ser Glu Asp Thr Ala Val
            100                 105                 110

Tyr Phe Cys Ala Arg Phe Gly Asn Tyr Val Asp Tyr Trp Gly Gln Gly
        115                 120                 125

Ser Leu Val Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Lys Thr Tyr Thr Cys Asn Val Asp His Lys Pro
    210                 215                 220

Ser Asn Thr Lys Val Asp Lys Arg Val Glu Ser Lys Tyr Gly Pro Pro
225                 230                 235                 240

Cys Pro Pro Cys Pro Ala Pro Glu Phe Ala Gly Ala Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser Gln Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Tyr Arg Val Val Ser Val
305                 310                 315                 320

Leu Thr Val Leu His Gln Asp Trp Leu Asn Gly Lys Ala Tyr Lys Cys
                325                 330                 335

Lys Val Ser Asn Lys Gly Leu Pro Ser Ser Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Gln Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Arg Leu Thr Val Asp Lys Ser Arg Trp
            420                 425                 430

Gln Glu Gly Asn Val Phe Ser Cys Ser Val Met His Glu Ala Leu His
        435                 440                 445

Asn His Tyr Thr Gln Lys Ser Leu Cys Leu Ser Leu Gly Lys
    450                 455                 460

<210> SEQ ID NO 15
```

<211> LENGTH: 238
<212> TYPE: PRT
<213> ORGANISM: Artificial Sequence
<220> FEATURE:
<223> OTHER INFORMATION: Description of Artificial Sequence: Synthetic sequence

<400> SEQUENCE: 15

Met Gly Trp Ser Cys Ile Ile Leu Phe Leu Val Ala Thr Ala Thr Gly
1               5                   10                  15

Val His Ser Asp Ile Val Met Thr Gln Ser Pro Leu Ser Leu Pro Val
            20                  25                  30

Thr Pro Gly Glu Pro Ala Ser Ile Ser Cys Arg Ser Ser Lys Asn Leu
        35                  40                  45

Leu His Ser Asn Gly Ile Thr Tyr Leu Tyr Trp Tyr Leu Gln Lys Pro
    50                  55                  60

Gly Gln Ser Pro Gln Leu Leu Ile Tyr Gln Met Ser Asn Leu Ala Ser
65                  70                  75                  80

Gly Val Pro Asp Arg Phe Ser Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Ala Gln Asn Leu Glu Ile Pro Arg Thr Phe Gly Gln Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 16
<211> LENGTH: 461
<212> TYPE: PRT
<213> ORGANISM: Artificial Sequence
<220> FEATURE:
<223> OTHER INFORMATION: Description of Artificial Sequence: Synthetic sequence

<400> SEQUENCE: 16

Met Gly Trp Ser Cys Ile Ile Leu Phe Leu Val Ala Thr Ala Thr Gly
1               5                   10                  15

Val His Ser Gln Val Gln Leu Val Gln Ser Gly Pro Glu Val Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Glu Trp Met Gly Trp Ile Asn Thr Tyr Thr Gly Glu Pro Thr Tyr Gly
65                  70                  75                  80

-continued

```
Glu Asp Phe Lys Gly Arg Phe Ala Phe Ser Leu Asp Thr Ser Ala Ser
                85                  90                  95

Thr Ala Tyr Met Glu Leu Ser Ser Leu Arg Ser Glu Asp Thr Ala Val
            100                 105                 110

Tyr Phe Cys Ala Arg Phe Gly Asn Tyr Val Asp Tyr Trp Gly Gln Gly
        115                 120                 125

Ser Leu Val Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
    210                 215                 220

Ser Asn Thr Lys Val Asp Lys Thr Val Glu Arg Lys Cys Cys Val Glu
225                 230                 235                 240

Cys Pro Pro Cys Pro Ala Pro Pro Val Ala Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Gln
        275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Phe Arg Val Val Ser Val Leu
305                 310                 315                 320

Thr Val Val His Gln Asp Trp Leu Asn Gly Lys Glu Tyr Lys Cys Lys
                325                 330                 335

Val Ser Asn Lys Gly Leu Pro Ala Pro Ile Glu Lys Thr Ile Ser Lys
            340                 345                 350

Thr Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Met Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Cys Leu Ser Leu Gly Lys
450                 455                 460
```

COMBINATION OF ANTI-EP-CAM ANTIBODY WITH A CHEMOTHERAPEUTIC AGENT

This application is a continuation of U.S. Application No 10/031,355 filed Jan. 18, 2002, now abandoned, which was filed pursuant to 35 U.S.C. § 371 as a U.S. National Phase Application of International Application No. PCT/EP99/05271 filed Jul. 23, 1999.

The conventional therapeutic approaches to cancer include surgery, radiotherapy and chemotherapy in various combinations; however, response rates have not improved significantly in the last 20 years. The major limitation of chemotherapy and radiotherapy is the non-selective targeting of both normal and tumour cells that results in toxic side effects. In the search for less toxic and more specific treatment alternatives, various types of immunotherapy have been investigated. Among these modalities, strategies based on monoclonal antibodies have been applied to a broad spectrum of malignancies (Riethmüller et al. Curr Opin Immun 1992, 4, 647-655 and Riethmüller et al. Curr Opin Immunol 1993, 5, 732-739). The utility of monoclonal antibodies is based upon their clonal antigen specificity, i.e. molecular recognition of specific epitopes which may comprise an antigen and to bind to these antigens with high affinity. Monoclonal antibodies can bind to antigens expressed uniquely or preferentially on the surface of malignant cells, and hence can be used to specifically target and destroy tumour cells. Antibodies may be constructed as delivery vehicles for drugs or DNA, or as conjugates with radionuclides. Binding of naked antibody to target cells may also activate innate antitumour immune functions such as antibody-dependent cell-mediated cytotoxicity (ADCC) and complement-mediated cytotoxicity (CMC), either of which may result in lysis or phagocytosis of the targeted cell. Both ADCC and CMC are antibody-dose-related immune functions and it is therefore desirable to get as much antibody bound to target cells as possible. One way of achieving this objective is to increase the level of expression of the relevant antigen which may effectively increase antibody functions such as, for example, ADCC of the target cells by virtue of getting more antibody bound to the cells (Fogler et al. Cancer Research 48: 6303-6308 (1988)).

One antigen of importance in cancer therapy is the Ep-CAM antigen (human pan-carcinoma antigen). This antigen is a transmembrane glycoprotein which has been reported to function as a cell adhesion molecule (Litvinow et al. J. Cell Biology 125: 437446, 1994) and is also known as the 17-1A antigen, 40 kD antigen, EGP40, GA733-2, KSA and ESA but may be known by other names or descriptions in the literature as well. It is expressed on the baso-lateral surface of a majority of simple cuboidal or columnar, pseudo stratified columnar and transitional epithelia and at generally higher levels in tumour cells. Epithelial cells are known to be the most important cell type in the development of human malignancies. Thus more than 90% of all malignant tumours are carcinomas, and therefore of epithelial origin (Acta Anatomica; 156 (3); 217-226 (1996)). Although the Ep-CAM antigen is expressed on most tumour cells of epithelial origin there are examples of cells of epithelal origin that do not express Ep-CAM such as adult epithelial tissues, epidermal adult keratinocytes, gastric parietal cells, thymic cortical epithelium, myoepithelial cells and hepatocytes. The phenotype of a malignant cell plays an important role in the efficacy of monoclonal antibodies. While tumour specific antigens have proven to be elusive, differences in expression of the antigens between normal cells and tumour cells have provided a means to target antibodies to tumours. It would be clinically advantageous to improve on these differences by enhancement of antigen homogeneity and density of expression on tumour cells.

Interferons are well-known to alter cell phenotypes by increasing expression of tumour antigens as well as many normal antigens, e.g. Class I HLA. For example, human recombinant interferon-$\alpha$ and interferon-$\gamma$ can increase the expression of human tumour antigens TAG-72 and CEA (Greiner et al. Cancer Res 44: 3208-3214 (1984)). Interferon exposure induced a more homogeneous CEA-positive tumour cell population which shed more CEA from the cells surface, which was confirmed by in vivo studies with human carcinoma xenografts in athymic mice. Treatment with interferon-$\gamma$ enhanced TAG-72 and CEA expression on ovarian or gastrointestinal tumour cells in patients' malignant ascites (Greiner et al. J Clin Oncol 10: 735-746 (1992)). The effects of interferons on cells are myriad and range from direct cytotoxicity to immunopotentiation to antiproliferative activity. None of the effects of interferons on antigen expression have been directly ascribed to interference with cell cycle progression.

Briefly, cell cycle progression refers to the sequence of events between one mitotic division and another in a cell. A quiescent resting phase ($G_0$) is followed by a growth phase ($G_1$), then by a DNA synthesis phase (S). A second growth phase of cell enlargement ($G_2$) and DNA replication (M phase) is followed by division of the cell into two progeny cells. Any interference with the cell machinery may inhibit all cycle progression at any phase of the cell cycle. For example, specific chemotherapeutic agents may block progression in either $G_2$ or M or in both $G_2$ and M ($G_2$/M). In other words exposure to certain drugs e.g. chemotherapeutic agents will for example, arrest individual cells in $G_2$ and/or M until eventually most, or all of the cells in a population become arrested in $G_2$ and/or M ($G_2$/M). In HeLa cells, for example, the $G_1$, S, $G_2$ and M phase take 8.2, 6.2, 4.6 and 0.6 hours, respectively. The period between mitoses is called interphase. Cells may have different doubling times, depending on their developmental stage or tissue type. The variation in doubling times is usually a function of the time spent in $G_1$ (A Dictionary of Genetics, 5th edition, R C King and W D Stansfield, Oxford University Press, 1997).

While a few proteins have been identified as produced solely at certain phases of the cell cycle, and therefore can serve as markers of cell cycle status, most others are produced across the cell cycle but at higher or lower levels at certain points. Variation of antigen density across the cell cycle is typical for the sarcoma antigens p102 and p200 (Song S, Anticancer Research 16(3A): 1171-5 (1996)), the leukaemia/lymphoma-associated antigen JD118 (Czuczman et al. Cancer Immunology, Immunotherapy 36(6): 387-96 (1993)), and the gastric tumour antigen PC1 (Wei et al., J of Oncology 9(3): 179-82 (1987)). A few tumour antigens have been reported to be cell-cycle independent, e.g. liver metastases 3H4 (Wulf et al., J. Cancer Research and Clinical Oncology 122(8): 476-82 (1996)) and small cell lung cancer antigens (Fargion et al., Cancer Research 46: 2633-2638 (1986)).

Surprisingly, it has been found that pre-treatment with a drug, for example a chemotherapeutic agent known to block cell cycle progression at S and/or $G_2$/M results in a significant increase in the density of the Ep-CAM antigen population and thus in greater targeting of anti-Ep-CAM antibodies to Ep-CAM expressing tumours. In lytic antibodies this translates into an increased susceptibility to antibody-dependent cytolysis. This perturbation of tumour cell phenotype has a significant impact on the biological effectiveness of therapeutic antibodies, and provides synergistic benefit to standard chemotherapeutic regimens. Furthermore, this increase in Ep-CAM antigen expression appears to be tumour specific. In other words, pre-treatment with chemotherapeutic agents that block the cell cycle at S and/or $G_2$/M does not seem to affect Ep-CAM antigen expression in non-tumour cells.

Accordingly, the present invention provides a combination of an Ep-CAM antibody and a chemotherapeutic agent that is capable of arresting Ep-CAM antigen expressing cells in S or $G_2$/M, preferably in $G_2$/M.

Examples of anti-Ep-CAM antibodies are ING1 (Colcher et al., Proc. Natl. Acad. Sci. USA, 78 (5), 3199 to 3203 (1981) and Laio et al, Human Antibody Hybridomas 1(2), 66-76 (1990)); 17-1A e.g. Panorex (Herlyn et al, Proc. Natl. Acad. Sci. USA 76: 1438-1452 (1979) and Herlyn et al, Hybridoma 1985; 5 (suppl. 1) S3 to S10); and NR-LU-10 (Okabe et al, Cancer Research, 44, 5273 to 5278 (1984)).

Panorex (Adjuqual®) is a 17.1A mouse monoclonal antibody. It is marketed by Glaxo Wellcome in Germany for the post-operative adjuvant therapy of colorectal cancer.

An example of an anti-Ep-CAM antibody is one with the variable light chain cDNA sequence as set out in FIG. 15 and the heavy chain cDNA sequence as set out in FIG. 16. (known as humanised 323/A3/IgG$_1$). Two further preferred examples of anti-Ep-CAM antibodies are those with the variable light chain cDNA sequence as set out in FIG. 15 and heavy chain cDNA sequences as set out in FIG. 17 or 18 respectively (known as humanised 323/A3 IgG$_4$ and IgG$_2$cys respectively).

A preferred example of an anti-Ep-CAM antibody is 17.1A, most preferably Panorex.

Specific anti-Ep-CAM antibodies can be given on their own or in combination with other anti-Ep-CAM antibodies. Examples of such anti-Ep-CAM antibody combinations are an anti-Ep-CAM antibody with the variable light chain cDNA sequence as set out in FIG. 15 and the heavy chain cDNA sequence as set out in FIG. 16 in combination with ING1. Thus throughout the specification reference to an anti-Ep-CAM antibody includes antibody combinations of various anti-Ep-CAM antibodies, preferably non-competing anti-Ep-CAM antibodies targeting different epitopes on the same Ep-CAM antigen.

Examples of chemotherapeutic agents which are capable of arresting Ep-CAM antigen expressing cells in $G_2$/M are vinorelbine, cisplatin, mytomycin, paclitaxel, carboplatin, oxaliplatin and CPT-II (camptothecin).

Vinorelbine tartrate is a semisynthetic vinca alkaloid with the chemical name 3',4'-didehydro-4'-deoxy-C'-norvincaleukoblastine [R—(R*,R*)-2,3-dihydroxybutanedioate (1:2) (salt)]. Vinorelbine tartrate is used in combination with other chemotherapy agents such as cisplatin or as a single agent in the treatment of various solid tumours particularly non-small cell lung, advanced breast, and hormone refractory prostate cancers. The brand name Navelbine® is used in North America and Europe. Navelbine® is administered intravenously as a single-agent or in combination therapy typically at doses of 20-30 mg/m$^2$ on a weekly basis. An oral formulation of vinorelbine is in clinical development.

Cisplatin has the chemical name cis-diamminedichloroplatinum. Cisplatin is used in the treatment of metastatic testicular tumours as a combination therapy, as single and combination therapy in metastatic ovarian tumours, as well as a single agent in advanced bladder cancer. Cisplatin is manufactured by Bristol-Myers Squibb under the brand names of Platinol® and Platinol-AQ®. Cisplatin is also used in the following types of cancer, typically in combination therapy: non-small cell and small cell lung cancers, head and neck, endometrial, cervical, and non-Hodgkin's lymphoma. Cisplatin is typically administered intravenously in doses ranging from 15-150 mg/m$^2$ once every 3 to 4 weeks, or daily for 5 days repeated every 3 or 4 weeks. However, higher and more frequent doses are occasionally administered and the route of administration could be different than intravenous, such as intra-arterial or intraperitoneal.

Carboplatin has the chemical name platinum, diammine [1,1-cyclobutane-dicarboxylato(2)-0,0']-(SP-4-2). Carboplatin is usually administered in combination with other cytotoxics such as paclitaxel and etoposide. It is used in the treatment of advanced ovarian cancer, non-small cell lung cancer as well as in many of the same types of cancer as cisplatin is used. The brand name of carboplatin manufactured by Bristol-Myers Squibb is Paraplatin®. Carboplatin is typically administered intravenously at 300-400 mg/m$^2$, or to a target area under the drug concentration versus time curve (AUC) of 4-6 mg/ml-min using the patient's estimated glomerular filtration rate (GFR). Higher doses up to around 1600 mg/m$^2$ divided over several, usually five, days may also be administered.

Paclitaxel has the chemical name 5β, 20 epoxy-1,2α,4,7β, 10β,13α-hexahydroxytax-11-en-9-one 4,10-diacetate 2-benzoate 13-ester with (2R,3S)—N-benzoyl-3-phenylisoserine. Paclitaxel is manufactured by Bristol-Myers Squibb as Taxol®. It is used to treat a variety of carcinomas including ovarian, breast, non-small cell lung, head and neck. Typical doses include 135-175 mg/m$^2$ as either a 3 or 24 hour intravenous infusion given every 3 or 4 weeks. Higher doses up to around 300 mg/m$^2$ have also been administered.

Besides the active ingredient, the drug products provided by manufacturers typically contain a diluent such as sterile water, dextrose 5% in water or 0.9% sodium chloride in water with additional excipients such as Cremophor vehicle added to make for example, paclitaxel soluble.

More detailed information on treatment regimes, dosages and compositions etc can be obtained from standard reference books such as: Martindale, The Extra Pharmacopoeia, 31st edition, edited by J E F Reynolds, London, Royal Pharmaceutical Society, 1996 and the Physicians Desk reference, 49th Edition, 1995, Medical Economics Data Production Company, Montvale.

Other chemotherapeutic agents that may cause cells to accumulate in $G_2$/M include anthracyclines e.g. doxorubicin and aclarubicin; carmustine (BCNU), camptothecin, 9-nitrocamptothecin, cyclophosphamide and its derivatives, docetaxel, etoposide, Razoxane (ICRF-187), alkyllyso-phospholipids e.g. ilmofosine; methotrexate, MST-16, taxanes, vinblastine, vincristine and teniposide (VM-26) (again see Martindale, The Extra Pharmacopoeia, 31st edition, edited by J E F Reynolds, London, Royal Pharmaceutical Society, 1996) and flavonoids e.g. apigenin and genistein (see The Merck Index, 12th edition, Merck Research Laboratories, Merck and Co Inc, 1996). In addition, adozelesin (a class of pyrazole compounds) (Cancer Research 1992, Oct. 15; 52 (2): 5687 to 5692)), Bistratene A (Mutation Research 1996, Mar. 1; 367 (3): 169 to 175), cycloxazoline (Cancer Chemotherapy & Pharmacology 1994; 33(5): 399 to 409), imidazoarcridinone, melephan (Experimental Cell Biology 1986; 54 (3): 138 to 148 and International Journal of Cancer 1995, Jul. 17; 62 (2): 170 to 175), merbarone (Environmental & Molecular Mutagenesis 1997; 29 (1): 16 to 27 and Cancer Research 1995, Apr. 1; 55 (7): 1509 to 1516) and oracin (FEBS Letters 1997, Jan. 2; 400 (1): 127 to 130) are also believed to cause cells to accumulate in $G_2$/M generally all topo II inhibitors, e.g. to potecan (abpi, 1998-1999), all vinca derivatives and all DNA damaging agents including radiation are also believed to arrest cells in $G_2$/M.

Moreover, 5FU has been reported to arrest cells in $G_2/M$ (Oncology Research 1994; 6(7): 303-309) and it is therefore believed that 5FU and compounds similar to 5FU such as UFT, methotrexate, capecitabine and Gemcitabine will increase Ep-Cam expression in some tissues. Similarly, tomudex (Raloxifen) which is known to arrest cells in the S phase is believed to increase Ep-Cam expression.

The term "chemotherapeutic agent" throughout the specification is therefore not limited to cytotoxic therapy, but also encompasses cytostatic therapy and any other drugs capable of stopping cells in $G_2/M$. It should be further noted that radiotherapy is capable of arresting cells in $G_2/M$ and that throughout the specification the term chemotherapeutic can therefore be substituted with "radiotherapy".

Throughout the specification reference to a chemotherapeutic agent includes combinations of one or more specific chemotherapeutic agents which arrest Ep-CAM expressing tumour cells in $G_2/M$. Examples of typical combinations are vinorelbine with cisplatin and paclitaxel with carboplatin; oxaliplatin with 5FU; cyclophosphamide with methotrexate and 5FU; cyclophosphamide with doxorubicin and 5FU.

While it is possible for the chemotherapeutic agent to be administered alone it is preferable to present it as a pharmaceutical composition comprising an active ingredient, as defined above, together with an acceptable carrier therefor. Each carrier must be "acceptable" in the sense of being compatible with the other ingredients of the composition and not injurious to the recipient.

Preferred combinations of an Ep-Cam antibody and a chemotherapeutic agent(s) that are capable of arresting Ep-CAM antigen expressing cells in S or $G_2/M$ are: Panorex in combination with any of the following chemotherapeutic agents: UFT, Capecitabine, CPT-II, Oxaliplatin, 5FU, 5FU continuous infusion, Paclitaxel, Docetaxel, Cyclophosphamide, Methotrexate, Doxorubicin, Navelbine (iv and oral), Epirubicin, Mitoxantrone, Raloxifen, Cisplatin, Mitomycin, Carboplatinum, Gemcitabine, Etoposide and Topotecan.

Particularly preferred combinations are Panorex with CPT-II, 5FU (continuous infusion), Oxaliplatin, Capecitibine, UFT and Tomudex (Raloxifen).

These Panorex combinations are useful in the treatment of cancer, particualrly in the treatment of colorectal cancer, breast cancer, gastric cancer, prostate cancer and non-small-cell lung cancer.

Specifically, the following combinations are particualrly preferred for colorectal cancer: Panorex in combination with: UFT (optionally with Leucovorin); Capecitabine; Oxaliplatin (optionally with 5FU); CPT-II, 5FU (optionally with Eniluracil or Levamisole or Leucovorin); 5FU protacted continuous infusion; and Mitomycin.

Preferred combinations for the treatment of breast cancer are: Panorex in combination with Paclitaxel; Docetaxel; Cyclophosphamide (optionally with 5FU and either Methotrexate or Doxorubicin); Navelbine (iv and/or oral); Doxorubicine; Epirubicin; Mitoxantrone; and Raloxifin.

Preferred combinations for the treatment of gastric cancer are: Panorex in combination with Cisplatin; 5FU; Mitomycin; and Carboplatinum.

A preferred combination for the treatment of prostatic cancer is: Panorex in combination with Mitoxantrone.

Preferred combinations for the treatment of non-small-cell lung cancer are: Panorex in combination with: Navelbine; Cisplatin; Carboplatin; Paclitaxel; Docetaxel; Gemcitabine; Topotecan; and Etoposide.

Information regarding dosing of Panorex and the above chemotherapeutic agents given in combination with Panorex can be found in standard reference books such as ABPI, Compendium of Data Sheets and Summaries of Product Characteristics, Datapharm Publications Limited, 1998-1999.

The compositions include those suitable for oral, rectal, nasal, topical (including buccal and sublingual), vaginal, parenteral (including subcutaneous, intramuscular, intravenous and intradermal) or transdermal administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the chemotherapeutic agent suitable for oral administration may be presented as discrete units such as capsules, cachets or tablets each containing a predetermined amount of the active ingredient; as a powder or granules; as a solution or suspension in an aqueous or non-aqueous liquid; or as an oil-in-water-liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricants, inert diluent, preservative, disintegrant (eg. sodium starch glycollate, cross-linked povidone, cross-linked sodium carboxymethyl cellullose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating to provide release in parts of the gut other than the stomach.

Compositions suitable for oral use as described above may also include buffering agents designed to neutralise stomach acidity. Such buffers may be chosen from a variety of organic or inorganic agents such as weak acids or bases admixed with their conjugated salts.

Composition suitable for topical administration in the mouth include lozenges comprising the active ingredient in a flavoured basis, usually sucrose and acacia or tragacanth; pastilles comprising the active ingredient in an inert basis such as gelatine and glycerin, or sucrose and acacia and mouthwashes comprising the active ingredient in a suitable carrier.

Compositions for rectal administration may be presented as a suppository with suitable base comprising for example cocoa butter or a salicylate.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bacteriostats and solutes which render the compositions isotonic with the blood of the intended recipient; and aqueous and non-aqueous sterile suspensions which may include suspending agents and thickening agents, such as liposomes or other microparticulate systems which are designed to target the compounds to blood components or one or more organs. The compositions may be presented in unit-dose or multi-dose sealed containers, for example, ampoules and vials, and may be stored in a freeze-dried(lyophilized) condition requiring only the addition of sterile liquid carrier, for example water for injections, immediately prior to use. Extemporaneous injection solutions and suspensions may be prepared from sterile powders, granules and tablets of the kind previously described.

Compositions suitable for transdermal administration may be presented as discrete patches adapted to remain in intimate contact with the epidermis of the recipient for a prolonged period of time. Such patches suitably contain the active ingredient as an optionally buffered, aqueous solution of, for example, 0.1 0.2M concentration with respect to said compound. As one particular possibility, the active ingredient may be delivered from the patch by iontophoresis as generally described in Pharmaceutical Research, 3 (6), 318 (1986).

It should be understood that in addition to the ingredients particularly mentioned above the compositions in question, for example, those suitable for oral administration may include such further agents as sweeteners, thickeners and flavouring agents.

The dosage range of the chemotherapeutic agent to be co-administered with the antibody may typically be between about 1 to 1000 mg/M$^2$ (based on patient body surface area) or about 2-30 mg/kg (based on patient body weight), depending on the chemotherapeutic agent(s) used. Thus, for example, vinorelbine (navelbine) would typically be administered at a dosage of about 20 to 30 mg/m$^2$, cisplatin at about 15 to 100 mg/m$^2$ carboplatin at about 300 to 600 mg/m$^2$ and paclitaxel at about 100 to 300 mg/m$^2$, preferably around 135 to 175 mg/m$^2$. Another way of expressing dosage is by their AUC value. For example carboplatin would typically be administered at a dose calculated as AUC=4 to 6 mg/ml-min. Generally, the doses of chemotherapeutic agents are lower when given in combination with another chemotherapeutic agent and/or antibody than if given on their own as the single chemotherapeutic agent. The doses of chemotherapeutic agents that will be co-administered with anti Ep-CAM antibody(ies) will likely be the standard doses for the type of carcinoma treated or lower doses. In general the highest tolerated doses of the chemotherapeutic agents are administered either alone or in combination.

The anti-Ep-CAM antibodies of the present invention preferably have the structure of a natural antibody or a fragment thereof. Antibodies typically comprise two heavy chains linked together by disulphide bonds and two light chains. Each light chain is linked to a respective heavy chain by disulphide bonds. Each heavy chain has at one end a variable domain followed by a number of constant domains. Each light chain has a variable domain at one end and a constant domain at its other end. The light chain variable domain is aligned with the variable domain of the heavy chain. The light chain constant domain is aligned with the first constant domain of the heavy chain. The constant domains in the light and heavy chains are not involved directly in binding the antibody to antigen.

The variable domains of each pair of light and heavy chains form the antigen binding site. The domains on the light and heavy chains have the same general structure and each domain comprises a framework of four regions, whose sequences are relatively conserved, connected by three complementarity determining regions (CDRs). The four framework regions largely adopt a beta-sheet conformation and the CDRs form loops connecting, and in some cases forming part of the beta-sheet structure. The CDRs are held in close proximity by the framework regions and with the CDRs from the other domain, contribute to the formation of the antigen binding site, which in the case of the present invention is the formation of an anti-Ep-CAM binding site. CDRs and framework regions of antibodies may be determined by reference to Kabat et al ("Sequences of proteins of immunological interest" U.S. Dept. of Health and Human Services, U.S. Government Printing Office, 1987).

The preparation of an antibody in which the CDRs are derived from a different species than the framework of the antibody's variable domains is disclosed in EP-A-0239400. The CDR's may be derived from a rodent or primate monoclonal antibody. The framework of the variable domains and the constant domains of such altered antibodies are usually derived from a human antibody. Such a humanised antibody should not elicit as great an immune response when administered to a human compared to the immune response mounted by a human against a wholly foreign antibody such as one derived from a rodent.

The antibody preferably has the structure of a natural antibody or a fragment thereof. Throughout the specification reference to antibody therefore comprises not only a complete antibody but also fragments such as a (Fab') 2 fragment, a Fab fragment, a light chain dimer or a heavy chain dimer. The antibody may be an IgG such as IgG$_1$, IgG$_2$, IgG$_3$ or IgG$_4$; or IgM, IgA, IgE or IgD or a modified variant thereof, including those that may be conjugated to other molecules such as radionuclides, enzymes etc. Typically, the constant region is selected according to the functionality required. Normally an IgG1 will demonstrate lytic ability through binding to complement and will mediate ADCC (antibody dependent cell cytotoxicity). An IgG$_4$ antibody will be preferred if a non-cytotoxic antibody is required. Antibodies according to the present invention also include bispecific antibodies such as, for example, the 17-1A antibody disclosed in Mack et al, The Journal of Immunology, 1997, 158: 3965-3970. Antibodies of the present invention may be murine, chimaeric or humanised with the preferred antibody being humanised antibody.

There are four general steps to humanise a monoclonal antibody. These are:
(1) determining the nucleotide and predicted amino acid sequence of the starting antibody light and heavy variable domains;
(2) designing the humanised antibody, i.e. deciding which antibody framework region to use during the humanising process;
(3) the actual humanising methodologies/techniques; and
(4) the transfection and expression of the humanised antibody.

More specifically,

Step 1: Determining the Nucleotide and Predicted amino acid sequence of the Antibody Light and Heavy Chain Variable Domains To humanise an antibody only the amino acid sequence of the antibody's heavy and light chain variable domains needs to be known. The sequence of the constant domains is irrelevant because these do not contribute to the reshaping strategy. The simplest method of determining an antibody variable domain amino acid sequence is from cloned cDNA encoding the heavy and light variable domain.

There are two general methods for cloning a given antibody's heavy and light chain variable domain cDNAs: (1) via a conventional cDNA library, or (2) via the polymerase chain reaction (PCR). Both of these methods are widely known. Given the nucleotide sequence of the cDNAs, it is a simple matter to translate this information into the predicted amino acid sequence of the antibody variable domains.

Step 2: Designing the Humanised Antibody

There are several factors to consider in deciding which human antibody sequence to use during the humanisation. The humanisation of light and heavy chains are considered independently of one another, but the reasoning is basically similar for each.

This selection process is based on the following rationale: a given antibody's antigen specificity and affinity is primarily determined by the amino acid sequence of the variable region CDRs. Variable domain framework residues have little or no direct contribution. The primary function of the framework regions is to hold the CDRs in their proper spatial orientation to recognise the antigen. Thus the substitution of rodent CDRs into a human variable domain framework is most likely to result in retention of their correct spatial orientation if the human variable domain framework is highly homologous to the rodent variable domain from which they originated. A human variable domain should preferably be chosen therefore that is highly homologous to the rodent variable domain(s).

A suitable human antibody variable domain sequence can be selected as follows:
1. Using a computer program, search all available protein (and DNA) databases for those human antibody variable domain sequences that are most homologous to the rodent antibody variable domains. The output of a suitable program is a list of sequences most homologous to the rodent antibody, the percent homology to each sequence, and an alignment of each sequence to the rodent sequence. This is done independently for both the heavy and light chain variable domain sequences. The above analyses are more easily accomplished if only human immunoglobulin sequences are included.
2. List the human antibody variable domain sequences and compare for homology. Primarily the comparison is performed on lengths of CDRs, except CDR 3 of the heavy chain which is quite variable. Human heavy chains and Kappa and Lambda light chains are divided into subgroups; Heavy chain 3 subgroups, Kappa chain 4 subgroups, Lambda chain 6 subgroups. The CDR sizes within each subgroup are similar but vary between subgroups. It is usually possible to match a rodent antibody CDR to one of the human subgroups as a first approximation of homology. Antibodies bearing CDRs of similar length are then compared for amino acid sequence homology, especially within the CDRs, but also in the surrounding framework regions. The human variable domain which is most homologous is chosen as the framework for humanisation.

Step 3: The Actual Humanising Methodologies/Techniques

An antibody may be humanised by grafting the desired CDRs onto a human framework according to EP-A-0239400. (see also P. T. Jones et al, Nature 321: 522 (1986); L. Reichman et al, Nature 332: 323 (1988); Verhoeyen M. et al, Science 239: 1534 (1988) and J. Ellis et al, The Journal of Immunology, 155: 925-937 (1995)). A DNA sequence encoding the desired reshaped antibody can therefore be made beginning with the human DNA whose CDRs it is wished to reshape. The rodent variable domain amino acid sequence containing the desired CDRs is compared to that of the chosen human antibody variable domain sequence. The residues in the human variable domain are marked that need to be changed to the corresponding residue in the rodent to make the human variable region incorporate the rodent CDRs. There may also be residues that need substituting in, adding to or deleting from the human sequence.

Oligonucleotides are synthesised that can be used to mutagenise the human variable domain framework to contain the desired residues. Those oligonucleotides can be of any convenient size. One is normally only limited in length by the capabilities of the particular synthesiser one has available. The method of oligonucleotide-directed in vitro mutagenesis is well known.

Alternatively humanisation may be achieved using the recombinant polymerase chain reaction (PCR) methodology of WO92/07075. Using this methodology, a CDR may be spliced between the framework regions of a human antibody.

In general, the technique of WO92/07075 can be performed using a template comprising two human framework regions, AB and CD and between them, the CDR which is to be replaced by a donor CDR. Primers A and B are used to amplify the framework region AB, and primers C and D used to amplify the framework region CD. However, the primers B and C each also contain, at their 5' ends, an additional sequence corresponding to all or at least part of the donor CDR sequence. Primers B and C overlap by a length sufficient to permit annealing of their 5' ends to each other under conditions which allow a PCR to be performed. Thus, the amplified regions AB and CD may undergo gene splicing by overlap extension to produce the humanised product in a single reaction.

Step 4: The Transfection and Expression of the Reshaped Antibody

Following the mutagenesis reactions to reshape the antibody, the mutagenised DNAs can be linked to an appropriate DNA encoding a light or heavy chain constant region, cloned into an expression vector, and transfected into host cells, preferably mammalian cells. These steps can be carried out in routine fashion. A reshaped antibody may therefore be prepared by a process comprising
(a) preparing a first replicable expression vector including a suitable promoter operably linked to a DNA sequence which encodes at least a variable domain of an Ig heavy or light chain, the variable domain comprising framework regions from a human antibody and the CDRs required for the humanised antibody of the invention.
(b) preparing a second replicable expression vector including a suitable promoter operably linked to a DNA sequence which encodes at least the variable domain of a complementary Ig light or heavy chain respectively;
(c) transforming a cell line with the first or both prepared vectors; and
(d) culturing said transformed cell line to produce said altered antibody.

Preferably the DNA sequence in step (a) encodes both the variable domain and the or each constant domain of the human antibody chain. The humanised antibody can be recovered and purified. The cell line which is transformed to produce the altered antibody may be Chinese Hamster Ovary (CHO) cell line or an immortalised mammalian cell line, which is advantageously of lymphoid origin, such as a myeloma, hybridoma, trioma or quadroma cell line. The cell line may also comprise a normal lymphoid cell, such as a B-cell, which has been immortalised by transformation with a virus, such as the Epstein-Barr virus. Most preferably, the immortalised cell line is a myeloma cell line or a derivative thereof. The expression system of choice is the glutamine synthetase expression system described in WO87/00462 (see also P. E. Stephens et al, Nucleic Acid Res. 17: 7110 (1989) and C. R. Bebbington et al, Bio/Technology 10: 169 (1992)).

Although the cell line used to produce the humanised antibody is preferably a mammalian cell line, any other suitable cell line, such as a bacterial cell line or a yeast cell line, may alternatively be used. For single antibody chains, it is envisaged that E. coli—derived bacterial strains could be used. The antibody obtained is checked for functionality. If functionality is lost, it is necessary to return to step (2) and alter the framework of the antibody.

Once expressed, the whole antibodies, their dimers, individual light and heavy chains, or other immunoglobulin forms of the present invention can be purified according to standard procedures of the art, including ammonium sulfate precipitation, affinity columns, column chromatography, gel electrophoresis and the like (see generally Scopes, R, Protein Purification, Springer-Verlag, N.Y. (1982)). Substantially pure immunoglobulins of at least about 90 to 95% homogeneity are preferred and 98 to 99% or more homogeneity most preferred, for pharmaceutical uses. Once purified, partially or to homogeneity as desired, an antibody may then be used therapeutically.

Antibodies are typically provided as a pharmaceutical composition comprising a pharmaceutically acceptable carrier or diluent and, as active ingredient, an antibody according to the invention. The antibody and pharmaceutical compositions thereof are particularly useful for parenteral administration i.e. subcutaneously, intramuscularly or intravenously.

The compositions for parenteral administration will commonly comprise a solution of the antibody or a cocktail thereof dissolved in an acceptable carrier, preferably an aqueous carrier. A variety of aqueous carriers can be used, eg. sterile water for injection, 0.9% sodium chloride in water, 5% dextrose in water and Lactated Ringers solution. These solutions are sterile and generally free of particulate matter. These compositions may be sterilised by conventional, well known sterilisation techniques. The compositions may contain pharmaceutically acceptable auxiliary substances as required to approximate physiological conditions such as pH adjusting and buffering agents, toxicity adjustment agents and the like, for example sodium acetate, sodium chloride, potassium chloride, calcium chloride, sodium lactate, etc. The concentration of antibody in these formulations can vary widely, for example from less than about 0.5%, usually at or at least about 1% to as much as 15 or 20% by weight and will be selected primarily based on fluid volumes, viscosities, etc. in accordance with particular mode of administration selected.

Thus, a typical pharmaceutical composition for intramuscular injection could be made to contain 1 ml sterile buffered water, and 50 mg of antibody. A typical composition for intravenous infusion could be made up to contain 250 ml of sterile Ringers solution and 150 mg of antibody. Actual methods for preparing parenterally administrable compositions will be known or apparent to those skilled in the art, particularly, those trained in the preparation of parenteral products and are described in more detail in, for example, *Remmington's Pharmaceutical Science,* 15th Ed., Mack Publishing Company, Easton, Pa. (1990).

The antibodies of this invention can be lyophilised for storage and reconstituted in a suitable carrier prior to use. This technique has been shown to be effective with conventional immunoglobulins. Any suitable lyophilisation and reconstitution techniques can be employed. It will be appreciated by those skilled in the art that lyophilization and reconstitution can lead to varying degrees of antibody activity loss (eg. with conventional immune globulins, IgM antibodies tend to have greater activity loss than IgG antibodies) and that use levels may have to be adjusted to compensate.

The dosage range of the antibody in accordance with the invention is about 0.5 to 1000 mg/m$^2$, preferably about 0.5 to 250 mg/m$^2$, more preferably, between 0.5 and 100 mg/m$^2$ and 0.5 and 50 mg/m$^2$ and most preferably between 5 and 25 mg/m$^2$ such as for example, 15 mg/m$^2$.

Similarly, expressed in mg per dose, the dosages of the antibody may be about 1 to 2000 mg per dose, preferably about 1 to 500 mg per dose, more preferably between 1 to 200 mg per dose and between 1 to 100 mg per dose and most preferably between 10 and 50 mg per dose such as, for example 30 mg per dose.

Single or multiple administrations of the compositions can be carried out with dose levels and pattern being selected by the treating physician. In any event, the pharmaceutical formulations should provide a quantity of the antibody(ies) sufficient to effectively treat the patient.

Typically, the chemotherapeutic agent and antibody will be presented as separate pharmaceutical compositions for co-administration, but they may also be formulated as a single pharmaceutical formulation. In this way both the antibody and the chemotherapeutic agent are presented to the patient within one and the same composition.

One or more distinct chemotherapeutic agents and one or more distinct anti-Ep-CAM antibodies may be co-administered in all aspects of the present invention. Thus reference to a chemotherapeutic agent comprises one or more distinct chemotherapeutic agent(s). If there is more than one chemotherapeutic agent, these may be administered either individually each on its own and/or together as a chemotherapeutic agent cocktail. Similarly, reference to antibody comprises one or more distinct anti-Ep-CAM antibody(ies). If there is more than one antibody, these may again be administered either individually each on its own and/or together as a cocktail. Additionally, the chemotherapeutic agent(s) are typically administered separately from the antibody(ies) but they may also be administered together as a chemotherapeutic agent(s)/antibody(ies) cocktail.

Co-administration of the chemotherapeutic agent/radiotherapy with the antibody comprehends administration substantially simultaneously of both the chemotherapeutic agent/radiotherapy and the antibody. Essentially, the rational behind co-administration is to allow sufficient exposure of Ep-CAM expressing tumour cells to a chemotherapeutic agent/radiotherapy known to block cell cycle progression at $G_2$/M to achieve the desired increase in Ep-CAM antigen density prior to exposure of the same tumour cells to an anti-Ep-CAM antibody thereby achieving greater targeting of anti-Ep-CAM antibodies to Ep-CAM expressing tumours. Co-administration therefore comprises any mode of administering a chemotherapeutic agent/radiotherapy in conjunction with an anti-Ep-CAM antibody that will achieve this result. Throughout the specification the term "combination of an anti-Ep-CAM antibody with a chemotherapeutic agent" refers to one wherein the chemotherapeutic agent/radiotherapy and the anti-Ep-CAM antibody have been co-administered.

Preferably the chemotherapeutic agent is administered simultaneously with the antibody or more preferably before the antibody. Thus the chemotherapeutic agent may be administered on the same day as the antibody, either together or within hours of each other but may also be administered up to about two months beforehand, typically, about one or two weeks beforehand and more typically less than a week beforehand, say one to three days beforehand.

Additionally, co-administration also includes administering more than one dose of antibody within several weeks after one or more doses of chemotherapeutic agent, in other words the chemotherapeutic agent need not be re-administered again with every subsequent administration of the antibody, but may be administered just once or intermittently during the course of antibody treatment. Co-administration also comprises administration of the chemotherapeutic agent up to 3 weeks after the antibody, preferably within a week and more preferably within a few days such as one to five days.

The antibody may be administered several times daily. Similarly the chemotherapeutic agent may be infused continuously over several hours or even days.

The present invention also provides a method of treating mammalian patients, preferably humans, afflicted with cancer which comprises co-administering a chemotherapeutic agent which is capable of arresting Ep-CAM antigen expressing cells in $G_2/M$ in combination with an anti-Ep-CAM antibody. Preferably, the chemotherapeutic agent is given simultaneously and more preferably prior to administration of the antibody.

The cancers which may be treated particularly effectively with this combination therapy are primary or metastatic cancers of any histologic or histogenetic origin that express the Ep-CAM antigen. This includes, for example, prostate cancers, lung cancers, breast cancers, colon cancers, pancreatic cancers and ovarian cancers.

Dosing schedules for the treatment method of the present invention can be adjusted to account for the patient characteristics, disease state, characteristics of the chemotherapeutic agent and characteristics of the anti-Ep-CAM antibody. The goal of dosing schedules under this invention will be to administer anti-Ep-CAM antibody in a manner that will expose the Ep-CAM expressing tumour cells to the anti-Ep-CAM antibody at a time when antigen expression is likely to be increased due to exposure to chemotherapy which is known to block cell cycle progression at $G_2/M$. Additionally, as much as possible a dosing schedule convenient for the patient must be maintained.

Preferred dosing schedules for administration of the anti-Ep-CAM antibody and chemotherapy include: administering the anti-Ep-CAM antibody once every one or two weeks, preferably once every three or four weeks or a combination thereof for as long as necessary. The chemotherapeutic agent is given according to the established regimen for that agent or a regimen which will allow exposure of Ep-CAM expressing tumour cells to be arrested in $G_2/M$. Preferred dosing schedules vary with the chemotherapy agent and disease state but include, for example, once weekly, once every three or four weeks, or daily for several (e.g. 3-5) days repeated every three or four weeks for as long as necessary. Dosing of the anti-Ep-CAM antibody may take place on the same day or different days as indicated for the chemotherapeutic agent. Adjustment of the dosing schedule or strength of dose to prevent or decrease toxicity or side effects may take place with either the anti-Ep-CAM antibody or the chemotherapy agent.

For example, the preferred dosing schedule for co-administration of vinorelbine and cisplatin in combination with humanised 323/A3 ($IgG_1$) is administration of humanised 323/A3 ($IgG_1$) at a dose of 30 mg/m$^2$ once a week for as long as necessary but typically for a period of 3 to 4 weeks, followed by a 30 mg/m$^2$ dose every other week thereafter for as long as necessary. Vinorelbine is administered at a dose 25 mg/m$^2$ on day 1, 8, 15 and 22. Cisplatin is given only once at a dose of 100 mg/m$^2$ on day 1. Thereafter the vinorelbine/cisplatin regime is repeated every 28 days for as long as necessary. Preferably, vinorelbine, cisplatin and humanised 323/A3 ($IgG_1$) are administered at the same time on day one over a period of about 2 to 3 hours.

Another example of a preferred dosing schedule is the administration of paclitaxel/carboplatin in combination with humanised 3231A3 ($IgG_1$), wherein 323/A3 ($IgG_1$) is administered as for the vinorelbine/cisplatin example above and paclitaxel and carboplatin are given at a dose of 225 mg/m$^2$ and AUC=6.0 respectively, on day 1, with a repeat dosage every 28 days thereafter for as long as necessary. Again, paclitaxel, carboplatin and humanised 323/A3 ($IgG_1$) are preferably administered together on day 1 over a period of about 2 to 3 hours.

Other preferred dosage schedules which comprise the combination of 323/A3 ($IgG_1$) with any of navelbine, cisplatin or taxol on their own would comprise similar dosages and administration schedules, using just one anticancer agent instead of two.

When the preferred anti-Ep-CAM antibody is Panorex, the dosage of antibody is between 10 to 500 mg per dose, preferably 100 mg per dose.

A further aspect of the present invention is a method of increasing antibody binding of anti-Ep-CAM antibodies to Ep-CAM expressing cells by co-administering to a patient a chemotherapeutic agent capable of arresting cells in $G_2/M$ together with said anti-Ep-CAM antibody.

By co-administering a chemotherapeutic agent according to the present invention together with an Ep-CAM antibody, it is possible to increase antibody binding by about 2 to 10 fold, preferably by more than 4 fold, more preferably by more than 6 fold and most preferably by more than 8 fold.

FIGURES

FIG. 1.

Ep-CAM is expressed across the cell cycle, but at higher density and greater homogeneity on cells in S (dotted line) and in $G_2/M$ (dashed line) phases than in $G_0/G_1$ cells (solid line). This pattern of expression has been documented in a number of other human colon, prostate, and lung tumour cell lines.

FIG. 2.

Cell cycle arrest is a prominent feature of adenocarcinoma cells exposed in vitro to Navelbine (NVB; 30 nM) plus Cisplatin (CDDP; 5 µM), or Taxol (TAX; 80 nM) plus Carboplatin (CPBDA; 100 µM), compared to media alone, 5-Fluorouracil (5FU), interferon-alpha (IFN-alpha; 100 U/ml), or interferon-gamma (IFN-gamma; 100 U/ml). The area of each bar is divided to indicate the percentage of cells in $G_0/G_1$ and in $S+G_2/M$ phases; the height of each bar indicates the average number of Ep-CAM molecules per cell within the population. Cells in S phase and in $G_2/M$ phase express higher levels of Ep-CAM (FIG. 1), and the agents which blocked cell cycle progression had overall increased Ep-CAM expression

FIG. 3.

The expression of Ep-CAM antigen was quantified on a variety of adenocarcinoma cell lines as well as primary cultures of normal human cells. Cultured cells were exposed sequentially to media, or to 30 nM Navelbine followed by 5 µM Cisplatin (NVB+CDDP), or to 80 nM Taxol followed by 100 µM Carboplatin (TAX+CPBDA). The 4 adenocarcinoma cells expressed higher antigen levels subsequent to exposure to cycle-specific drug combinations, whereas the 4 normal cells did not show any increase in antigen expression, which remained undetectable in 2 of the normal cell populations.

FIG. 3a.

The binding of Panorex, a related murine monoclonal antibody with specificity for the Ep-CAM antigen, was evaluated after a 15 minute incubation with HT29 adenocarcinoma cells which had been cultured with Navelbine plus Cisplatin or with Taxol as previously described. A significant increase (34%) in antibody binding was seen on the cells treated with Navelbine plus Cisplatin; 82% of these cells were arrested in S or $G_2$/M cycle phase compared to 21% of the control cells. (A smaller increase (8%) in antibody binding was seen for cells treated with Taxol, but in this experiment only 57% of the cells were cycle-arrested) as is shown in FIG. 3a.

FIG. 4.

The ability of human peripheral blood ADCC effector cells to lyse tumour target cells incubated with humanized 323/A3 ($IgG_1$) (a humanized monoclonal antibody having specificity for the Ep-CAM antigen and capable of interacting with Fc receptors on human effector cells) in vitro was improved when the target cells had been pre-treated with NAVELBINE (30 nM) plus Cisplatin (5 µM).

FIG. 5.

Treatment of human tumour xenograft-bearing mice with a cell-cycle-specific cytotoxic agent promoted improved localization of antibody specific for Ep-CAM to the tumours.

FIG. 6. Humanised 323/A3 ($IgG_1$) Kappa Light Chain Amino Acid Sequence SEQ ID NO:11

FIG. 7. Humanised 323/A3 ($IgG_1$) Heavy Chain Amino Acid Sequence SEQ ID NO:12

Figure 8:
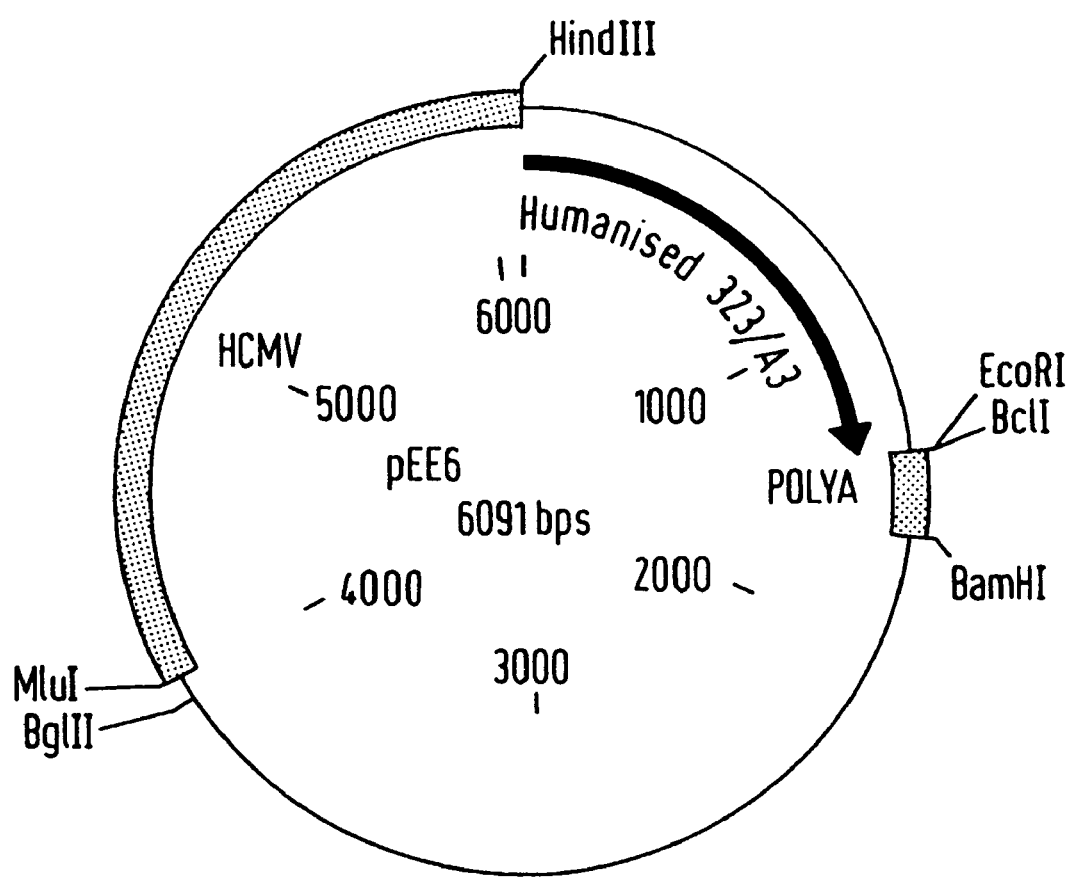

FIG. 8. Vector Map of pEE6

Figure 9:
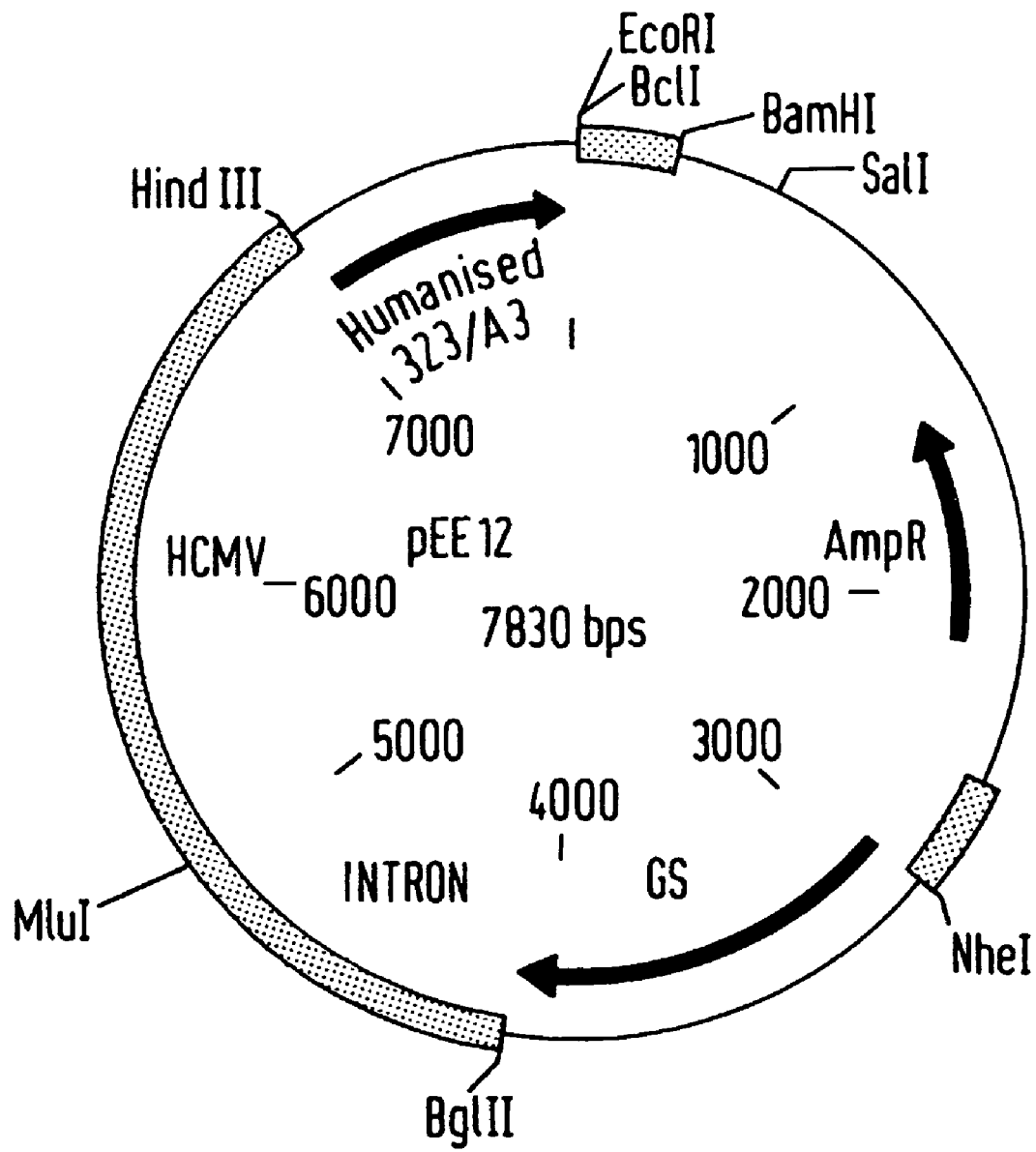

FIG. 9. Vector Map of pEE12

Figure 10:
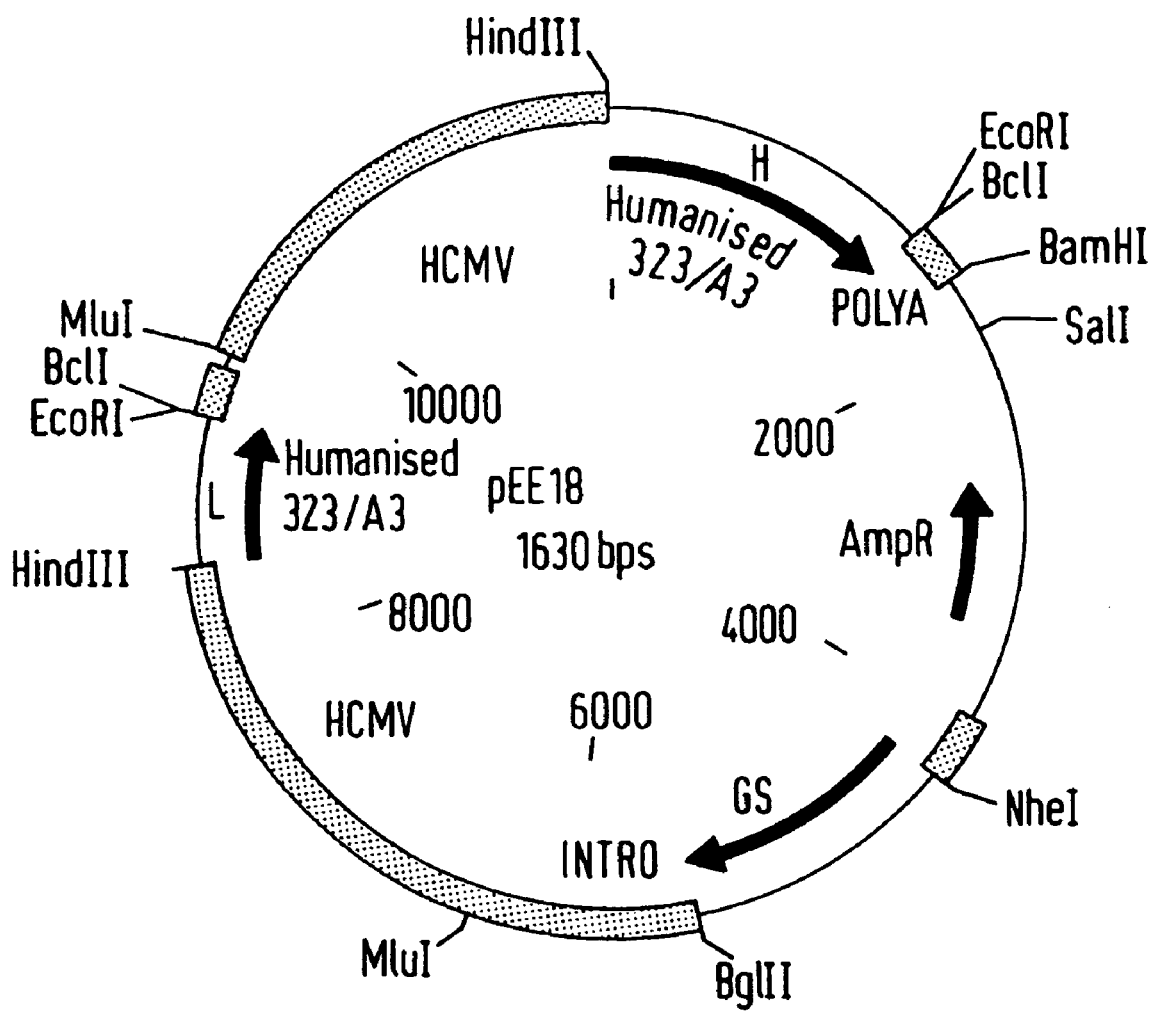

FIG. 10. Vector Map of pEE18

FIG. 11. Humanised 323/A3 ($IgG_{4cys}$) Kappa Light Chain Amino Acid Sequence SEQ ID NO:13

FIG. 12. Humanised 323/A3 ($IgG_{4cys}$) variant Heavy Chain Amino Acid Sequence SEQ ID NO:14

FIG. 13. Humanised 323/A3 ($IgG_{2cys}$) Kappa Light Chain Amino Acid Sequence SEQ ID NO:15

FIG. 14. Humanised 323/A3 ($IgG_{2cys}$) Heavy Chain Amino Acid Sequence SEQ ID NO:16

FIG. 15. Humanised 323/A3 ($IgG_1$) light chain cDNA Sequence (also 323/A3 ($IgG_{4cys}$ and $IgG_{2cys}$ light chain cDNA sequence) and corresponding amino acid sequence, SEQ ID NO:1, SEQ ID NO:2 and SEQ ID NO:3

FIG. 16. Humanised 323/A3 ($IgG_1$) Heavy chain cDNA Sequence and corresponding amino acid sequence, SEQ ID NO:4 and SEQ ID NO:5

FIG. 17. Humanised 323/A3 ($IgG_4$) heavy chain cDNA Sequence and corresponding amino acid sequence, SEQ ID NO:6 and SEQ ID NO:7

FIG. 18. Humanised 323/A3 ($IgG_{2cys}$) heavy chain cDNA Sequence and corresponding amino acid sequence, SEQ ID NO:8, SEQ ID NO:9 and SEQ ID NO:10

The following examples illustrate the invention.

EXAMPLE 1

Ep-CAM Antigen Expression Varied by Phase Across the Cell Cycle on PC-3 Prostatic Adenocarcinoma Cells Populations of PC-3 prostatic adenocarcinoma cells were evaluated for distribution in $G_0/G_1$, S, and $G_2$/M phases of the cell cycle as well as Ep-CAM expression. Cells were gently trypsinized and mechanically detached from the culture flasks and resuspended in calcium-and magnesium-free phosphate-buffered saline containing bovine serum albumin and $NaN_3$. Exactly $2 \times 10^5$ cells were stained with FITC-323/A3 murine IgG antibody or FITC-murine IgG (control). Cells were fixed with cold paraformaldehyde, then permeabilized for DNA staining with Tween-20. Cellular DNA was stained with propidium iodide and RNase A. Listmode data were acquired on a FACScan flow cytometer (Becton Dickinson Immunocytometry Systems) equipped with a 488 nm laser using Cell Fit software. Cell cycle analysis was done using SOBR modelling (where possible, otherwise manual estimations were employed) on Cell Fit. EP-CAM antigen expression as detected by 323/A3 binding was evaluated separately using histogram analysis in Win List (Verity Software House).

FIG. 1 shows that Ep-CAM is expressed across the cell cycle, but at higher density and greater homogeneity on cells in S (dotted line) and in $G_2$/M (dashed line) phases than in $G_0/G_1$ cells (solid line). This pattern of expression has been documented in a number of other human colon, prostate, and lung tumor cell lines.

EXAMPLE 2

Figure 2:
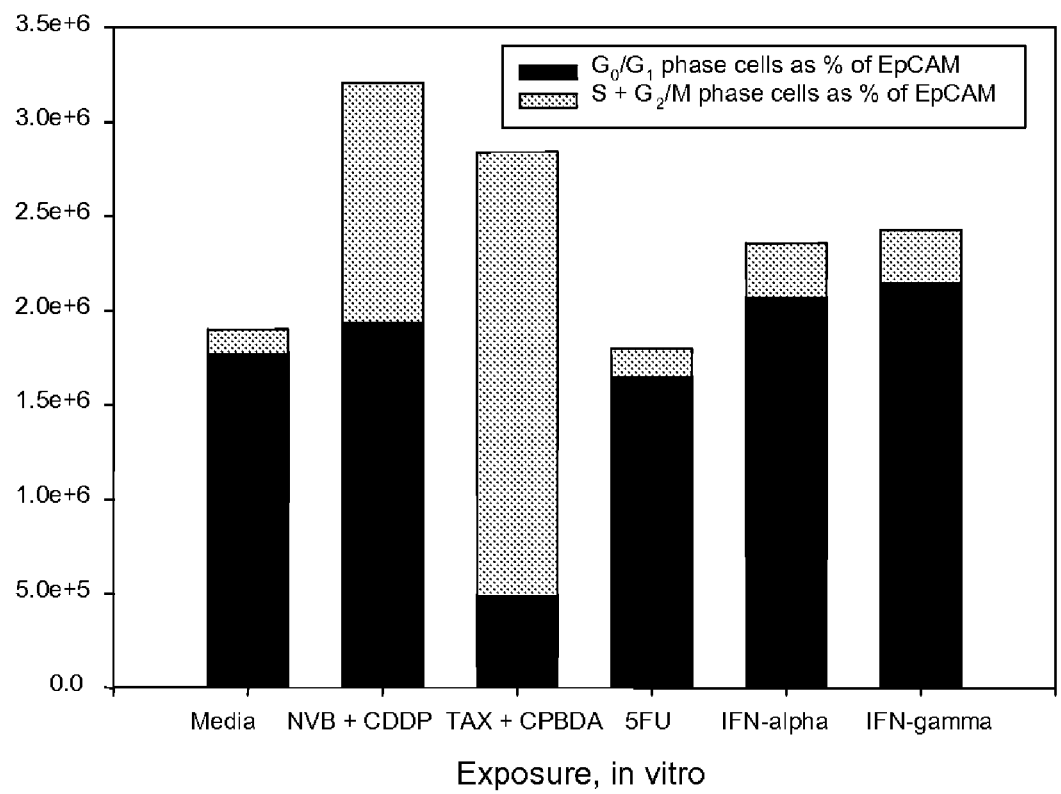

Increased Expression of Ep-CAM Antigen on Adenocarcinoma Cells was Associated with Arrest of Cell Cycle Progression and Accumulation of Cells in S and $G_2$/M Phases Adenocarcinoma cell lines were exposed to the various drugs or combinations of drugs as indicated in FIG. 2. Subconfluent cells were exposed to Navelbine or Taxol for up to 24 hours, then washed and exposed to Cisplatin or Carboplatin, respectively, overnight. Cells were exposed to 5FU for 24 hours, and for 2-5 days to the interferons. Cells were washed and cultured for another 2-5 days prior to analysis for antigen expression and cell cycle status as described in Example 1. Antigen expression was quantified by comparison of the binding of fluorescein-conjugated 323/A3 to cultured cells with binding to calibrated microbead standards.

Cell cycle analysis demonstrated that only 6.3% of the media control cells were in S and $G_2$/M phases combined, compared to 39.4% of NVB+CDDP and 82.6% of TAX+ CPBDA cells, both combinations of which caused significant increases in Ep-CAM antigen expression (as demonstrated in FIG. 2). Antigen expression was not significantly increased in cells exposed to 5FU, IFN-α, or IFN-γ, which had only 7.9%, 12%, and 11.5%, respectively, of cells in S+$G_2$/M phase. Thus, only the drugs which caused accumulation of cells in S or $G_2$/M phases were able to cause a significant increase in Ep-CAM antigen expression.

EXAMPLE 2a

The binding of Panorex, a related murine monoclonal antibody with specificity for the Ep-CAM antigen, was evaluated after a 15 minute incubation with HT29 adenocarcinoma cells which had been cultured with Navelbine plus Cisplatin or with Taxol as previously described. A significant increase (34%) in antibody binding was seen on the cells treated with Navelbine plus Cisplatin; 82% of these cells were arrested in S or $G_2$/M cycle phase compared to 21% of the control cells. (A smaller increase (8%) in antibody binding was seen for cells treated with Taxol, but in this experiment only 57% of the cells were cycle-arrested) as is shown in FIG. 3a.

EXAMPLE 3

Increased Ep-CAM Antigen Expression was Observed on Tumour Cells but not Normal Cells Exposed to Cytotoxic Drugs In Vitro The expression of Ep-CAM antigen was quantified on a variety of adenocarcinoma cell lines as well as primary cultures of normal human cells. Cultured subconfluent cells were exposed sequentially to media, or to 30 nM Navelbine followed by 5 µM Cisplatin (NVB+CDDP), or to 80 nM Taxol followed by 100 μM Carboplatin (TAX+CPBDA). Cells were washed with media and cultured for another 2-5 days prior to analysis for antigen expression as described in Examples 1 and 2.

Figure 3:
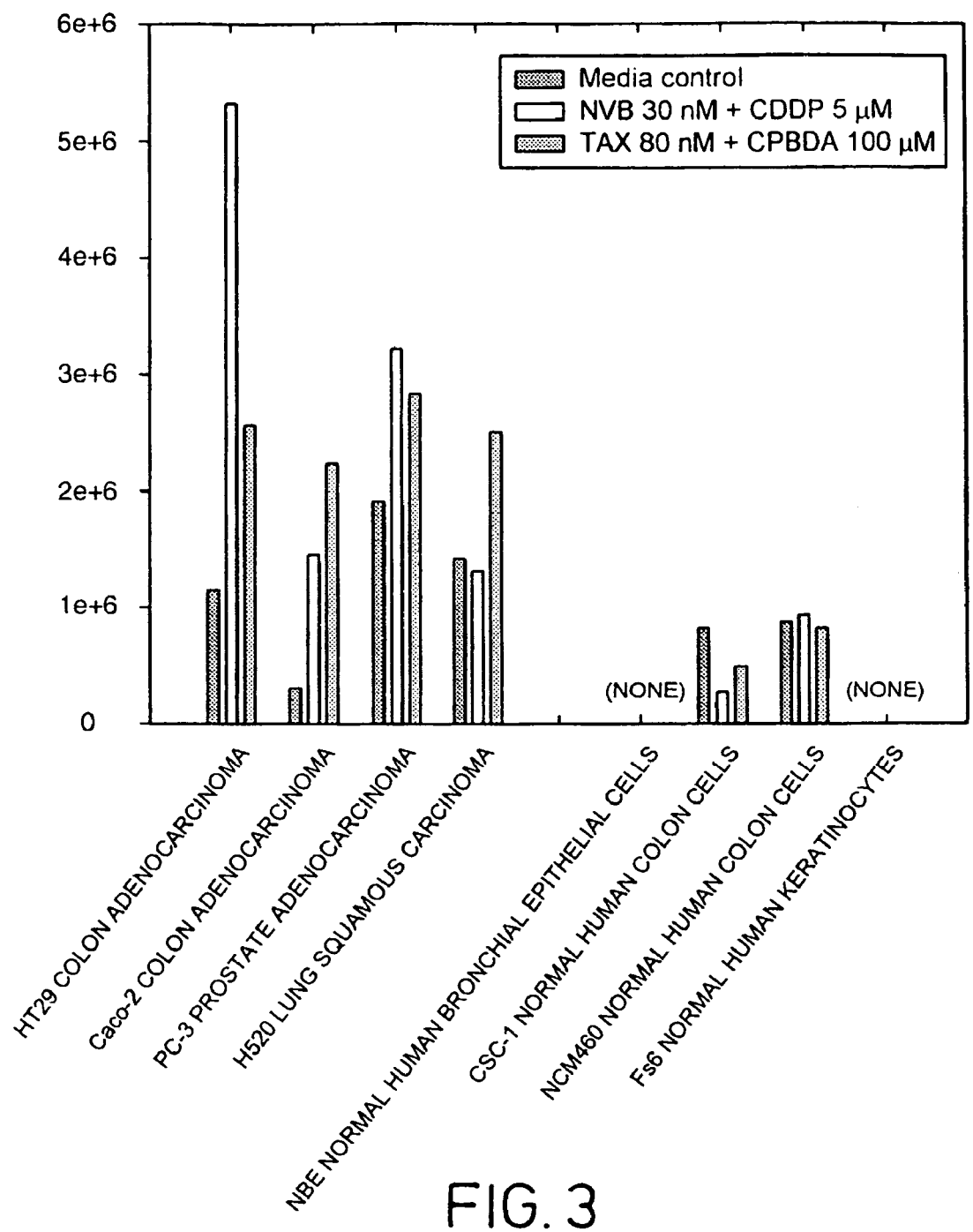
Figure 3A:
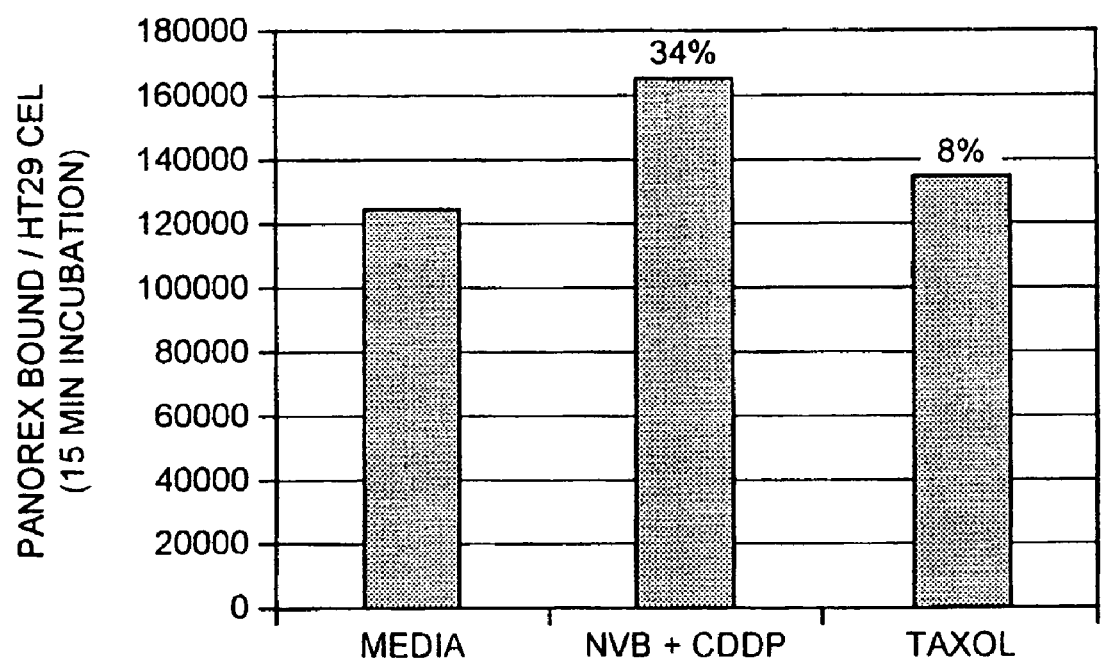

FIG. 3 clearly shows that the 4 adenocarcinoma cells expressed higher antigen levels subsequent to exposure to cycle-specific drug combinations, whereas the 4 normal cells did not show any increase in antigen expression, which remained undetectable in 2 of the normal cell populations.

EXAMPLE 4

Cells Exposed to NAVELBINE Plus Cisplatin were Better Targets for Human ADCC Activity than Control Cells Adenocarcinoma cells were exposed to drugs as described in Examples 1 and 2 above, and then harvested and seeded into 96-well plates for use as target cells in a $^{51}$Cr-release cytotoxicity assay. Target cells were cultured overnight with $^{51}$Cr, and then washed. Human peripheral blood mononuclear cells which had been allowed to adhere overnight were added at a 50:1 effector: target ratio, and the ADCC cultures were incubated for 6 hours. Supernatants were collected and counted for radioactivity, and the percentage specific release was calculated. (see FIG. 4).

Figure 4:
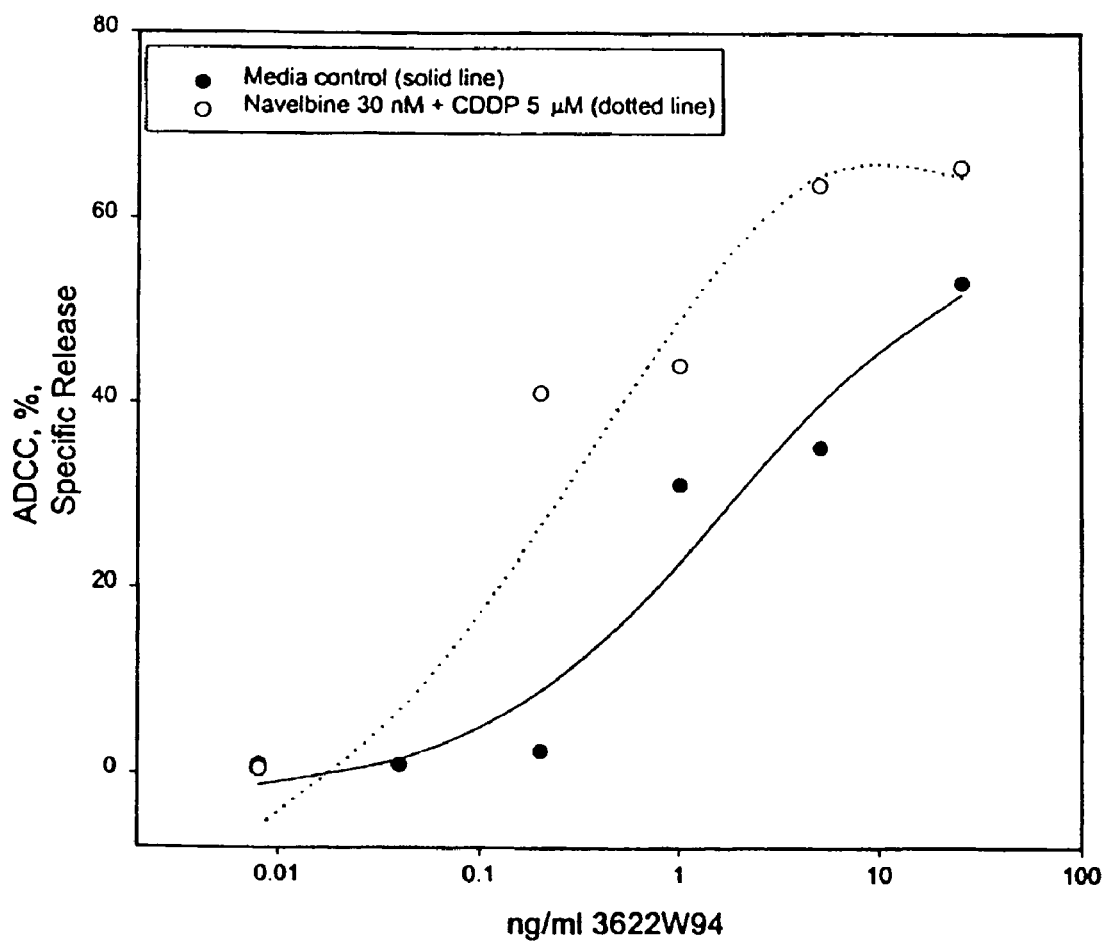

FIG. 4 clearly shows that PC-3 prostatic adenocarcinoma cells are better targets for human ADCC activity after exposure to Navelbine/Cisplatin compared to controls which have not been exposed to these chemotherapeutic agents. This effect may be due directly to increased antigen expression and thereby increased antibody binding, decreased modulation of the Ep-CAM antigen, increased fragility of the target cells, or a combination of the above.

EXAMPLE 5

Antibody Targeting to Ep-CAM-Positive Tumours was Significantly Improved by Pre-Treatment of the Mice with NAVELBINE Human colon adenocarcinoma (HT-29) tumours were initiated by subcutaneous implantation into female CD-1 nude mice (Charles River). When the tumours reached 200-300 mg, animals were divided into groups of five. Navelbine was injected intravenously at a dosage of 28 mg/kg on days 1 and 5. A control group was dosed with 5-fluorouracil (5-FU) intraperitoneally at 20 mg/kg on days 1 and 5. On day 6, humanised 323/A3 IgG$_{4cys-TMT}$ (a humanized monoclonal antibody chelator conjugate with specificity for the Ep-CAM antigen) was labelled with lutetium-177 and injected intravenously via the lateral tail vein. Each mouse received 4.1 μg protein/2.09 μCi lutetium-177/0.2 ml injection. Blood, spleen, liver, lung, kidney, femur and tumour were harvested on days 1, 3 and 5 post-antibody for direct gamma counting (see FIG. 5 for results).

Figure 5:
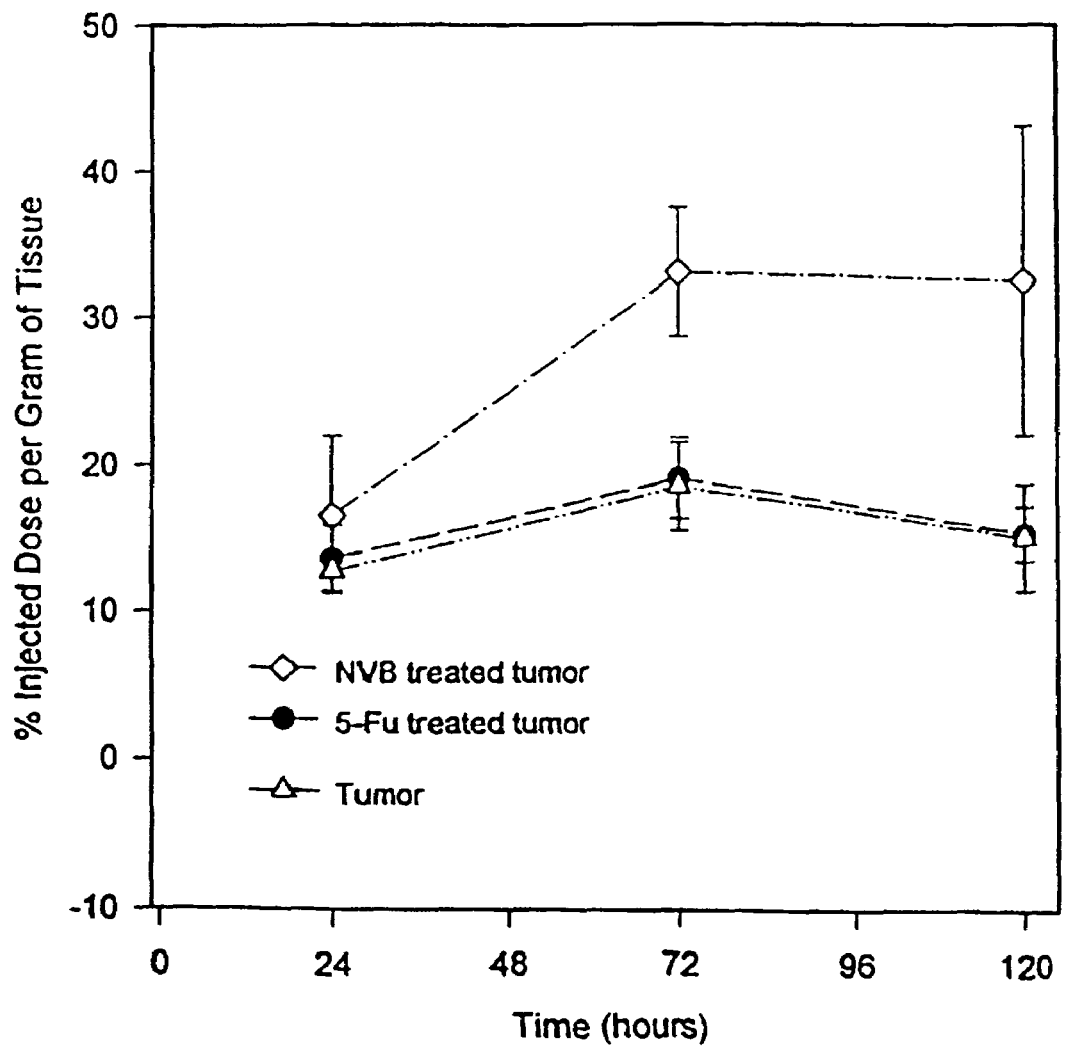

FIG. 5 shows that pre-treatment with Navelbine increases antibody targeting to Ep-CAM positive tumours whilst pre-treatment with 5-FU does not.

EXAMPLE 6

Expression of the Humanized Antibody 323/A3 (IgG$_1$) Variant in NSO Cells

1. Purpose/Summary

The cDNAs encoding the humanized 323/A3 antibody light and heavy chains (see FIGS. 15 and 16 respectively) were genetically engineered into a single Celltech glutamine synthetase (GS) expression plasmid, pEE18 (see FIG. 10), and used to transfect murine NSO cells.

2. Materials and Methods 2.1 Materials

NSO cells were obtained from Celltech Biologics plc, Slough, SL1 4EN, Berkshire, UK. The expression plasmids pEE6HCMV and pEE12 (see FIGS. 8 and 9) were obtained from Celltech Biologics plc, Slough.

2.2 The pEE6hmcv plasmid (see FIG. 8) encoding full length humanised heavy chain DNA was digested with Bam HI and Bgl II to liberate the 3.2 kb fragment that contained the DNA encoding the heavy chain under the transcriptional control of the major immediate early promoter of the human cytomegalovirus. This fragment was cloned into the Bam HI site of pEE12 (FIG. 9) that contained the DNA encoding the humanised light chain. (See FIG. 6 for humanised 323/A3 (IgG$_1$) Kappa light chain amino acid sequence and FIG. 7 for the humanised 323/A3(IgG$_1$) Heavy chain amino acid sequence. See FIG. 10 for schematic representation of the pEE18 plasmid encoding 323/A3 (IgG$_1$) heavy and light chains.

2.2.2 Transfection and Selection of NSO Cells 2.2.2.1 Tissue Culture

All single cell culture activities were performed in isolated rooms that contained a single laminar flow hood and single incubator dedicated solely to the use of NSO cells in the production of stable cell lines secreting humanised 323/A3(IgG$_1$). No other NSO cells lines, human cell lines or virus transformed cell lines were used within this environment.

A vial of NSO cells was revived and grown in 1:1:1 medium composed of DMEM:RPMI-1640:Sigma PFHM (1:1:1) to a cell density between 0.5 and $1 \times 10^6$ mL. For electroporation, the cells were harvested by centrifugation and washed once with PBS. pEE18 plasmid DNA encoding 323/A3 (IgG$_1$) was digested with Sal I, heat inactivated at 65° C. for 15 minutes, precipitated with ethanol and air-dried. The dried DNA pellet was resuspended in PBS to a concentration of 0.5 μg/mL and 100 μL aliquoted into a 2 mm electroporation cuvette (BTX). Washed NSO cells were resuspended at $1.2 \times 10^7$/ml and 400 μL added to the cuvette to give a final density of $10^6$ mL in a final volume of 0.5 mL. Electroporation was at 300 V for 1 msec in a BTX 8209 GenePulser followed by incubation on ice for 5-10 minutes. The electroporation mixture was resuspended at $10^5$ cells/mL with 1:1:1 medium and distributed over 96-well plates at 50 μL/well. The following day, wells were fed with 150 μL GS medium (Gln-free IMDM, 1=X GS and nucleoside supplement, 5% DFBS) to begin the GS selection process such that all wells had a final concentration of 3% DFBS.

2.2.2.2 Specific Production Rate (SPR)

Selected cell lines grown in GS media (3% DFBS) were seeded at a density of $0.2 \times 10^6$ cells/mL in T-25 flasks (Costar) that contained 5 mL of GS media (3% DFBS). Cells were incubated overnight at 37° C. for 24 hours after which an aliquot of each culture supernatant was removed. The supernatants were used in the human IgG ELISA assay to determine the concentration of secreted humanised 323/A3(IgG$_1$). The SPR value was derived by multiplying the concentration of 323/A3 (IgG$_1$) antibody in the supernatant times the volume (5.0) and is expressed as μg/$10^6$ cells/24 hours.

2.2.2.3 Cryopreservation of Cells

Selected cell lines were routinely harvested when cell density was greater than $0.2 \times 10^6$ cells/mL. An appropriate volume of cells was removed and subjected to centrifugation at 1,000×g for 5 minutes at 22° C. The cell pellet was gently resuspended to $1-4 \times 10^6$ cells/mL with ice-cold freezing media consisting of 20% (v/v) FBS/10-% (v/v) DMSO/GS Media (sterile filtered). Each 1.0 mL of the cell suspension was aliquoted into a 1.8 ml cryopreservation vial (NUNC) and gradually frozen overnight in a Cryo 1° C. Freezing Container (Nalgene) that had been placed in a −70° C. freezer. The vials were then removed from the container and stored in the vapour phase of a liquid nitrogen freezer.

Twenty vials of each cell line, including a low humanised 323/A3(IgG$_1$) producer were frozen down as described above and stored initially in the vapour phase of an MVE Cryogenics XLC440 liquid nitrogen freezer. The cells were subsequently transferred and stored in the vapour phase of an MVE Cryogenics XLC500 liquid nitrogen freezer.

EXAMPLE 7

Expression of the Humanized Antibody 323/A3 (IgG$_{4cys}$) in NSO Cells

1. Purpose Summary

The cDNAs encoding the humanized antibody 323/A3 (IgG$_{4cys}$) (a humanised 323/A3 antibody) antibody light and heavy chains (see FIGS. 15 and 17 were genetically engineered into a single Celltech glutamine synthetase (GS) expression plasmid, pEE18, and used to transfect murine NSO cells.

2. Materials and Methods 2.1 Materials (as for Example 6 above)

2.2

Creation of humanised 323/A3 (IgG$_{4cys}$ pEE18 Expression Plasmid The pEE6HMCV plasmid (see FIG. 8) encoding full length humanized heavy chain DNA was digested with BAM HI and Bgl II to liberate a 3.2 kb fragment that contained the DNA encoding the heavy chain under the transcriptional control of the major immediate early promoter of the human cytomeglovirus. This fragment was cloned into the Bam HI site of pEE12 that contained the DNA encoding the humanized light chain (See FIG. 11 for humanised 323/A3(IgG$_4$) Kappa Light Chain Amino Acid Sequence and FIG. 12 for the 323/A3IgG$_{4cys}$ variant Heavy Chain Amino Acid Sequence). See FIG. 10 for schematic representation of the pEE18 plasmid encoding 323/A3 heavy and light chains.

2.2.2 Transfection and Selection of NSO Cells: see Example 6 above.

EXAMPLE 8

Expression of the Humanized Antibody 323/A3 (IgG$_{2cys}$) in NSO Cells

1. Purpose/Summary

The cDNAs encoding the humanized 323/A3(IgG$_{2cys}$) antibody heavy and light chains were genetically engineered into a single Celltech glutamine synthetase (GS) expression plamid, pEE18, and used to transfect murine NSO cells.

2. Materials and Methods 2.1 Materials as for Examples 6 and 7 above 2.2 Creation of 323/A3 (IgG$_{2cys}$) pEE18 Expression for Plasmid The pEEE6 hcmv plasmid encoding full length humanized heavy chain DNA was digested with Bam HI and Bgl II to liberate 3.2 kb fragment that contained the DNA encoding the heavy chain under the transcriptional control of the major immediate early promoter of the human cytomegalovirus. This fragment was cloned into the Bam II site of pEE12 that contained the DNA encoding the humanized light chain (See FIG. 13 for 323/A3 (IgG$_{2cys}$) Kappa Light Chain Amino Acid Sequence and FIG. 14 for the 323/A3(IgG$_{2cys}$) Heavy Chain Amino Acid Sequence). See FIG. 10 for schematic representation of the pEE18 plasmid encoding 323/A3 (IgG$_{2cys}$) heavy and light chains.

2.2.2 Transfection and Selection of NSO Cells—See Examples 6 and 7 above.

---

The invention claimed is:

1. A combination comprising: an anti-Ep-CAM antibody with a chemotherapeutic agent wherein the chemotherapeutic agent is capable of arresting cell cycle production in S and/or G2/M in Ep-CAM expressing tumor cells and increasing the density of the Ep-Cam antigen population of the Ep-CAM expressing tumor cells, selected from the group consisting of: UFT, Capecitabine, CPT-II, Oxaliplatin, Paclitaxel, Docetaxel, Cyclophosphamide, Methotrexate, Doxorubicin, Navelbine (iv and oral), Epirubicin, Mitoxantrone, Raloxifen, Cisplatin, Carboplatinum, Gemcitabine, Etoposide and Topotecan.

2. The combination according to claim 1 wherein the Ep-CAM antibody is Panorex.

3. A combination comprising an anti-Ep-CAM antibody with a chemotherapeutic agent wherein the chemotherapeutic agent is capable of arresting of cell cycle production in S and/or G2/M in Ep-CAM expressing tumor cells and increasing the density of the Ep-Cam antigen population of the Ep-CAM expressing tumor cells, and wherein the chemotherapeutic agent is Docetaxel.

4. A combination comprising an anti-Ep-CAM antibody with a chemotherapeutic wherein the chemotherapeutic agent is agent capable of arresting of cell cycle production in S and/or G2/M in Ep-CAM expressing tumor cells, and increasing the density of the Ep-Cam antigen population of the Ep-CAM expressing tumor cells, and wherein the chemotherapeutic agent is Paclitaxel.

* * * * *